US009779879B2

(12) United States Patent
Nazeeruddin et al.

(10) Patent No.: US 9,779,879 B2
(45) Date of Patent: Oct. 3, 2017

(54) REDOX COUPLE FOR ELECTROCHEMICAL AND OPTOELECTRONIC DEVICES

(75) Inventors: Mohammad Khaja Nazeeruddin, Ecublens (CH); Michael Graetzel, St-Sulpice (CH); Etienne Baranoff, Birmingham (GB); Florian Kessler, Höchstadt an der Aisch (DE); Jun-Ho Yum, Préverenges (CH); Aswani Yella, St-Sulpice (CH); Hoi Nok Tsao, St-Sulpice (CH); Shaik Mohammad Zakeeruddin, Bussigny-Lausanne (CH)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 616 days.

(21) Appl. No.: 14/001,062

(22) PCT Filed: Feb. 24, 2012

(86) PCT No.: PCT/IB2012/050868
§ 371 (c)(1),
(2), (4) Date: Oct. 16, 2013

(87) PCT Pub. No.: WO2012/114315
PCT Pub. Date: Aug. 30, 2012

(65) Prior Publication Data
US 2014/0060641 A1 Mar. 6, 2014

(30) Foreign Application Priority Data

Feb. 25, 2011 (EP) .................................... 11156029
Apr. 8, 2011 (EP) .................................... 11161739
Apr. 11, 2011 (EP) .................................... 11161954

(51) Int. Cl.
*H01G 9/20* (2006.01)
*H01G 9/00* (2006.01)
(Continued)

(52) U.S. Cl.
CPC ......... *H01G 9/0029* (2013.01); *C07D 401/04* (2013.01); *C07D 401/14* (2013.01);
(Continued)

(58) Field of Classification Search
CPC .. C07D 401/04; C07D 401/14; H01G 9/2018; H01G 9/0083; H01G 9/0029;
(Continued)

(56) References Cited

U.S. PATENT DOCUMENTS

2004/0267018 A1* 12/2004 Elliott .................. C07D 213/22
546/2
2010/0029519 A1* 2/2010 Schwab ............... C10M 169/04
508/208

OTHER PUBLICATIONS

Feldt, Sandra M., et al., Design of Organic Dyes and Cobalt Polypyridine Redox Mediators for High-Efficiency Dye-Sensitized Solar Cells, Journal of the American Chemical Society, 2010, pp. 16714-16724, vol. 132, No. 46.
(Continued)

*Primary Examiner* — Matthew Martin
(74) *Attorney, Agent, or Firm* — Taft Stettinius & Hollister LLP

(57) ABSTRACT

The present invention provides an improved redox couple for electrochemical and optoelectronic devices. The redox couple is based on a complex of a first row transition metal, said complex containing at least one mono-, bi-, or tridentate ligand comprising a substituted or unsubstituted ring or ring system comprising a five-membered N-containing heteroring and/or a six-membered ring comprising at least two heteroatoms, at least one of which being a nitrogen atom, said five- or six-membered heteroring, respectively, comprising at least one double bond. The invention also relates to electrolytes and to the devices containing the complex, and to the use of the complex as a redox couple. The invention further provides electrochemical and/or optoelec-
(Continued)

tronic devices comprising a first and a second electrode and, between said first and second electrode, a charge transport layer, said a charge transport layer comprising tetracyanoborate ($[B(CN)_4]^-$) and a cationic metal complex functioning as redox-couple.

11 Claims, 16 Drawing Sheets

(51) Int. Cl.

| | |
|---|---|
| *H01L 51/00* | (2006.01) |
| *C07D 401/14* | (2006.01) |
| *C07D 401/04* | (2006.01) |
| *H01M 4/60* | (2006.01) |
| *H01M 10/0525* | (2010.01) |
| *H01M 10/0568* | (2010.01) |
| *C09B 57/10* | (2006.01) |
| *C09B 57/00* | (2006.01) |

(52) U.S. Cl.
CPC .............. *C09B 57/00* (2013.01); *C09B 57/10* (2013.01); *H01G 9/2018* (2013.01); *H01L 51/0083* (2013.01); *H01M 4/60* (2013.01); *H01M 10/0525* (2013.01); *H01M 10/0568* (2013.01); *H01G 9/2031* (2013.01); *H01G 9/2059* (2013.01); *Y02E 10/542* (2013.01); *Y02E 10/549* (2013.01); *Y02E 60/122* (2013.01); *Y02E 60/13* (2013.01)

(58) Field of Classification Search
CPC .... H01G 9/2031; H01G 9/2059; Y02E 60/13; Y02E 60/122; Y02E 10/542; Y02E 10/549

See application file for complete search history.

(56) References Cited

OTHER PUBLICATIONS

Ayers, Tim, et al., Redox and Spin State Control of Co(II) and Fe(II) N-heterocyclic Complexes, Inorganica Chimica Acta, 2000, pp. 7-12, vol. 307, Elsevier.

Savel'eva, Z.A., et al., Fe(II) Complex with Chiral Pyrazolylquinoline L and Fe(II), Co(II), and Cu(II) Complexes with Achiral Pyrazolyquinoline L1: Synthesis and Properties. The Crystal Structures of [ML1CL2] (M=Fe, Co, and Cu), Russian Journal of Coordination Chemistry, 2008, pp. 278-285, vol. 34, No. 4.

Larionov, S.V., et al., Cobalt(II) and Copper(II) Complexes with Chiral Pyrazolyquinoline, a Derivative of Terpenoid (+)-3-Carene. Catalytic Activity in Ethylene Polymerization Reaction, Russian Journal of Coordination Chemistry, 2007, pp. 436-448, vol. 33, No. 6.

Halcrow, Malcolm A., et al., Bis{2,6-bis[3-2,4,6-trimethylphenyl)-pyrazol-1-yl-kN2]pyridine-k-N}-cobalt(II) dinitrate at 290 and 150 K, Acta Crystallographica Section C Crystal Structure Communications, 2003, pp. M61-M63, vol. 59, No. 2.

Holland, Joanne M., Steric Effects on the Electronic and Molecular Structures of Nickel(II) and Cobalt(II) 2,6-dipyrazol-1-ylpridine Complexes, Polyhedron, 2001, pp. 2829-2840, vol. 20, No. 22-23, Elsevier.

Adhikari, N., Synthesis and Spectroscopic Characterization of Cobalt(II), Nickel(II) and Copper(II) Complexes with Ethyl-5-methyl-1-(2'-pyridyl) pyrazole-3-carboxylate, Oriental Journal of Chemistry, 2008, pp. 927-934, vol. 24, No. 3.

Ayers, Tim, et al., Tuning Redox and Spin State Properties of Fe(II) n-heterocyclic Complexes via Electronic/Steric Influence on Metal-Ligand Binding, Inorganica Chimica Acta, 2003, pp. 202-206, vol. 357, No. 1, Elsevier.

Singh, Shubha, et al., Synthesis and Properties of [MII(L6)2][ClO4]2 (M=Fe, Co and Ni): Structures of Co and Ni Complexes and Spin-state Transition by Fe Complex (L6=2-[3-(2'pyridyl)pyrazol-1-ylmethyl]-pyridine), Dalton Transactions, 2003, pp. 3392-3397, No. 17.

Mahapatra, S., et al., Highest CoIII-CoII Redox Potential in CoIIN6 (S=½) Complexes of Tridentate Ligands. Predominance of Steric Over Electronic Effect, Polyhedron, 1993, pp. 1477-1481, vol. 12. No. 12.

Baker, Anthony T., Five-Coordination in Complexes of 2-(3,5-Dimethylpyrazol-1-yl)quinoline, a Stedcally Hindered Diimine System, Australian Journal of Chemistry, 1984, pp. 2421-2429, vol. 37, No. 12.

Chohan, Zahid Hussain, et al., Synthesis, Characterisation & Antimicrobial Studies of Co(II) & Ni(II) Complexes with Some Pyrazoles, Indian Journal of Chemistry, 1988, pp. 1102-1104, vol. 27.

Gao, Feifei, et al., Enhance the Optical Absorptivity of Nanocrystalline TiO2 Film with High Molar Extinction Coefficient Ruthenium Sensitizers for High Performance Dye-Sensitized Solar Cells, Journal of the American Chemical Society, 2008, pp. 10720-10728, vol. 130, No. 32.

Shi, Dong, et al., New Efficiency Records for Stable Dye-Sensitized Solar Cells with Low-Volatility and Ionic Liquid Electrolytes, Journal of Physical Chemistry, 2008, pp. 17046-17050, vol. 112, N. 44.

Kuang, Daibin, et al., Stable, High-Efficiency Ionic-Liquid-Based Mesoscopic Dye-Sensitized Solar Cells, Small, 2007, pp. 2094-2102, vol. 3, No. 12, Wiley-VCH Verlag GmbH & Co.

Cao, Yiming, et al., Dye-Sensitized Solar Cells with a High Absorptivity Ruthenium Sensitizer Featuring a 2-(Hexylthio)thiophene Conjugated Bipyridine, Journal of Physical Chemistry, 2009, pp. 6290-6297, vol. 113, No. 15.

Zeng, Wangdong, et al., Efficient Dye-Sensitized Solar Cells with an Organic Photosensitizer Featuring Orderly Conjugated Ethylenedioxythiophene and Dithienosilole Blocks, Chemistry of Materials, 2010, pp. 1915-1925, vol. 22, No. 5.

Lv, Xueju, et al., Studies of an Extremely High Molar Extinction Coefficient Ruthenium Sensitizer in Dye-Sensitized Solar Cells, ACS Applied Materials & Interfaces, 2010, pp. 1980-1986, vol. 2. No. 7.

Wang, Mingkui, et al., The Influence of Charge Transport and Recombination on the Performance of Dye-Sensitized Solar Cells, ChemPhysChem, 2009, pp. 290-299, vol. 10, No. 1, Wiley-VCH Verlag GmbH & Co.

\* cited by examiner

H-29    H-30    H-31

J-1  J-2  J-3  J-4
J-5  J-6  J-7  J-8
J-9  J-10  J-11  J-12
J-13  J-14  J-15  J-16
J-17  J-18  J-19  J-20

L-1  L-2  L-3

L-4

M-1  M-2  M-3

M-4  M-5  M-6

M-7  M-8  M-9

M-10  M-11  M-12

N-15  N-16  N-17
N-18  N-19  N-20

P-1  P-2
P-3  P-4
P-5  P-6
P-7  P-8

REDOX COUPLE FOR ELECTROCHEMICAL AND OPTOELECTRONIC DEVICES

TECHNICAL FIELD

The present invention relates to complexes, which are useful in electrochemical and/or optoelectronic devices, electrochemical and optoelectronic devices comprising the complexes, as well as electrolytes comprising the complexes and various uses of the complexes.

PRIOR ART AND THE PROBLEM UNDERLYING THE INVENTION

The dye-sensitized solar cell (DSSC) is attracting wide spread attention as a promising new generation of photovoltaic technology. Mimicking the principle of natural photosynthesis, its ecological and economical fabrication processes make it an attractive and credible alternative to conventional photovoltaic systems (Gratzel, M. *Accounts Chem Res* 2009, 42, 1788-1798.).

One of the key components of the DSSC is the hole conductor (HC) transporting positive charge carriers from the sensitizer to the back contact of the device. Electrolytes containing the iodide/triiodide redox system are commonly used as HCs due to their high reliability and good power conversion efficiency (PCE) (Wang, Z.-S.; Sayama, K.; Sugihara, H. *The Journal of Physical Chemistry B* 2005, 109, 22449-22455). However, the $I^-/I_3^-$ redox couple suffers from too low a redox potential resulting in an excessive thermodynamic driving force for the dye regeneration reaction. This limits the open circuit potential of current DSSCs to 0.7-0.8 V. Iodide containing electrolytes also corrode a number of metals such as, for example, Ag and Cu, imposing restrictions on the use of such materials as current collectors in DSSC modules. It is noted that iodide and triiodide are very small molecules, which can easily reach the $TiO_2$ semiconductor surface that is often used in such devices. Contact with the semiconductor surface increases the chances of recombinations with the electrons in the semiconductor, ultimately decreasing the efficiency of the device. Furthermore, triiodide ($I_3^-$) absorbs light in competition with the sensitizing dye.

In this context the development of stable non-corrosive redox couples is warranted. A whole variety of alternative mediators have been investigated in the past including halogenides[5] or pseudohalogenides organic radicals or thiols and inorganic or organic p-type conductors. So far, all these redox mediators exhibited inferior PCEs compared to the $I^-/I_3^-$ couple, especially under full sunlight. This holds also for cobalt polypyridine complexes, reported in WO 03/038508, whose PCE under standard AM 1.5 conditions remained below 5% despite of extensive investigations over the last decade (Nusbaumer, H. et al., M. *J Phys Chem B* 2001, 105, 10461-10464).

Remarkably, Feldt et al. recently increased the PCE to 6.7% by employing a newly designed D-π-A sensitizer coded D35 in conjunction with cobalt (II/III) trisbipyridyl complex (Feldt, S. et al., *J. Am. Chem. Sec.* 2010, 132, 16714-16724). However, D35 harvest sunlight only below 620 nm limiting the short circuit photocurrent ($J_{SC}$) to 10-11 mA/cm$^2$.

In view of the above, the present invention addresses the problem of replacing the $I^-/I_3^-$ redox couple in photoelectrochemical conversion devices by a redox-couple exhibiting less corrosiveness to materials that might be of use in the preparation of DSSCs, such as metals and sealing materials, for example.

Furthermore, it is an objective to provide a redox-couple that does not exhibit a high overpotential for dye regeneration. It is an objective to provide a redox couple resulting in a relatively high or increased open current potential ($V_{OC}$) of the electrochemical device containing the redox couple. It is also an objective of the invention to provide a redox couple with a comparatively high oxidation potential, and/or an adjustable oxidation potential. In particular, it is an objective to provide a redox-couple the oxidation potential of which can be adjusted in dependence of other device parameters, for example to a particular dye, so that efficient charge transfer to the dye can take place, while still improving on $V_{OC}$ of the cell. It is an objective of the invention to provide a less light absorbing redox couple than iodide/triiodide system.

It is also an objective of the invention to provide more stable devices and devices having improved or higher conversion efficiency (PCE), which may be obtained by increasing $V_{OC}$ or in other ways.

It is a further objective of the invention to provide a redox couple the charge of which can be adjusted or varied. For example, in certain situations it is considered advantageous to provide a non-charged or negatively charged redox couple. This may apply to the reduced or to the oxidized state, or to both states.

It is also an objective to provide a less absorbing redox system.

The present invention addresses the problems depicted above, which are part of the invention.

SUMMARY OF THE INVENTION

Remarkably, the invention provides improved redox couples based on complex of first row transition metals containing a ligand comprising a substituted or unsubstituted ring or ring system comprising a five-membered heteroring and/or a six-membered ring comprising at least two heteroatoms. Surprisingly, the five- or six-membered heteroring affects the oxidation potential of the metal complex, thereby providing an effective redox couple with a high oxidation potential. The invention is further based on the finding that it is possible to advantageously adjust the oxidation potential by using suitable ligands and/or by choosing particular substituents or components in the ligand.

Furthermore, the invention provides a regenerative, dye-sensitized solar cell with metal complex-based redox couple in the charge transport layer. Advantageously, the complex-based redox couple is added in the form of a salt of tetracyanoborate ($B(CN)_4$).

Therefore, in an aspect, the present invention provides a complex comprising a first row transition metal containing a ligand comprising a substituted or unsubstituted ring or ring system comprising a five-membered heteroring and/or a six-membered ring comprising at least two heteroatoms.

In another aspect, the present invention provides an electrochemical, preferably photoelectrochemical, and/or optoelectronic device comprising tetracyanoborate and a metal-complex based redox couple and/or redox-active metal complex, wherein said tetracyanoborate and said metal complex may be added in the form of a salt.

In an aspect, the present invention provides a complex of formula (I) below:

$$M(La)_n(Xb)_m \qquad (I)$$

wherein:
M is a 1$^{st}$ row transition metal;
n is an integer from 1 to 6 and a is a consecutive number of a first set consisting of the integers of 1 to n (1, . . . , n), so that there are n ligands L1, . . . , Ln;
m is 0 or an integer from 1 to 5 and b is a consecutive number of a second set consisting of 0 and integers of 1 to m (0, . . . , m), so that if m>0 there are m ligands X1, . . . , Xm;
wherein n and m equal the appropriate number of ligands present on metal M;
any La (L1, . . . , Ln) is independently selected from a mono-, bi-, or tridentate ligand, with the proviso that at least one of La (L1, . . . , Ln) comprises a substituted or unsubstituted ring or ring system comprising a five-membered N-containing heterring and/or a six-membered ring comprising at least two heteroatoms, at least one of which being a nitrogen atom;
Xb is independently a monodentate co-ligand.

In an aspect, the present invention provides an electrochemical device comprising a first and a second electrode and, between said first and second electrode, a charge transport layer, said a charge transport layer comprising tetracyanoborate ([B(CN)$_4$]$^-$) and a cationic metal complex of formula I:

wherein:
M is a transition metal, preferably a 1$^{st}$ row transition metal, for example Cobalt;
n is an integer from 1 to 6 and a is a consecutive number of a set of integers (1, . . . , n), so that there are n ligands L1, . . . , Ln;
any La (L1, L2, . . . , Ln) is independently selected from mono-, bi-, and tridentate ligands, comprising a substituted or unsubstituted ring or ring system, said ring or ring system comprising at least one nitrogen atom;
m is 0 or an integer from 1 to 5 and, if m≥1, b is a consecutive number of a set of integers (1, . . . , m), so that, if m≥1, there are m ligands X1, . . . , Xm;
any Xb is independently a co-ligand; such as H$_2$O, Cl$^-$, Br$^-$, I$^-$, CN$^-$, NCO$^-$, NCS$^-$, NCSe$^-$, NH$_3$, NR$_{10}$R$_{11}$R$_{12}$, PR$_{10}$R$_{11}$R$_{12}$, R$_{10}$, wherein R$_{10}$, R$_{11}$, and R$_{12}$ may be selected, for example, independently from substituted or unsubstituted alkyl, alkenyl, alkynyl and phenyl; and,
wherein n and b equal the appropriate number of ligands present on metal M.

In an aspect, the present invention provides an electrochemical or optoelectronic device comprising the complex of the invention.

In an aspect, the present invention provides an electrochemical device comprising a first and a second electrode and, between said first and second electrode, an intermediate layer, for example an electrolyte layer, said intermediate layer comprising the complex of the invention.

In an aspect, the present invention provides a method of preparing an electrochemical device, the method comprising the steps of: providing a first and a second electrode, providing an intermediate layer, and adding the complex of the invention to the intermediate layer.

In an aspect the present invention provides the use of the complex of the invention as a redox-couple of an electrochemical device.

In an aspect, the present invention provides the use of ligands and substituents as detailed in this specification for adjusting the oxidation potential of a redox couple and/or of the complex of the invention.

In another aspect, the present invention provides an electrolyte comprising the complex of the invention.

In another aspect, the present invention provides a method of preparing a electrochemical device, the method comprising the steps of:
providing a first and a second electrode;
providing a charge transport layer;
adding to said charge transport layer a salt comprising tetracyanoborate ([B(CN)$_4$]$^-$) and a cationic metal complex of formula I:

wherein:
M is a transition metal, preferably a 1$^{st}$ row transition metal, for example Cobalt;
n is an integer from 1 to 6 and a is a consecutive number of the set of integers (1, . . . , n), so that there are n ligands L1, . . . , Ln;
any La (L1, L2, . . . , Ln) is independently selected from mono-, bi-, and tridentate ligands, comprising a substituted or unsubstituted ring or ring system, said ring or ring system comprising at least one nitrogen atom;
m is 0 or an integer from 1 to 5 and, if m≥1, b is a consecutive number of a set of integers (1, . . . , m), so that, if m≥1, there are m ligands X1, . . . , Xm;
any Xb is independently a co-ligand; such as H$_2$O, CN$^-$, NCO$^-$, NCS$^-$, NCSe$^-$, NH$_3$, NR$_{10}$R$_{11}$R$_{12}$, PR$_{10}$R$_{11}$R$_{12}$, R$_{10}$, wherein R$_{10}$, R$_{11}$, and R$_{12}$ may be selected, for example, independently from substituted or unsubstituted alkyl, alkenyl, alkynyl and phenyl; and,
wherein n and m equal the appropriate number of ligands present on metal M.

In an aspect, the present invention the use of a salt comprising tetracyanoborate and a metal-complex based redox couple in an electrochemical, a photoelectrochemical and/or an optoelectronic device.

Further aspects and preferred embodiments of the invention are defined herein below and in the appended claims. Further features and advantages of the invention will become apparent to the skilled person from the description of the preferred embodiments given below.

DETAILED DESCRIPTION OF THE PREFERRED EMBODIMENTS

Figure 1:
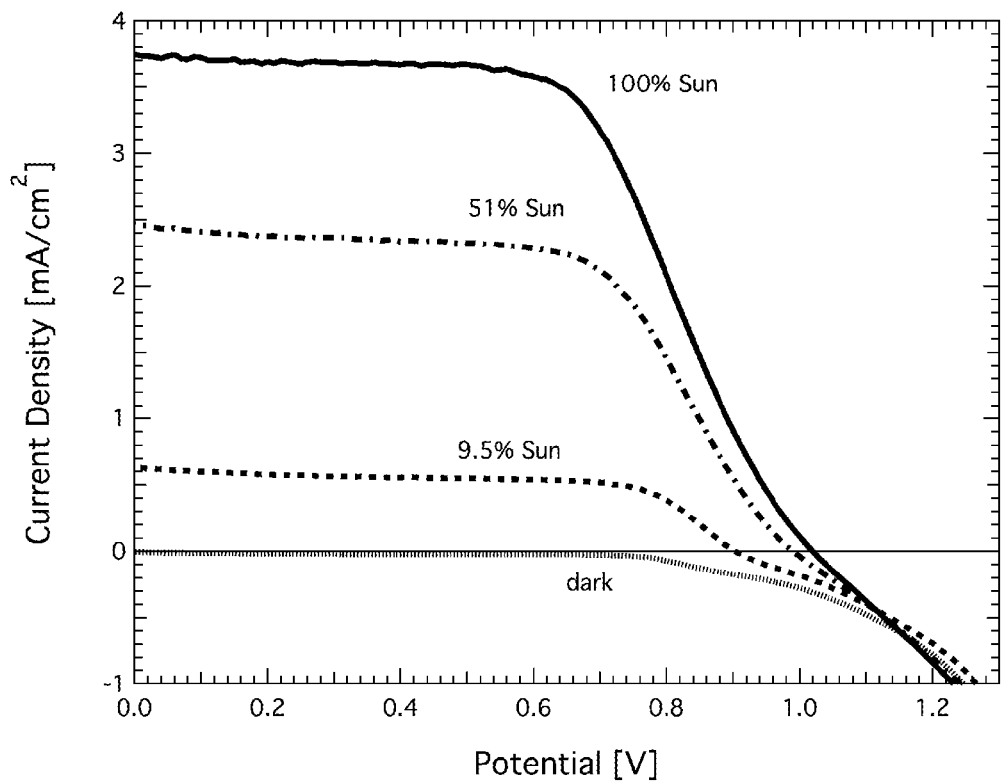
FIG. 1 shows Current (I)-Voltage (V) characteristic of a dye-sensitized solar cell containing the organic dye shown in FIG. 16 on 2.7 μm TiO$_2$ with cobalt bidentate redox couples using a bidentate ligand in accordance with an embodiment of the present invention.

The present invention provides complexes of transition metals and their use in electrochemical devices. The present invention further provides electrochemical and/or optoelectronic devices comprising a metal-based redox couple, in particular a redox-active compound comprising a metal atom. For the purpose of the present specification, the expression "redox-active compound" is the same as the "metal-based redox couple", and also encompasses the term "redox-active complex", "redox-compound" and the like.

The redox active compound preferably undergoes reduction and oxidation in the device of the invention, in particular when it is operating. For example, the redox active compound undergoes oxidation at a first electrode, for example a photoelectrode, and reduction at a second electrode, for example a counter electrode, or the inverse, depending on the use of the device.

The term "comprising", for the purpose of the present specification, is intended to mean "includes, amongst other". It is not intended to mean "consists only of".

According to an embodiment, the invention provides a metal complex comprising one or more ligands, such as, for example, ligands La and/or Xb as further detailed elsewhere in this specification. The metal complex preferably is preferably redox-active. According to an embodiment, the redox-active compound is a complex of formula (I):

$$M(La)_n(Xb)_m \qquad (I).$$

In the complex of formula (I), n is an integer from 1 to 6 and a is a consecutive number of a set of integers (1, . . . , n), so that there are n ligands: L1, . . . , Ln. For example, if n is 1, there is only one a, which is 1 and there is only one ligand La (L1).

If n is 2, "a" is a consecutive number of the set of integers (1, 2), so that there are two ligands La: ligands L1 and L2.

If n is 3, "a" is a consecutive number of the set of integers (1, 2, 3), so that there are three ligands La: L1, L2 and L3. If n is 4, there are the ligands L1, L2, L3, L4; if n is 5 there are the ligands L1, L2, L3, L4, L5; if n is 6 there are the ligands L1, L2, L3, L4, L5, L6. If n≥2, all ligands La are independently selected, so that they may all be the same, some of which may be the same, or all may be of different structure.

In the complex of formula (I), m is 0 or an integer from 1 to 5 and, if m≥1, b is a consecutive number of a set of integers (1, . . . , m), so that, if m≥1, there are m ligands: X1, . . . , Xm. For example, if m is 0, there is no ligand Xb. If m is 1, there is one ligand Xb (X1). If m is 2, there are two ligands Xb (X1, X2), which are independently selected. The same principle as set out above for n and the ligands La applies.

The ligands Xb may be absent. Preferably, the ligands Xb, in as far as present, is/are co-ligand(s) and/or spectator ligand(s). Preferably, any one ligand Xb is independently selected from monodentate ligands. Preferably, all ligands Xb, in as far as present, are monodentate ligands.

According to an embodiment, the complex comprises at least one mono-, bi-, and/or tridentate ligand comprising a substituted or unsubstituted ring or ring system, said ring or ring system comprising at least one nitrogen atom. Said ligand preferably corresponds to a ligand La in the metal-based complex of the invention.

According to another embodiment, the complexes contain at least one ligand comprising a substituted or unsubstituted five-membered heteroring and/or a six-membered ring comprising at least two heteroatoms.

According to an embodiment, the complex comprises at least one mono-, bi-, and/or tridentate ligand comprising a five- or six membered heteroring comprising at least one nitrogen atom, in particular a ring nitrogen atom. Said ligand preferably corresponds to a ligand La in the metal-based complex of the invention. According to an embodiment, said five- or six membered heteroring comprises one, two or more ring-heteroatoms, for example three or more ring heteroatoms, for example four ring heteroatoms. Ring heteroatoms, for the purpose of the present specification, are preferably selected independently from O, N, and S.

According to an embodiment, said five- or six membered heteroring comprises two or more ring nitrogen atoms, for example three or more ring nitrogen atoms, for example four ring nitrogen atoms.

According to an embodiment, said five- or six membered heteroring comprises two or more ring nitrogen atoms, for example three or more ring nitrogen atoms, for example four ring nitrogen atoms.

According to an embodiment, the complex is a complex of formula (I):

$$M(La)_n(Xb)_m \quad (I)$$

wherein:
M is a metal atom, preferably a transition metal, more preferably a $1^{st}$ row transition metal, for example Cobalt;
n is an integer from 1 to 6 and a is a consecutive number of a first set consisting of the integers of 1 to n (1, . . . , n), so that there are n ligands L1, . . . , Ln;
m is 0 or an integer from 1 to 5 and b is a consecutive number of a second set consisting of 0 and integers of 1 to m (0, . . . , m), so that if m>0 there are m ligands X1, . . . , Xm;
wherein n and m equal the appropriate number of ligands present on metal M;
any La (L1, . . . , Ln) is independently selected from a mono-, bi-, or tridentate ligand, with the proviso that at least one of La (L1, . . . , Ln) comprises a substituted or unsubstituted ring or ring system comprising a five-membered N-containing heteroring and/or a six-membered ring comprising at least two heteroatoms, at least one of which being a nitrogen atom, said five- or six-membered heteroring, respectively, comprising at least one double bond;
Xb is independently a monodentate co-ligand.

According to another embodiment, in particular with respect to the electrochemical and/or optoelectronic device comprising a charge transport layer comprising tetracyanoborate ($[B(CN)_4]^-$) and a cationic metal complex of formula I, any La (L1, L2, . . . , Ln) is independently selected from mono-, bi-, and tridentate ligands, comprising a substituted or unsubstituted ring or ring system, said ring or ring system comprising at least one nitrogen atom.

The metal atom of the complex, for example M, is preferably selected from first row transition metals. The metal atom M may thus be selected preferably from the metals Sc, Ti, V, Cr, Mn, Fe, Co, Ni, Cu, and Zn. Preferably, M is selected from Fe, Co, Ni, Cu. Most preferably, M is cobalt (Co). As the complex of the invention forms a redox couple, the metal atom M may be present at different oxidation levels in the complex of the invention. For example, the metal atom may be present in the +II and +III oxidative states. Accordingly, the reversible reduction and/or oxidation of the metal atom accounts for the redox-activity of the redox-active compound and/or the metal-based redox couple.

Since n may be an integer from 1 to 6, the complex of formula (I) contain at least one but possibly up to six ligands La. The different embodiments are shown below at the example of complexes of formulae (II)-(XXI):

In case n is 1 and L1 is a monodentate ligand, m is 5:

ML1X1X2X3X4X5, wherein X1 to X5 may be the same or different. (II)

In case n is 1 and L1 is a bidentate ligand (m is 4):

ML1X1X2X3X4, wherein X1 to X4 may be the same or different. (III)

In case n is 1 and L1 is a tridentate ligand (m is 3):

ML1X1X2X3, wherein X1 to X3 may be the same or different. (IV)

In case n is 1 and L1 is a tetradentate ligand (m is 2):

ML1X1X2, wherein X1 to X2 may be the same or different. (V)

In case n is 2 and L1 and L2 are both monodentate ligands (m is 4):

ML1L2X1X2X3X4, wherein L1 and L2 may be the same or different, and any one of X1 to X4 may be the same or different. (VI)

In case n is 2 and L1 and L2 are both bidentate ligands (m is 2):

ML1L2X1X2, wherein L1 and L2 may be the same or different, and X1 and X2 may be the same or different. (VII)

In case n is 2, L1 and L2 are a mono- and a bidentate ligands, respectively (m is 3):

ML1L2X1X2X3, wherein L1 and L2 are different, and any one of X1 to X3 may be the same or different. (VIII)

In case n is 2 and L1 and L2 are a mono- and a tridentate ligand, respectively (m is 2):

ML1L2X1X2, wherein L1 and L2 are different and any one of X1 and X2 may be the same or different. (IX)

In case n is 2, L1 is a bidentate ligand and L2 is a tridentate ligand (m is 1):

ML1L2X1, wherein L1 and L2 are different. (X)

In case n is 2 and L1 and L2 are both tridentate ligands (m is 0):

ML1L2, wherein L1 and L2 may be the same or different. (XI)

In case n is 3 and L1, L2 and L3 are all monodentate ligands (m is 3):

ML1L2L3X1X2X3, wherein any one of L1 to L3 may be the same or different and any one of X1 to X3 may be the same or different. (XII)

In case n is 3 and L1, L2 and L3 are all bidentate ligands (m is 0):

ML1L2L3, wherein any one of L1, L2 and L3 may be, independently, the same or different from any other of L1, L2, L3, respectively. For example, L1 to L3 may all be the same. (XIII)

In case n is 3, L1 is a bidentate ligand and, L2 and L3 are both monodentate ligands (m is 2):

ML1L2L3X1X2, wherein L1 is different from L2 and L3, L2 and L3 may be the same or different, X1 and X2 may be the same or different. (XIV)

In case n is 3, L1 is a tridentate ligand, L2 and L3 are both monodentate ligands (m is 1):

ML1L2L3X1, wherein L1 is different from L2; L3 and L2 may be the same or different. (XV)

In case n is 3, L1 is a tridentate ligand, L2 is a bidentate ligand and L3 is a monodentate ligand (m is 0):

ML1L2L3, wherein L1, L2 and L3 are all different. (XVI)

In case n is 4, L1 is a bidentate ligand, L2 to L4 are monodentate ligands (m is 1):

ML1L2L3L4X1, wherein L1 is different from L2 to L4; and any one of L2 to L4 may be the same or different. (XVII)

In case n is 4, L1 is a tridentate ligand, L2 to L4 are monodentate ligands (m is 0):

ML1L2L3L4, wherein L1 is different from L2 to L4; and any one of L2 to L4 may be the same or different. (XVIII)

In case n is 4 and L1 to L4 are all monodentate ligands (m is 2):

ML1L2L3L4X1X2, wherein any one of L1 to L4 may be the same or different and X1 and X2 may be the same or different. (XIX)

In case n is 5, L1 is a bidentate ligand and L2 to L5 are all monodentate ligands (m is 0):

ML1L2L3L4L5, wherein L1 is different from L2 to L5 but L2 to L5 may be the same or different. (XX)

In the other cases where n is 5 (or 6), m is 1 (or 0, respectively), L1 to L5 (or L1 to L6, respectively), are all monodentate ligands, which may be the same or different.

From the above it becomes apparent that the complexes of the invention may be homoleptic (contain identical ligands La with m being 0) or heteroleptic (containing at least two different ligands).

Preferably, n is 1, 2 or 3, more preferably 2 or 3. If n is 2, L1 and L2 are preferably identical. If n is 3, L1 to L3 are preferably identical.

According to an embodiment of the complex of the invention, n is 2 (M L1 L2) or 3 (M L1, L2, L3) and m is 0 in both cases.

According to an embodiment, the complex of the invention comprises at least 2 or at least 3 ligands La of identical structure (L1=L2 or L1=L2=L3, respectively).

According to an embodiment, n is an integer of 1 to 3, preferably 2 or 3.

It is noted that n and m equal the appropriate number of ligands present on metal M. The parameters n and m, as well as their sum, thus depends on the metal atom and of the valency of the ligands La and Xb (if they are mono-, bi-, or tridentate ligands). For example, if the metal is cobalt, there are generally 6 complex bonds possible to the metal, so that for example, if there are two tridentate ligands La, n is 2 and m is 0. In the same case, if there are three bidentate ligands La, m is 3 and m is 0.

According to an embodiment, the complex of the invention is overall neutral, or carries an overall positive or negative charge. As can be seen from the ligands of the invention as detailed elsewhere in this specification, the charge of the entire complex can be adjusted to be neutral or even negatively charged, in the oxidized or reduced state, as desired, by selecting appropriate negatively charged ligands. For the purpose of the present specification it is considered to be advantageous to be capable of adjusting the charge of the complex, in order to adjust said charge in dependency of other constituents of the electrochemical device of the invention. In particular, the charge of the redox couple can be adjusted to be neutral or negatively charged, so as to avoid electrostatic interactions with other constituents of the device, such as the dye, for example.

Herein below, preferred embodiments of the at least one ligand of the invention are given. According to an embodiment, said ligand comprises a substituted or unsubstituted ring or ring system comprising a five-membered heteroring and/or a six-membered ring comprising at least two heteroatoms. These embodiments also apply for the ligands La (L1, . . . Ln) of the complex of formula (I).

The five- or six membered heteroring may be, independently provided as an unsubstituted or substituted heteroring. The heteroring may be fused to another ring or ring system, and/or two substituents of/on a carbon of the heteroring may form a ring, which may result in a spiro compound in which one of the rings is said five- or six membered heteroring. Furthermore, the five- or six membered heteroring may be connected by a covalent bond to another ring or ring system, for example to a pyridine ring or to a polycyclic system containing one pyridine or more ring.

Preferably, substituted or unsubstituted five- or six membered heteroring (the six membered heteroring comprising at least two heteroatoms), comprises at least one double bond. More preferably, the five- or six membered heteroring is aromatic.

According to a preferred embodiment, the complex of the invention comprises at least one, more preferably at least two, even more preferably at least three bidentate ligands La, which may be the same or different.

According to another, still more preferred embodiment, the complex of the invention comprises at least one, preferably at least two tridentate ligands La, which may be the same or different.

According to an embodiment, at least one of said n ligands La (L1, . . . , Ln) comprises a pyridine ring or a ring system comprising a pyridine ring connected by a covalent bond or fused to said five-membered heteroring and/or to said six-membered ring comprising at least two heteroatoms, wherein said pyridine ring or a ring system comprising a pyridine ring may or may not be further substituted.

According to an embodiment, said five- or six membered ring comprises at least on heteroatom selected from the group of N, O, P and S, preferably at least one N.

According to an embodiment, said five-membered heteroring comprises two or more (preferably up to 4) heteroatoms, and said six-membered heteroring comprises two or more (preferably up to 4) heteroatoms. Preferably, at least a first heteroatom is nitrogen, and at least a second heteroatom or further heteroatom is/are selected, independently, from N, O, P and S. Preferably, said second heteroatom is N, and, if applicable, further heteroatoms (the third, fourth, etc.) are selected independently, from N, O, P and S, preferably they are N.

According to another embodiment, ligands, in particular any ligand La of the redox-active compound, is independently selected from substituted and unsubstituted pyridine or polypyridine (for example, bi- and tripyridine) ligand, substituted and unsubstituted pyrazole, substituted and unsubstituted pyrazine, substituted and unsubstituted triazole, substituted and unsubstituted tetrazole, substituted and unsubstituted pyridazine, substituted and unsubstituted imidazole; wherein substituents are independently selected from hydrocarbons comprising 1 to 40 carbons and 0 to 25 heteroatoms, halogen, (—F, —Cl, —Br, —I), —NO$_2$, and —OH.

Substituents of said pyridine, polypyridine, pyrazole, pyrazine, triazole, pyridazine, and imidazole, in as far as present, may be selected as any one of substituents of $R^1$, $R^2$, $R^3$, $R^4$, $R^5$, $R^6$, $R^7$, $R^8$, $R_1$, $R_2$, $R_3$, $R_4$, $R_5$, and $R_6$ as defined elsewhere in this specification, including from preferred embodiments of these substituents $R^1$-$R^8$ and $R_1$-$R_7$.

According to an embodiment, at least one ligand of the complex of the invention is, independently, selected from compounds of formulae (1)-(63) below. Preferably any one of said n ligands La (L1, . . . , Ln) of the complex of formula (I), or of any one of the complexes of formula (II) to (XVII), in as far as applicable, is, independently, selected from compounds of formulae (1)-(63) below:
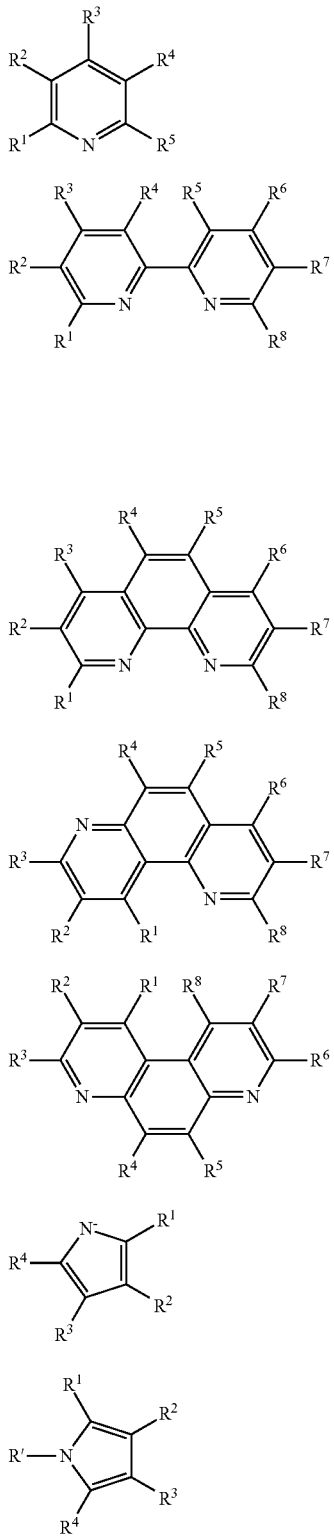
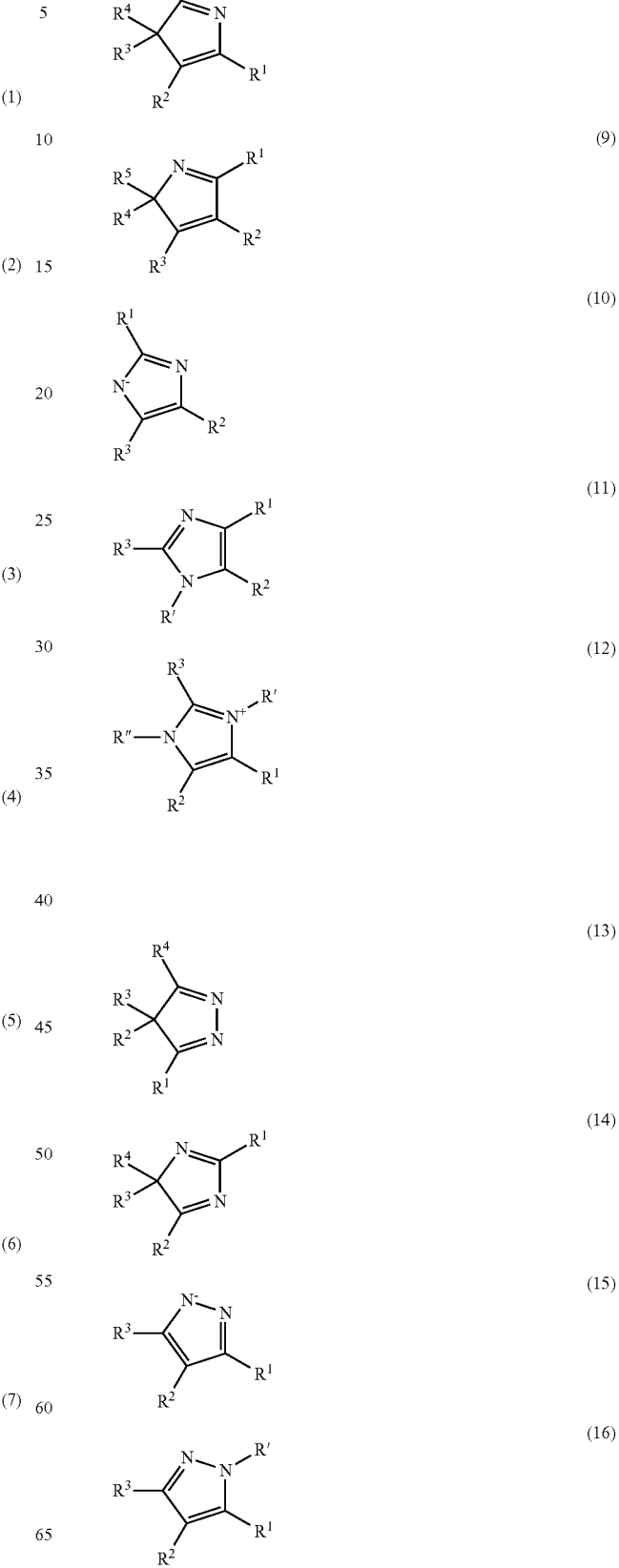

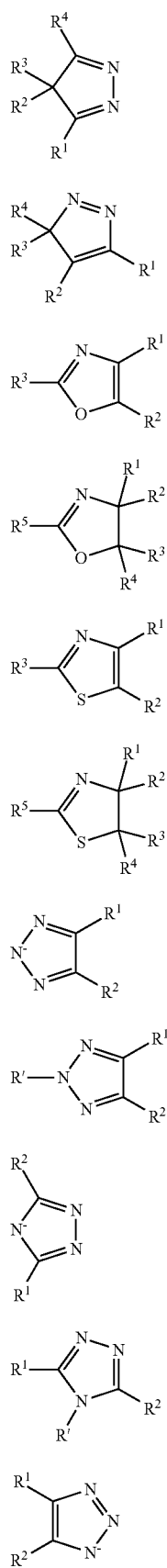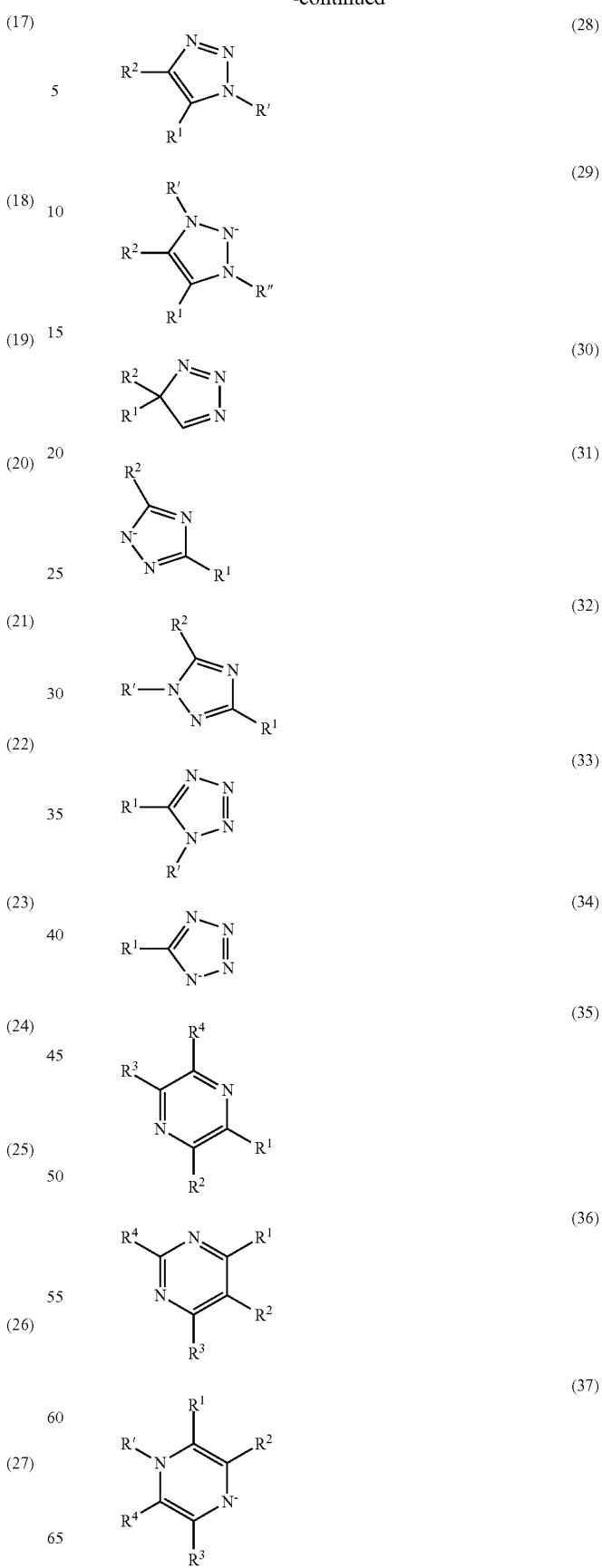

(38) 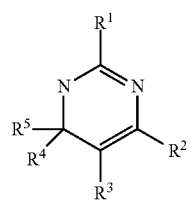
(39) 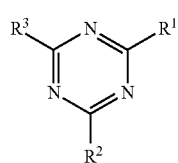
(40) 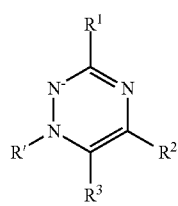
(41) 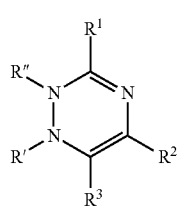
(42) 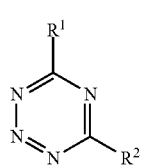
(43) 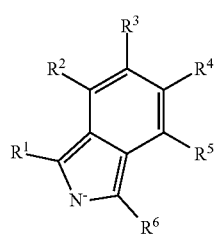
(44) 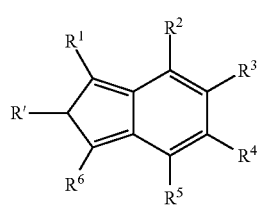
(45) 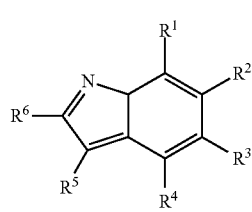
(46) 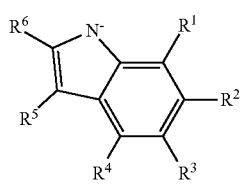
(47) 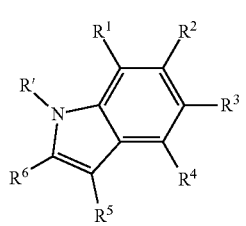
(48) 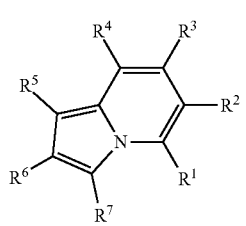
(49) 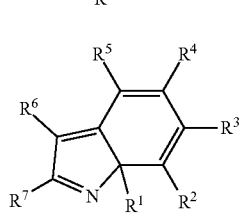
(50) 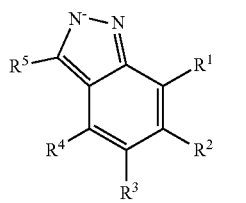
(51) 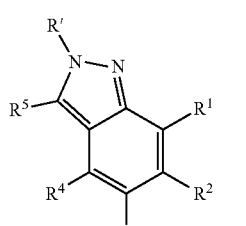
(52) 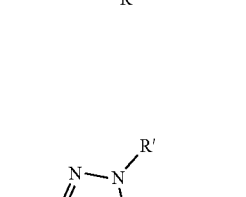
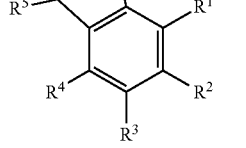

-continued

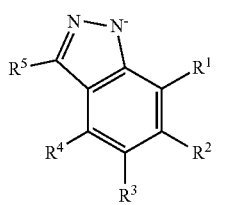 (53)

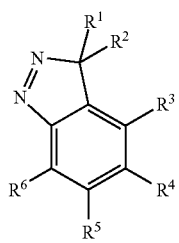 (54)

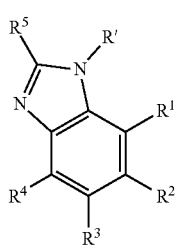 (55)

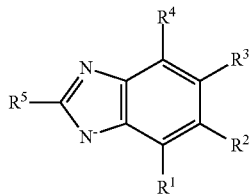 (56)

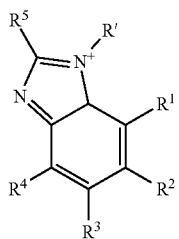 (57)

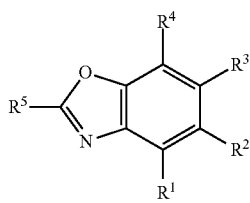 (58)

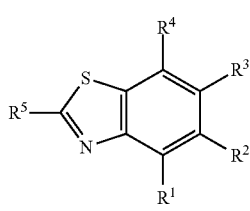 (59)

-continued

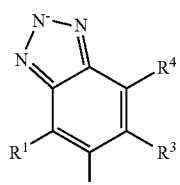 (60)

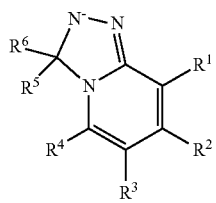 (61)

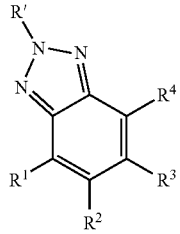 (62)

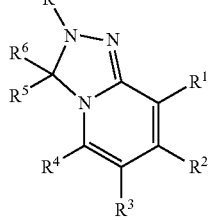 (63)

wherein:
any one of $R^1$, $R^2$, $R^3$, $R^4$, $R^5$, $R^6$, $R^7$, $R^8$, if applicable, may be selected, independently, from H, halogen (F, Cl, Br, I), —$NO_2$, —$NH_2$, —OH, and from hydrocarbons comprising 1 to 50 carbons and 0 to 20 heteroatoms, preferably said hydrocarbons comprise 1 to 30 carbons and 0 to 20 heteroatoms;

R' and R" are selected, independently from substituents —$CH_2R^1$, —$CHR^1R^2$ and —$CR^1R^2R^3$;

with the proviso that, if the compound is a compound according to any one of formulae (1) to (5) above, at least one of said substituents $R^1$, $R^2$, $R^3$, $R^4$, $R^5$, $R^6$, $R^7$, $R^8$, in as far as present, is selected, independently, from a substituent of formula (A-1) to (G-2) below:

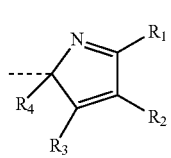 (A-1)

(A-2) 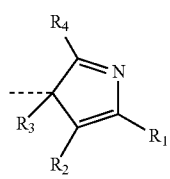
(A-3) 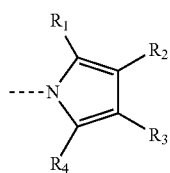
(A-4) 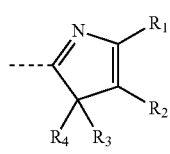
(A-5) 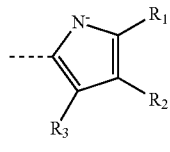
(A-6) 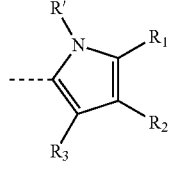
(B-1) 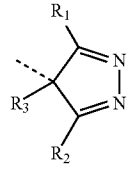
(B-2) 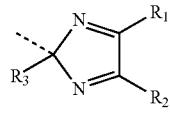
(B-3) 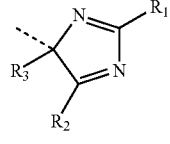
(B-4) 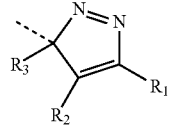
(B-5) 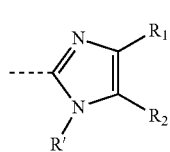
(B-6) 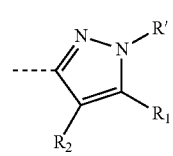
(B-7) 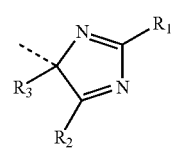
(B-8) 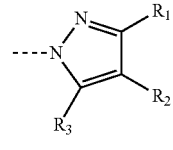
(B-9) 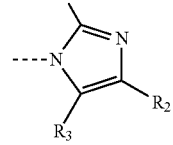
(B-10) 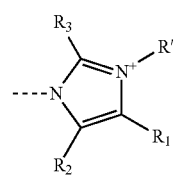
(B-11) 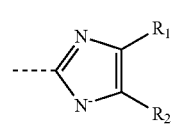
(B-12) 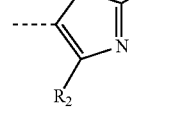
(B-13) 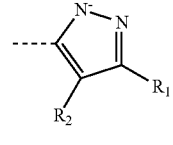
(B-14) 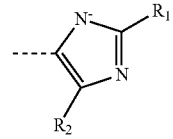
(B-15) 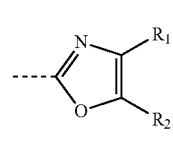

-continued
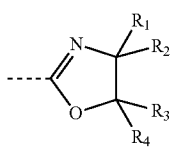
(B-16)
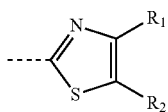
(B-17)
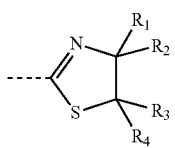
(B-18)
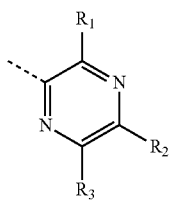
(B-21)
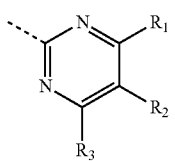
(B-22)
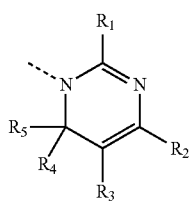
(B-23)
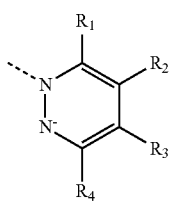
(B-24)
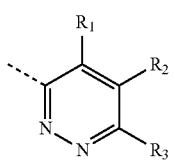
(B-25)
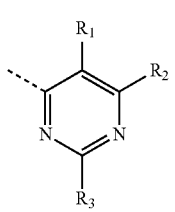
(B-26)
-continued
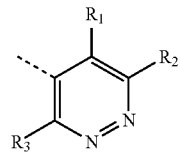
(B-27)
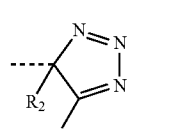
(C-1)
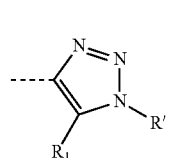
(C-2)
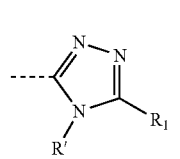
(C-3)
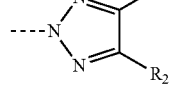
(C-4)
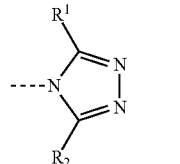
(C-5)
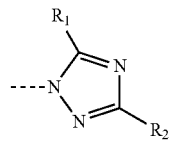
(C-6)
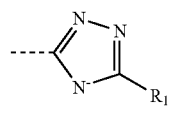
(C-7)
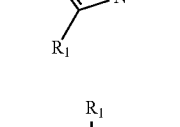
(C-8)
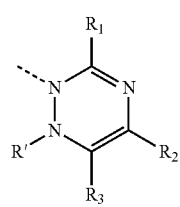
(C-9)

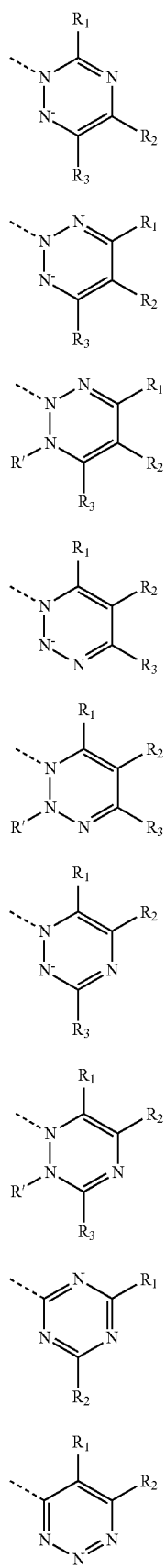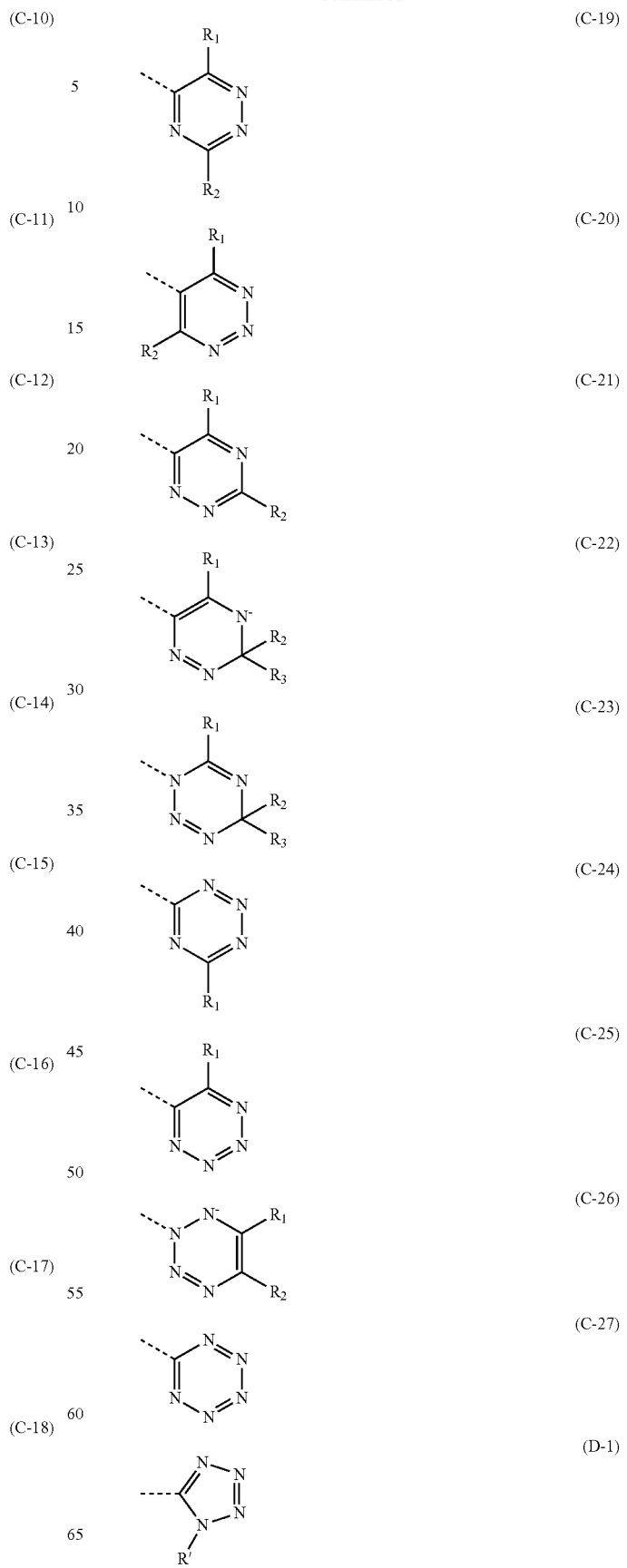

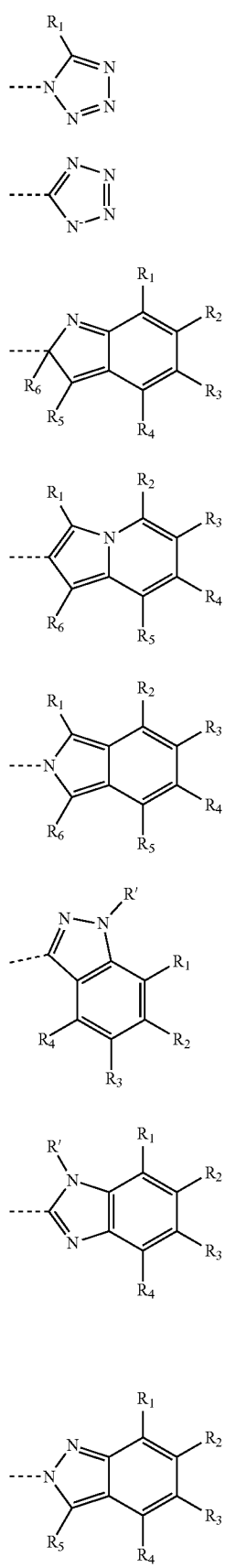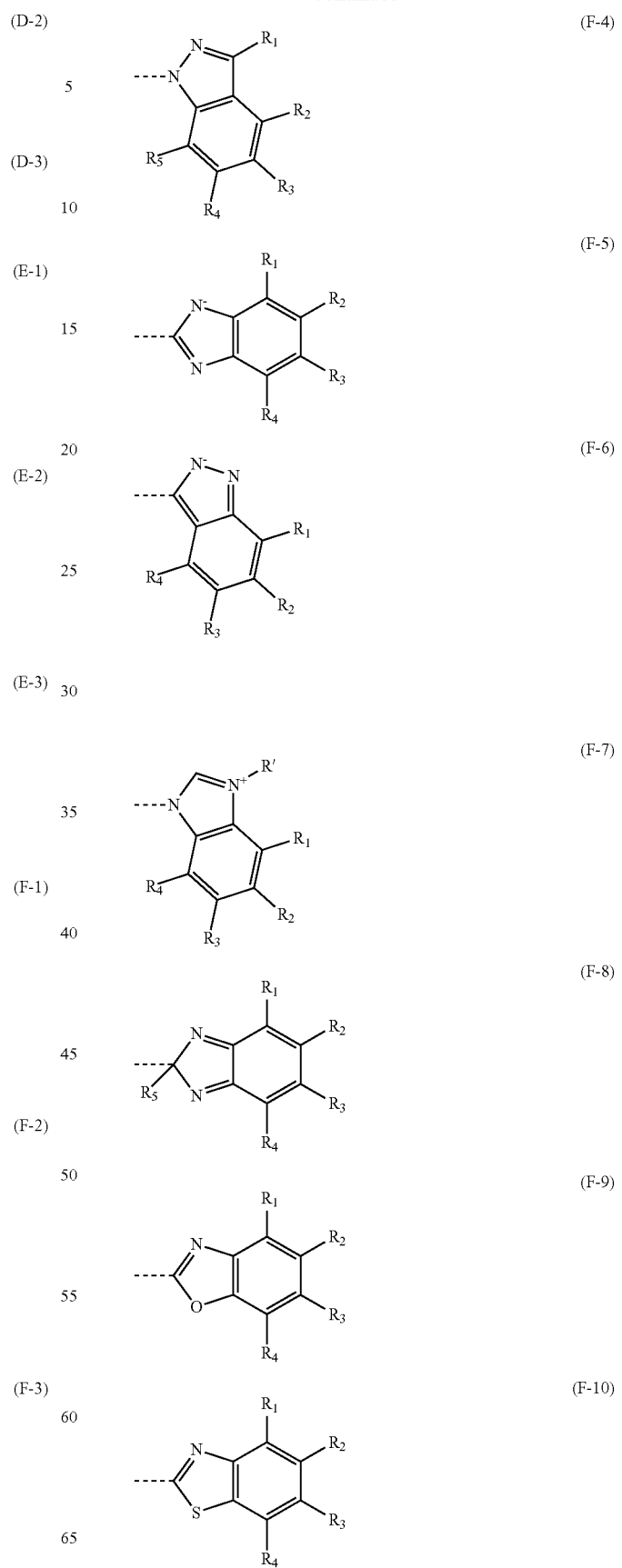

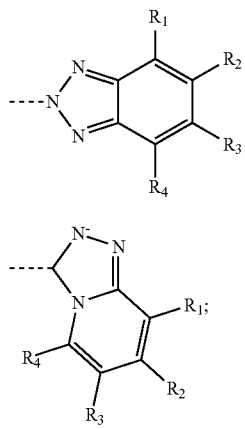

(G-1)

(G-2)

wherein the dotted line represents the bond connecting the substituent of (A-1) to (G-2) on the compound of formula (1)-(63); and, substituents $R_1$, $R_2$, $R_3$, $R_4$, $R_5$, and $R_6$, in as far as present, are independently selected from H, halogen (F, Cl, Br, I), —$NO_2$, —$NH_2$, —OH, and from hydrocarbons comprising and/or consisting of 1 to 50 carbons and 0 to 20 heteroatoms, preferably from hydrocarbons comprising and/or consisting of 1 to 50 carbons and 0 to 15 heteroatoms. R' and R" are as defined above and elsewhere in this specification.

It is noted, however, that electron accepting substituents (comprising, for example halogen —$CF_3$, —CN) are preferred.

A "hydrocarbon", for the purpose of the present specification, is a compound or substituent comprising at least one carbon atom. The substituent —C≡N (—CN), and —$CF_3$ are considered to be hydrocarbons.

Compounds (6) to (63) can be provided in the form of monodentate ligands, whereas compounds (1) to (5), which, according to an embodiment, contain at least one substituent according to formulae (A-1) to (G-2), are generally bi- or tridentate ligands. Depending on the choice of the substituents $R^1$ to $R^8$ (in as far as applicable), compounds (6) to (63) may also be provided in the form of bi- or tridentate ligands La (L1, . . . , Ln).

Any one of $R^1$, $R^2$, $R^3$, $R^4$, $R^5$, $R^6$, $R^7$, $R^8$, and of $R_1$, $R_2$, $R_3$, $R_4$, $R_5$, and $R_6$, in as far as the respective substituent is present on the compounds (1) to (63) or of the group of compounds (1) to (42) and their substituents, may thus be independently selected from H and from hydrocarbons comprising 1 to 50 carbons and 0 to 20 heteroatoms, if applicable under the proviso mentioned elsewhere in this specification.

It is noted that if a redox-active complex of the present invention comprises two or more different ligands, such as, for example, two or more different ligands selected independently from compounds (1) to (63) above or of the group of compounds (1) to (42) as defined elsewhere in this specification, any given substituent of substituents $R^1$, $R^2$, $R^3$, $R^4$, $R^5$, $R^6$, $R^7$, $R^8$, and/or $R_1$, $R_2$, $R_3$, $R_4$, $R_5$, and $R_6$, in as far as present (meaning any substituent with a given substituent numeral) does not need to be the same on said two (potentially different) ligands and can thus be independently selected. For example, in case the redox-active complex comprises two ligands according to formula (66) (see below), any $R^1$ on said one of these two ligands of formula (66) may be different from the substituent $R^1$ on the respective other substituent of formula (66). Similarly, in case the redox-active complex comprises two different ligands selected independently from the compounds of formulae (1)-(67), for example a ligand of formula (66) and a ligand of formula (67), any $R^1$ (and all other substituents having the same substituent number) present on these two ligands are independently selected and may thus be the same or different. In other words, for any given ligand La, the respective substituents $R^1$-$R^7$, or $R^1$-$R^8$, and $R_{1-6}$ are selected independently from substituents $R^1$-$R^7$ or $R^1$-$R^8$, and $R_{1-6}$ possibly present on another ligand La. This does not apply to embodiments where ligands La are identical.

According to a preferred embodiment of the devices of the invention comprising a charge transport layer comprising tetracyanoborate ($[B(CN)_4]^-$) and a cationic metal complex of formula I, reference to the compounds of formulae (1) to (63) specifically refers to the group of compounds (1), (2), (3), (6), (7), (10), (11), (12), (15), (16), (23), (24), (25), (26), (27), (28), (29), (30), (31), (32), (33), (34), (35), (36), (37), (39), (40), (41), and (42), which may be specified as the "group of compounds (1) to (42)".

According to a preferred embodiment of the devices of the invention comprising a charge transport layer comprising tetracyanoborate ($[B(CN)_4]^-$) and a cationic metal complex of formula I, the reference to the substituents of formulae (A-1) to (G-2) more specifically refers to one or more of the substituents of the group consisting of (A-3), (A-5), (A-6), (B-5), (B-6), (B-8), (B-9), (B-10), (B-11), (B-12), (B-13), (B-14), (B-15), (B-17), (B-21), (B-22), (B-24), (B-25), (B-26), (B-27), (C-2), (C-3), (C-4), (-5), (C-6), (C-7), (C-8), (C-9), (C-10), (C-11), (C-13), (C-14), (C-15), (C-16), (C-12), (C-17), (C-18), (C-19), (C-20), (C-21), (C-24), (C-25), (C-26), (C-27), (D-1), (D-2), (D-3), (E-1), (E-2), (E-3), (F-1), (F-2), (F-3), (F-4), (F-5), (F-6), (F-7), (F-9), (F-10), (G-1), and (G-2), which group is preferably specified herein as the group of "(A-3) to (G-2)".

Heteroatoms are preferably selected, independently, from Si, N, P, As, O, S, Se halogen (in particular F, Cl, Br and I), B, Be; more preferably from Si, N, P, O, S, and halogen, most preferably from N, O, S and halogen.

According to an embodiment, any one of said substituents $R^1$, $R^2$, $R^3$, $R^4$, $R^5$, $R^6$, $R^7$, $R^8$, and of $R_1$, $R_2$, $R_3$, $R_4$, $R_5$, and $R_6$, may be independently selected from H, halogen, —F, —Cl, —Br, —I, —$NO_2$, —CN, —OH, —$CF_3$, substituted or unsubstituted C1-C50 alkyl, C2-C50 alkenyl, C2-C50 alkynyl, and C4 or C5 to C50 aryl; wherein, in said substituted or unsubstituted alkyl, alkenyl, alkynyl or aryl, any hydrocarbon group (preferably and if applicable: non adjacent hydrocarbon group) may be replaced by any one selected from the group of —O—, —S—, —S(=O)—, —S(=O)$_2$—, —Si—, —Ge—, —$NR^A$—, —N=, —$BR^A$—, —$PR^A$—, —P(=O)$R^A$—, —P(=O)O$R^A$—, —C(=O)—, —C(=S)—, —C(=O)O—, —OC(=O)—, —C(=$NR^A$)—, —C=$NR^A$—, —$NR^A$C(=O)—, —C(=O)$NR^A$—, —$NR^A$C(=S)— and —C(=S)$NR^A$—; wherein, if said alkyl, alkenyl, alkynyl and aryl are substituted, the substituents, and said $R^A$, if present, may, independently, be selected from halogen, —F, —Cl, —Br, —I, —$NO_2$, —CN, —OH, —$CF_3$, substituted or unsubstituted C1-C15 alkyl, C2-C15 alkenyl, C2-C15 alkynyl C2-C15 alkynyl, C4 or C5 to C18 aryl, wherein any hydrocarbon group of said substituent may be replaced by any one selected from the group of —O—, —S—, —S(=O)—, —S(=O)$_2$—, —Si—, —Ge—, —$NR^A$—, —N=, —$BR^B$—, —$PR^B$—, —P(=O)$R^B$—, —P(=O)O$R^B$—, —C(=O)—, —C(=S)—, —C(=O)O—, —OC(=O)—, —C(=NR$^B$)—, —C=NR$^B$—, —NR$^B$C(=O)—, —C(=O)NR$^B$—, —NR$^B$C(=S)— and —C(=S)NR$^B$—, wherein R$^A$ may also be H;

wherein, if said alkyl, alkenyl, alkynyl or aryl substituent is further substituted, the substituents of said substituents, and said R$^B$, if present, may be selected from halogen, —F, —Cl, —Br, —I, —NO$_2$, —CN, —OH, —CF$_3$, substituted or unsubstituted C1-C8 alkyl, C2-C8 alkenyl, C2-C8 alkynyl, C5 to C8 aryl, wherein any hydrocarbon group of said substituent may be replaced by any one selected from the group of —O—, —S—, —S(=O)—, —S(=O)$_2$—, —Si—, —Ge—, —N=, —C(=O)—, —C(=S)—, —C(=O)O—, —OC(=O)—, wherein R$^B$ may also be H. Further substituents of said further substituents are preferably selected from halogen, —CN and C1 to C4 alkyl, C2-C4 alkenyl and C2-C4 alkynyl, wherein any available hydrogen of said alkyl, alkenyl or alkynyl may be substituted by halogen.

Preferably, said substituted or unsubstituted C1-C50 alkyl, C2-C50 alkenyl, C2-C50 alkynyl, and C4 or C5 to C50 aryl are substituted or unsubstituted C1-C20 alkyl, C2-C20 alkenyl, C2-C20 alkynyl, and C4 to C20 aryl.

For the purpose of the present specification, any alkyl, alkenyl or alkynyl specified herein may be linear, branched and/or cyclic. In this case, the alkyl, alkenyl and alkynyl has three or more carbons. Any aryl having 4 or 5 carbons has an appropriate number of ring heteroatoms in order to provide an aromatic substituent ring. The expression "aryl" thus encompasses heteroaryls. According to an embodiment, an aryl is selected from heteroaryls and from aryls lacking any heteroatom.

Preferably, R$^A$ is selected from H, C1-C10 alkyl, C2-C10 alkenyl, C2-C10 alkynyl, C4-C10 aryl, —CN, wherein said alkyl, alkenyl, alkynyl and/or aryl may be further substituted with —CN, C1-C4 alkyl (partially or totally halogenated) and halogen. More preferably, R$^A$ is selected from H, —CN, C1-C5 alkyl, C2-C5 alkenyl, C2-C5 alkynyl, C4 to C6 aryl, which may be further substituted by —CN or halogen.

Preferably, R$^B$ is selected from H, H, C1-C5 alkyl, C2-C5 alkenyl, C2-C5 alkynyl, C4-C6 aryl, —CN, wherein said alkyl, alkenyl, alkynyl and/or aryl may be further substituted with —CN, C1-C4 alkyl (partially or totally halogenated) and halogen. More preferably, R$^B$ is selected from H, —CN, C1-C4 alkyl, C2-C4 alkenyl, C2-C4 alkynyl, C4 to C6 aryl, which may be further substituted by —CN or halogen.

According to an embodiment, any one of R$_A$, R$_B$ and R$_C$ is independently selected from substituents as defined for R$^A$, preferably R$^B$ as defined elsewhere in this specification, including preferred embodiments of said substituents R$^A$, preferably R$^B$.

According to a preferred embodiment, any one of R$^1$, R$^2$, R$^3$, R$^4$, R$^5$, R$^6$, R$^7$, and R$^8$, in as far as present on the compounds (1) to (63) (or on the group of compounds (1) to (42) according to the embodiment specified above), may independently be selected from H, halogen, and from hydrocarbons comprising 1 to 20 carbons and 0 to 10 heteroatoms; preferably from H and C1 to C10 hydrocarbons comprising 0 to 10 heteroatoms; more preferably from H and C1 to C5 hydrocarbons comprising 0 to 5 heteroatoms, under the proviso mentioned elsewhere in this specification.

According to a preferred embodiment, any one of R$_1$, R$_2$, R$_3$, R$_4$, R$_5$, and R$_6$, in as far as present on the substituents (A-1) to (G-2) above (or on the group of substituents (A-3) to (G-2) according to the embodiment specified above), and/or on ligands, such as Xb, may be independently selected from H, halogen and from hydrocarbons comprising 1 to 20 carbons and 0 to 10 heteroatoms or from hydrocarbons comprising 1 to 15 carbons and 0 to 10 heteroatoms; preferably from H and C1 to C10 hydrocarbons comprising 0 to 10 heteroatoms; more from preferably H and C1 to C5 hydrocarbons comprising 0 to 5 heteroatoms, and if applicable under the proviso mentioned elsewhere in this specification.

According to an embodiment, any one of R$^1$, R$^2$, R$^3$, R$^4$, R$^5$, R$^6$, R$^7$, R$^8$, R$_1$, R$_2$, R$_3$, R$_4$, R$_5$, R$_6$, R' and R", if applicable, is selected independently from H, and from C1-C10 alkyls, C2-C10 alkenyls C2-C10 alkynyls, and C5-C12 aryls (preferably C6-C12 aryls), wherein in said alkyls, alkenyls, alkynyls and aryls one, several or all available hydrogen may be replaced by halogen and/or by —CN, wherein any one of said R$^1$ to R$^8$ and R$_1$ to R$_6$ may further be selected from halogen and from —C≡N (—CN). Said aryl may or may not be further substituted by C1-C4 alkyl, halogen and —CN.

According to an embodiment, any one of R$^1$, R$^2$, R$^3$, R$^4$, R$^5$, R$^6$, R$^7$, R$^8$, R$_1$, R$_2$, R$_3$, R$_4$, R$_5$, R$_6$, R' and R", in as far as present, is selected independently from the substituents of formulae (A-1) to (G-2) or from the group of substituents (A-3) to (G-2) as defined above (this preferably applies only R$^1$-R$^8$, as (A-1) to (G-2) examples of substituents R$^1$-R$^8$), H, and from C1-C6 alkyls, C2-C6 alkenyls C2-C6 alkynyls, and C6-C10 aryls, wherein in said alkyls, alkenyls, alkynyls and aryls one, several or all available hydrogen may be replaced by halogen and/or —CN, wherein any one of said R$^1$ to R$^8$ and R$_1$ to R$_6$ may further be selected from halogen and from —C≡N (—CN). Said aryl may or may not be further substituted by C1-C4 alkyl, halogen and —CN.

According to an embodiment, any one of R$^1$, R$^2$, R$^3$, R$^4$, R$^5$, R$^6$, R$^7$, R$^8$, R$_1$, R$_2$, R$_3$, R$_4$, R$_5$, R$_6$, R' and R", in as far as present, is selected independently, from the substituents of formulae (A-1) to (G-2) or from the group of substituents (A-3) to (G-2) as defined above (preferably in the case of R$^1$-R$^8$, see above), H, and from C1-C6, preferably C1-C4, more preferably C1-C3 alkyl, said alkyl, being optionally partially or totally substituted by halogen, wherein any one of said R$^1$ to R$^8$ and R$_1$ to R$_6$ may further be selected from halogen and from —C≡N.

According to an embodiment, any one of R$^1$, R$^2$, R$^3$, R$^4$, R$^5$, R$^6$, R$^7$, R$^8$, R$_1$, R$_2$, R$_3$, R$_4$, R$_5$, R$_6$, in as far as present, is selected, independently, from the substituents of formulae (A-1) to (G-2) or from the group of substituents (A-3) to (G-2) as defined above, (preferably in case of R$^1$-R$^8$, see above), H, halogen, —CN, and from C1-C6, preferably C1-C4 and most preferably C1-C3 alkyl, said alkyl being possibly substituted by halogen. According to an embodiment, R$_7$-R$_9$ are not —CN.

According to an embodiment, R' and R" are selected independently from H and from C1-C6 linear branched or cyclic alkyl, said alkyl being possibly and optionally partially or totally substituted by halogen.

According to an embodiment, R$^1$, R$^2$, R$^3$, R$^4$, R$^5$, R$^6$, R$^7$, R$^8$ (if applicable, with the proviso related to compounds (1) to (5) specified elsewhere in this specification), in as far as present, are selected independently from H, halogen, —CN, and from C1-C6 alkyl and alkenyl, said alkyl and alkenyl, wherein any available hydrogen of said alkyl and alkenyl may or may not be replaced by halogen and/or —CN. Preferably, R$^1$, R$^2$, R$^3$, R$^4$, R$^5$, R$^6$, R$^7$, R$^8$ (if applicable, with the proviso related to compounds (1) to (5) specified elsewhere in this specification), in as far as present, are selected independently from H, halogen, —CN, and from C1-C4 alkyl, said alkyl being optionally totally or partially halogenated. Preferably, R$^1$, R$^2$, R$^3$, R$^4$, R$^5$, R$^6$, R$^7$, R$^8$, in as far as present, are selected independently from H, halogen, —CN, —CF3 and C1-C3 alkyl.

According to an embodiment, $R_1$, $R_2$, $R_3$, $R_4$, $R_5$, $R_6$, in as far as present, are selected independently from H, halogen, —CN, and from C1-C6 alkyl and alkenyl, wherein any available hydrogen of said alkyl and alkenyl may or may not be replaced by halogen and/or —CN. Preferably, $R_1$, $R_2$, $R_3$, $R_4$, $R_5$, $R_6$, in as far as present, are selected independently from H, halogen, —CN, and from C1-C4 alkyl, said alkyl being optionally totally or partially halogenated. Preferably, $R_1$, $R_2$, $R_3$, $R_4$, $R_5$, $R_6$, in as far as present, are selected independently from H, halogen, —CN, —CF$_3$ and C1-C4 alkyl. According to an embodiment, $R_7$-$R_9$ are preferably not selected from halogen and/or CN.

Substituents $R^1$, $R^2$, $R^3$, $R^4$, $R^5$, $R^6$, $R^7$, $R^8$, $R_1$, $R_2$, $R_3$, $R_4$, $R_5$, $R_6$, other than H are suitable to adjust the oxidation potential of the metal complex. Without wishing to be bound by theory, it is believed that such substituents can help obtaining electrochemical devices with higher $V_{OC}$ values, and to adjust the oxidation potential of the redox couple to the properties of the dye.

According to an embodiment of the complex of the invention, at least one of said ligands La (L1, . . . , Ln) is, independently, selected from compounds of formulae (1-2) to (3-2) below:

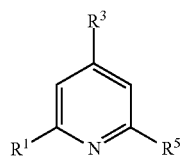

(1-2)

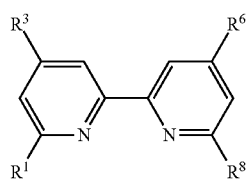

(2-2)

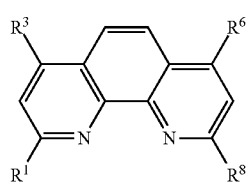

(3-2)

wherein at least one substituent of said compound, selected from substituents $R^1$, $R^3$, $R^5$, $R^6$, and $R^8$, in as far as present, is selected from the substituents (A-1) to (G-2) or from the group of substituents (A-3) to (G-2) as defined elsewhere in this specification.

According to an embodiment, of the complex of the invention, at least one of said ligands La (L1, . . . , Ln) is, independently, selected from compounds of formulae (1-3) to (3-3) below:

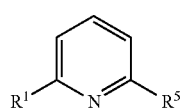

(1-3)

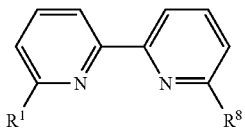

(2-3)

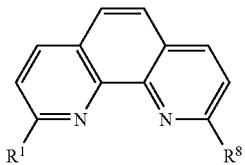

(3-3)

wherein at least one substituent of said compound, selected from substituents $R^1$, $R^5$, and $R^8$, in as far as present, is selected from the substituents (A-1) to (G-2) or from the group of substituents (A-3) to (G-2) as defined elsewhere in this specification.

The complex of any one of the preceding claims, wherein at least one ligand La is selected from the compounds of formula (1-5) to (3-5) below:

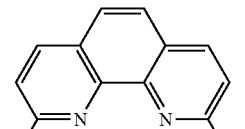

(1-4)

(2-4)

(3-4)

wherein:
$R^1$ is selected from the substituents (A-1) to (G-2) or from the group of substituents (A-3) to (G-2) as specified elsewhere in this specification.

In accordance with the present invention, it was surprisingly found that the presence of a second heteroatom in the ring binding to the metal atom of the complex of the invention is suitable to positively affect the properties and suitability of the complex of the invention as a redox couple.

Therefore, ligands (e.g. La) comprising a ring with at least two ring heteroatoms are particularly preferred. According to this embodiment ("embodiment A"), the complex of the present invention comprises one or more ligands selected from: (10)-(42), (50)-(63), and, more preferably, from complexes comprising the ligands (1), (2), (3), (4), (1-2), (2-2), (3-2), (1-3), (2-3), (3-3), (1-4), (2-4), (3-4), in as far as these compounds comprise at least one substituent selected from: (B-1) to (B-24), (C-17) to (C-27), (D-1) to (D-3), (F-1) to (F-10), (G-1) and (G-2).

According to another embodiment ("embodiment A'"), ligands (e.g. La) comprising a ring with exactly two ring heteroatoms are particularly preferred.

According to an embodiment ("embodiment B"), ligands (e.g. La) comprising at least two adjacent ring heteroatoms are particularly preferred. Accordingly, the complex of the present invention comprises one or more ligands selected from: (13), (15), (16), (17), (18), (23) to (34), (40) to (42), (50) to (54), (60) to (63), and, more preferably, from complexes comprising the ligands (1), (2), (3), (4), (1-2), (2-2), (3-2), (1-3), (2-3), (3-3), (1-4), (2-4), (3-4), in as far as these compounds comprise at least one substituent selected from (B-1), (B-3), (B-6), (B-8), (B-13), (B-24), (B-25), (B-27), (C-1) to (C-8), (C9) to (C-16), (C-18) to (C-27), (D-1) to D-3), (F-1), F-3), (F-4), (F-6), (G-1), (G-2).

According to an embodiment ("embodiment C"), ligands (e.g. La) comprising a five-membered heteroring are particularly preferred. Accordingly, the complex of the present invention comprises one or more ligands selected from: (6) to (34), (43) to (63), and, more preferably, from complexes comprising the ligands (1), (2), (3), (4), (1-2), (2-2), (3-2), (1-3), (2-3), (3-3), (1-4), (2-4), (3-4), in as far as these compounds comprise at least one substituent selected from (A-1) to (A-6), (B-1) to (B-18), (C-1) to (C-8), (D-1) to (D-3), (E-1) to (E-3), (F-1) to (F-10), (G-1) and (G-2).

According to an embodiment ("embodiment D"), ligands (e.g. La) comprising a five-membered heteroring that is not fused to any further ring are particularly preferred. Accordingly, the complex of the present invention comprises one or more ligands selected from: (6) to (34), and, more preferably, from complexes comprising the ligands (1), (2), (3), (4), (1-2), (2-2), (3-2), (1-3), (2-3), (3-3), (1-4), (2-4), (3-4), in as far as these compounds comprise at least one substituent selected from (A-1) to (A-6), (B-1) to (B-18), (C-1) to (C-8), (D-1) and to (D-3).

According to an embodiment ("embodiment E"), ligands (e.g. La) comprising a five- or six-membered heteroring having aromatic properties (being aromatic) are particularly preferred. Accordingly, the complex of the present invention comprises one or more ligands selected from: (6), (7), (10) to (12), (15), (16), (19), (21), (23) to (28), (31) to (34), (35) to (36), (39), (42), (43) to (48), (50) to (53), (55) to (56), (58) to (60) and (62), and, more preferably, from complexes comprising the ligands (1), (2), (3), (4), (1-2), (2-2), (3-2), (1-3), (2-3), (3-3), (1-4), (2-4), (3-4), in as far as these compounds comprise at least one substituent selected from: (A-3) to (G-2).

According to an embodiment ("embodiment F"), the invention provides complexes comprising one or more bi- or tridentate ligands (e.g. La) containing at least one pyridine ring and at least one substituent, wherein said substituent is bound by way of a carbon-nitrogen bond to said pyridine ring. Accordingly, the present invention provides complexes comprising one or more ligands of formula (1), (2), (3), (4), (1-2), (2-2), (3-2), (1-3), (2-3), (3-3), (1-4), (2-4), and/or (3-4), wherein said ligands contain one or more substituents selected from: (A-3), (B-8) to (B-10), (B-23), (B-24), (C-4) to (C-6), (C-9) to (C-16), (C-23), (C-26), (D-2), (E-3), (F-3), (F-4), (F-7), (G-1).

According to an embodiment ("embodiment G"), the complex of the invention comprises one or more bi- or tridentate ligands (e.g. La) comprising at least one pyridine ring and at least one substituent selected from substituents (A-1) to (A-6), (B-1) to (B-27), (C-1) to (C-27), (D-1) to (D-3), (E-1) to (E-3), (F-1) to (F-19) and (G-1) to (G-2).

The above embodiments A to G may be combined with each in as far as possible in order to provide more specifically preferred embodiments. For example, according to a preferred embodiment, the complex comprise a ligand selected from compounds that meets the definition of two or more of embodiments A to G (the cut-set, overlap or intersection n). For example, the complex of the invention comprises a ligand selected from ligands comprising a five-membered heteroring and which ligand has, at the same time, aromatic properties (the overlap of embodiments C and E).

Further particularly preferred embodiments are the overlap of embodiments A and B; A and C; A and D; A and E; A and F. Further preferred embodiments are provided by the overlap of embodiments B and C; B and E; B and F, B and G; B and F. Further preferred embodiments are the overlap of embodiments C and D; C and E; C and F; C and G. Further preferred embodiments are the overlap of embodiments D and E; D and F; D and G. Further preferred embodiments are the overlap of embodiments E and F; E and G. A further preferred embodiment is the overlap of embodiments F and G.

Further preferred embodiments are provided by the overlap of three embodiments selected from embodiments A to G. Such specifically preferred embodiments are provided by the following overlaps of embodiments: A,BandC; A, B and D; A, B, and E; A, B and F; A, B and G; A, C and D; A, C and E; A, C and F; A, C and G; A, D and E; A, D and F; A, D and G; A, E and F; A, E and F; B, C and D; B, C and E; B, C and F; B, C and G; B, D, and E; B, D and F; B, D and G; B, E and F; B, E and G; B, F and G; C, D and E; C, D and F; C, D and G; C, E and F; C, E and G; C, F and G; D, E and F; D, F and G.

For example, the overlap of embodiments A, B and C (underlined above) relates to complexes of the invention comprising a ligand having a five-membered ring (C) containing at least two (A) adjacent (B) heteroatoms. These ligands are those represented by compounds (13), (15) to (18), (23) to (34), (50) to (54), (60) to (63), and the compounds of formulae (1) to (5), (1-2), (2-2), (3-2), (1-3), (2-3), (3-3), (1-4), (2-4), (3-4), in as far as these latter compounds comprise at least one substituent selected from the substituents (B-1), (B-4), (B-6), (B-8), (B-13), (C-1) to (C-8), (D-1) to (D3), (F-1), (F-3), (F-4), (F-6), (G-1), (G-2).

Further preferred embodiments are provided by the overlap of four embodiments selected from embodiments A to G. Such specifically preferred embodiments are provided by the following overlaps of embodiments: A, B, C, and D; A, B, C, and E; A, B, C, and F; A,B,CandG; A, B, D, and E; A, B, D and F; A, B, D and G; A, C, D and E; A, C, D and F; A, C, D and G; A, C, E and F; A, C, E and G; A, D, E and F; A, D, E and G; A, E, F and G; B, C, D and E; B, C, D and F; B, C, D and G; B, C, E and F; B, C, E and G; B, C, F and G; B, D, E and F; B, D, E and G; B, E, F and G; C, D, E and F; C, D, E and G; C, D, F and G; D, E, F and G.

For example, an overlap of embodiments, A, B, C, and G (underlined above), relates to complexes of the invention comprising a bi- or tridentate ligand (La) comprising at least one pyridine ring (G), and a substituent having a five-membered ring (C) containing at least two (A) adjacent (B) heteroatoms. These ligands are those represented by compounds of formulae (1) to (5), (1-2), (2-2), (3-2), (1-3), (2-3), (3-3), (1-4), (2-4), (3-4), in as far as these latter compounds comprise at least one substituent selected from the substituents (B-1), (B-4), (B-6), (B-8), (B-13), (C-1) to (C-8), (D-1) to (D3), (F-1), (F-3), (F-4), (F-6), (G-1), (G-2).

In the embodiments and the preferred, combined or particular embodiments above, embodiment A may be replaced by embodiment A', resulting in the corresponding overlaps in which a ring with exactly two ring heteroatoms is present.

It is further noted that heteroatoms are as defined above, but nitrogen being the preferred ring-heteroatom. According to an embodiment, when there are exactly two or more than two ring-heteroatoms, said heteroatoms are preferably nitrogen atoms.

According to an embodiment, the complex of the invention comprises at least one ligand (La) selected from the compounds of any one of formula (1), (2), (3), (1-2), (2-2), (3-2), (1-3), (2-3), (3-3), (1-4), (2-4), (3-4), said compound being substituted with one, or, if applicable, two or three substituents, of formulae B-8, the other substituents being selected as specified above, but preferably from H, halogen, —CN, —CF$_3$, and C1-C4 alkyls, C2-C4 alkenyls and C2-C4 alkynyls, wherein in said alkyls, alkenyls and alkynyls one, several or all available hydrogen may be replaced by halogen.

According to an embodiment, the complex of the present invention (e.g. the complex of formula (I)) comprises at least one ligand (e.g. La) selected from the ligands of formulae (64), (65), (66), and (67) below:

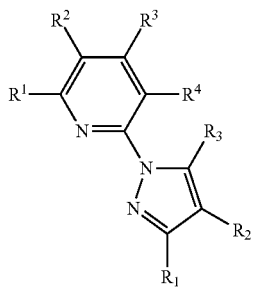

(64)

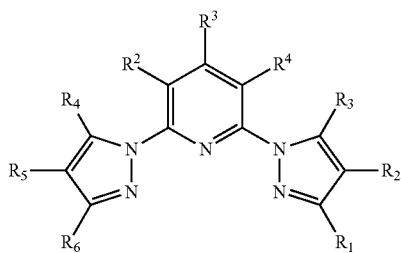

(65)

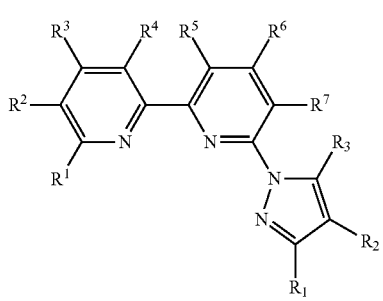

(66)

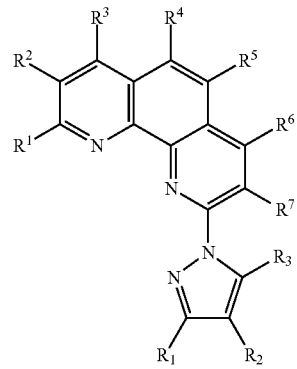

(67)

wherein $R_1$, $R_2$, $R_3$, $R_4$, $R_5$, $R_6$, $R_7$, in as far as applicable, and $R^1$, $R^2$, $R^3$, $R^4$, $R^5$, $R^6$, in as far as applicable, are as defined elsewhere in this specification, in particular according to the preferred embodiments.

Preferably, $R^1$, $R^2$, $R^3$, $R^4$, $R^5$, $R^6$, $R^7$, in as far as applicable, and $R_1$, $R_2$, $R_3$, $R_4$, $R_5$, $R_6$, in as far as applicable, in any one of compounds (64), (65), (66), and (67), is preferably selected from H, halogen, —CN, —CF$_3$, C1-C4 alkyls, C2-C4 alkenyls and C2-C4 alkynyls, wherein in said alkyls, alkenyls and alkynyls one, several or all available hydrogen may be replaced by halogen. According to an embodiment, $R^1$, $R^2$, $R^3$, $R^4$, $R^5$, $R^6$, $R^7$ (in as far as applicable) are all H, substituents $R_1$, $R_2$, $R_3$, $R_4$, $R_5$, $R_6$ (in as far as applicable), are as defined above or elsewhere in this specification, but preferably selected from H, —CN, and —CF$_3$.

According to an embodiment, at least one, at least two, in case of bidentate ligands, three ligands La is/are selected independently from the compounds shown in FIGS. 8, 9, 10, 11, 12, 13, 14, and/or 15. Accordingly, one, two or more ligands La may be independently selected from any one of ligands H-1 to H-31, J-1 to J-26, K-1 to K-33, L-1 to L-4, M-1 to M-15, N-1 to N-20, P-1 to P16, Q-1 to Q-63.

According to an embodiment, in compounds H-1 to H-31, J-1 to J-26, K-1 to K-33, L1 to L4, Q-1 to Q-26, Q-43 to Q-51, any one, more than one or all available hydrogen may independently be replaced by a substituent other than H as defined above for $R^1$ to $R^8$, and/or $R_1$ to $R_7$, as well as the preferred embodiments of $R^1$ to $R^8$ and $R_1$ to $R_6$ that are other than H. It is noted that in the other exemplary ligands (M-1 to M-15, N-1 to N-20, P-1 to P-16, Q-27 to Q-42 and Q-52 to Q-63) shown in the figures, substituents replacing available hydrogens are already present, these latter exemplary ligands thus form specific examples of ligands comprising such hydrogen replacing substituents.

Furthermore, in sever of the ligands shown in FIGS. 8 to 15, methyl substituents on nitrogen atoms corresponding to R' and R" as defined elsewhere in this specification are present (for example, H-2, H-4, H-6, H-8, etc). These N-methyl substituents may, according to an embodiment, be replaced by other substituents as defined for R' and R" elsewhere in this specification, in particular above.

According to an embodiment, in compounds H-1 to H-31, J-1 to J-26, K-1 to K-33, L1 to L4, Q-1 to Q-26, Q-43 to Q-51, any one, more than one or all available hydrogen may independently be replaced by —F, —Cl, —Br, —I, (halogen), —NO$_2$, —CN, —OH, —CF$_3$, substituted or unsubstituted C1-C50 alkyl, C2-C50 alkenyl, C2-C50 alkynyl, and C5 to C50 aryl as defined above for $R^1$ to $R^8$, and/or $R_1$, to $R_6$, as well as the preferred embodiments of $R^1$ to $R^8$, and $R_1$ to $R_6$ that are other than H.

In particular in any ligand La selected from compounds H-1 to H-31, J-1 to J-26, K-1 to K-33, L1 to L4, Q-1 to Q-26, Q-43 to Q-51, any one, more than one or all available hydrogen may independently be replaced by halogen, —CN, C1-C6 alkyls, C2-C6 alkenyls C2-C6 alkynyls, and C6-C10 aryls, wherein in said alkyls, alkenyls, alkynyls and aryls one, several or all available hydrogen may be replaced by halogen, —CN and —CF$_3$.

More preferably, in any ligand La selected from compounds H-1 to H-31, J-1 to J-26, K-1 to K-33, L1 to L4, Q-1 to Q-26, Q-43 to Q-51, any one, more than one or all available hydrogen may independently be replaced by halogen, —CN, C1-C4 alkyl, wherein in said alkyl one, several or all available hydrogen may be replaced by halogen, —CN and —CF$_3$.

Below, further preferred ligands La, in particular in the complex of the device comprising [B(CN)$_4$]$^-$ in the charge transport layer, are discussed below.

According to an embodiment, any one of said ligands La is independently selected from any one of the compounds of formula (1), (2), (3), (6), (7), (10), (11), (12), (15), (16), (23), (24), (25), (26), (27), (28), (29), (30), (31), (32), (33), (34), (35), (36), (37), (39), (40), (41), (42), as shown above, and of formula (68) below

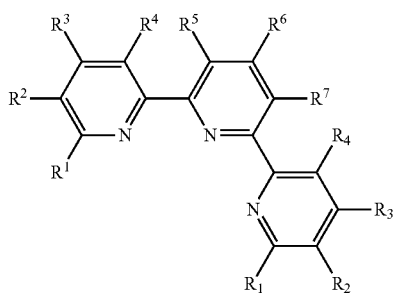

(68)

wherein any one of $R^1$, $R^2$, $R^3$, $R^4$, $R^5$, $R^6$, $R^7$, $R^8$, $R_1$, $R_2$, $R_3$, $R_4$, $R_5$, and $R_6$, in as far as present/applicable, is independently selected from H, from hydrocarbons comprising 1 to 30 carbons and 0 to 20 heteroatoms, halogen, (—F, —Cl, —Br, —I), —NO$_2$, —NH$_2$, and —OH; wherein R' and R", if applicable, are independently selected from H and substituents —CR$_A$R$_B$R$_C$, wherein R$_A$, R$_B$, and R$_C$ are independently selected from H and from hydrocarbons comprising 1 to 30 carbons and 0 to 20 heteroatoms, halogen, (—F, —Cl, —Br, —I), and wherein R$_A$ may also be selected from —NO$_2$, —NH$_2$ and —OH if R$_B$ and R$_C$ are not halogen, —NO$_2$, —NH$_2$ or —OH.

According to an embodiment of the device, any one of $R^1$, $R^2$, $R^3$, $R^4$, $R^5$, $R^6$, $R^7$, $R^8$, $R_1$, $R_2$, $R_3$, $R_4$, $R_5$, and $R_6$, in as far as present/applicable, is independently selected from H, from hydrocarbons comprising 1 to 30 carbons and 0 to 20 heteroatoms, halogen, (—F, —Cl, —Br, —I), —NO$_2$, —NH$_2$, and —OH; wherein R' and R", if applicable, are independently selected from H and substituents —CR$_A$R$_B$R$_C$, wherein R$_A$, R$_B$, and R$_C$ are independently selected from H and from hydrocarbons comprising 1 to 30 carbons and 0 to 20 heteroatoms, halogen, (—F, —Cl, —Br, —I), and wherein R$_A$ may also be selected from —NO$_2$, —NH$_2$ and —OH if R$_B$ and R$_C$ are not halogen, —NO$_2$, —NH$_2$ or —OH.

According to an embodiment of the device, any one of $R^1$, $R^2$, $R^3$, $R^4$, $R^5$, $R^6$, $R^7$, $R^8$, $R_1$, $R_2$, $R_3$, $R_4$, $R_5$, and $R_6$, in as far as present, is independently selected from H, halogen, —NO$_2$, —OH, —NH$_2$, hydrocarbons comprising 1-30 carbons and 0-20 heteroatoms, and from the substituents of formula (A-3), (A-5), (A-6), (B-5), (B-6), (B-8), (B-9), (B-10), (B-11), (B-12), (B-13), (B-14), (B-15), (B-17), (B-21), (B-22), (B-24), (B-25), (B-26), (B-27), (C-2), (C-3), (C-4), (-5), (C-6), (C-7), (C-8), (C-9), (C-10), (C-11), (C-13), (C-14), (C-15), (C-16), (C-12), (C-17), (C-18), (C-19), (C-20), (C-21), (C-24), (C-25), (C-26), (C-27), (D-1), (D-2), (D-3), (E-1), (E-2), (E-3), (F-1), (F-2), (F-3), (F-4), (F-5), (F-6), (F-7), (F-9), (F-10), (G-1), (G-2), as defined above, (the "group of substituents (A-3) to (G-2)"); wherein the dotted line represents the bond connecting the substituent of (A-1) to (G-2) on the compound of formula (1)-(68) as shown above; and, substituents $R_1$, $R_2$, $R_3$, $R_4$, $R_5$, and $R_6$, in as far as present, are independently selected from H, hydrocarbons comprising 1 to 20 carbons and 0 to 20 heteroatoms, halogen, (—F, —Cl, —Br, —I), and —NO$_2$. According to an embodiment, at least one of said $R^{1-8}$ and $R_{1-6}$, in as far as present, is not H.

According to an embodiment of the device, any one of said La is independently selected from any one of compounds of formula (2), (3) as shown above and compounds of formula (68) as above, and of compounds (64) and (66) as shown below:

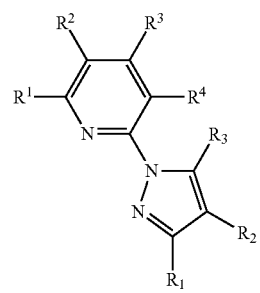

(64)

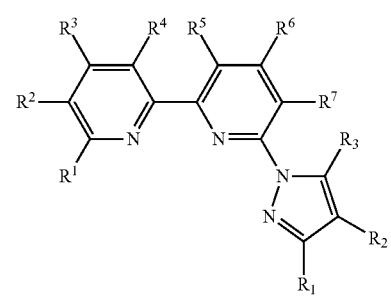

(66)

wherein any one of $R^1$, $R^2$, $R^3$, $R^4$, $R^5$, $R^6$, $R^7$, $R^8$, $R_1$, $R_2$, $R_3$, $R_4$, $R_5$, and $R_6$, in as far as present/applicable, is independently selected from H and from hydrocarbons comprising 1 to 20 carbons and 0 to 15 heteroatoms, halogen, (—F, —Cl, —Br, —I), —NO$_2$, —NH2 and —OH.

According to an embodiment of the device, ligands La are independently selected from ligands H-1 to H-31, J-1 to J-26, K-1 to K-33, L-1 to L-4, M-1 to M-15, N-1 to N-20, P-1 to P16, Q-1 to Q-63 shown in FIGS. 8-1 to 15-4, and their possible substituents.

According to an embodiment of the device, n is 3, b is 0 and/or wherein the ligands L1, L2, L3 are independently selected from compounds of formulae (2), (3) and (64), as defined elsewhere in this specification.

According to an embodiment of the device, n is 2, b is 0 or 1, and/or wherein L1 and L2 are selected independently from the compounds of formulae (68) and (66).

According to an embodiment, any one of $R^1$, $R^2$, $R^3$, $R^4$, $R^5$, $R^6$, $R^7$, $R^8$, and of $R_1$, $R_2$, $R_3$, $R_4$, $R_5$, and $R_6$, in as far as the respective substituent is present on the compounds (1), (2), (3), (6), (7), (10), (11), (12), (15), (16), (23), (24), (25), (26), (27), (28), (29), (30), (31), (32), (33), (34), (35), (36), (37), (39), (40), (41), (42), and (68) and their substituents, may thus be independently selected from H, halogen, $-NO_2$, $-OH$, $-NH_2$ and from hydrocarbons comprising 1 to 30 carbons and 0 to 20 heteroatoms (in the case of $R^1$-$R^8$) or from hydrocarbons comprising 1 to 20 carbons and 0 to 15 heteroatoms (in the case of $R_1$-$R_6$).

According to another embodiment, any one of $R^1$, $R^2$, $R^3$, $R^4$, $R^5$, $R^6$, $R^7$, $R^8$, and of $R_1$, $R_2$, $R_3$, $R_4$, $R_5$, and $R_6$, in as far as the respective substituent is present on the compounds (1), (2), (3), (6), (7), (10), (11), (12), (15), (16), (23), (24), (25), (26), (27), (28), (29), (30), (31), (32), (33), (34), (35), (36), (37), (39), (40), (41), (42), and their substituents, may thus be independently selected from H, halogen, $-NO_2$, $-OH$, $NH_2$ and from hydrocarbons comprising 1 to 20 carbons and 0 to 15 heteroatoms. Heteroatoms are as defined elsewhere in this specification.

According to an embodiment, $R^1$, $R^2$, $R^3$, $R^4$, $R^5$, $R^6$, $R^7$, and $R^8$, in as far as present, are selected independently from the group substituents of formulae (A-3) to (G-2), H, halogen, $-CN$, and from C1-C6 alkyl and alkenyl, wherein any available hydrogen of said alkyl and alkenyl may or may not be replaced by halogen and/or $-CN$. Preferably, $R^1$, $R^2$, $R^3$, $R^4$, $R^5$, $R^6$, $R^7$, and $R^8$, in as far as present, are selected independently from H, halogen, $-CN$, and from C1-C4 alkyl, said alkyl being optionally totally or partially halogenated. Preferably, $R^1$, $R^2$, $R^3$, $R^4$, $R^5$, $R^6$, $R^7$, and $R^8$ in as far as present, are selected independently from H, halogen, $-CN$, $-CF3$ and C1-C3 alkyl.

Other ligands of the complexes of the invention, in particular ligands Xb (X1, . . . , Xm) of the complex of formula (I), may, for example, be selected from: $H_2O$, $Cl^-$, $Br^-$, $I^-$, $CN^-$, $NCO^-$, $NCS^-$, $NCSe^-$, $NH_3$, CO, PR3 (R is independently selected from substituted and unsubstituted C6-C18, preferably C6-C12 aryl and/or aroxyl (for example phenyl or phenoxyl); substituted and unsubstituted C1-C18, preferably C1-10, more preferably C1-C4 alkyl and/or alkoxyl; imidazole, substituted imidazoles; pyridines, substituted pyridines; pyrazoles, substituted pyrazoles; triazoles; pyrazine; for example. Preferably, the ligands Xb (X1, . . . , Xm) are selected from $H_2O$, $Cl^-$, $Br^-$, $I^-$, $CN^-$, $NCO^-$, $NCS^-$, $NCSe^-$, $NH_3$, CO, and PR3 (R is as above, preferably independently selected from phenyl, phenoxyl, alkyl and alkoxyl).

According to a preferred embodiment, Xb is independently a co-ligand; such as $H_2O$, $Cl^-$, $Br^-$, $I^-$, $CN^-$, $NCO^-$, $NCS^-$, $NCSe^-$, $NH_3$, $NR_7R_8R_9$, and $PR_7R_8R_9$, wherein $R_7$, $R_8$, and $R_8$ are selected independently from substituted or unsubstituted alkyl, alkenyl, alkynyl and aryl. According to an embodiment, said alkyl, alkenyl and aryl is independently selected from substituted or unsubstituted C1-C20 alkyl, C2-C20 alkenyl, C2-C20 alkynyl, and C4 to C20 aryl as defined elsewhere in this specification, and preferred embodiments of alkyl, alkenyl, alkynyl and aryl as defined for $R^1$-$R^8$ and/or $R_1$-$R_6$ elsewhere in this specification. Furthermore, two or all three of $R_7$, $R_8$, and $R_9$ may be connected with each other so as to provide a cyclic or polycyclic ligand.

The ligands Xb may be absent. Preferably, the ligands Xb, in as far as present, is/are co-ligand(s) and/or spectator ligand(s). Preferably, any one ligand Xb is independently selected from monodentate ligands. Preferably, all ligands Xb, in as far as present, are monodentate ligands.

The present invention also relates to electrochemical or optoelectronic device comprising the complex of the invention. In general, electrochemical devices are devices comprising at least one electrode at which an oxido-reductive process takes place. In general, an electrochemical device is a device in which a chemical reaction takes place due to external voltage, or voltage is created due to a chemical reaction.

The complex of the invention is preferably used as a redox-couple, the oxidized and reduced counterparts of the complex forming a redox pair. The redox pair is preferably formed by two oxidation states of the metal atom in the complex. According to an embodiment, the redox-couple is preferably suitable for a monoelectronic redox process. For example, +I/+II or +II/+III or +III/+IV if M is Cobalt or +I/+II if M is Copper, just to mention some non-limiting possibilities.

The device of the invention may be a photo-electrochemical device, an optoelectronic device, an electrochemical battery, for example a lithium ion battery, a double layer capacitor, a light emitting device, an electrochromic or photo-electrochromic device, an electrochemical sensor, a biosensor, an electrochemical display and an electrochemical capacitor, for example a super capacitor. According to a preferred embodiment, the electrochemical device is a photoelectrical conversion device, in particular a solar cell.

The device of the invention is preferably a photovoltaic device.

According to an embodiment, the device of the invention is a photoelectric conversion device, preferably a dye-sensitized solar cell (DSSC) or photovoltaic cell. According to an embodiment, the device is a regenerative, dye-sensitized solar cell.

The electrochemical device of the invention is preferably a regenerative device.

According to an embodiment, the electrochemical and/or optoelectronic device of the invention comprises a first and a second electrode and, between said first and second electrode, a charge transport layer and/or intermediate layer. Said charge transport and/or intermediate layer preferably comprises the complex of the invention.

According to an embodiment, the intermediate and/or charge transport layer comprises an organic solvent and/or comprises one or more ionic liquids.

According to an embodiment, said charge transport and/or intermediate layer comprises one or more selected from: an organic solvent, one or more ionic liquids, an electronically conducting, hole or electron transporting material, and combinations thereof. According to a preferred, the charge transport layer is a solvent-based electrolyte.

According to an embodiment, said electrolyte or said intermediate layer comprises the metal complex according to the invention.

It is noted that, according to the knowledge of the present inventors, tetracyanoborate has been used as counter anion, which is stable compared to the hexa fluorophosphate anion. Also, the added tetracyanoborate anion is compatible with ionic liquids that contain the same anion as part of an ionic liquid electrolyte to electrochemical device, as reported, for example, in WO2007/093961 A1, where dye-sensitized solar cells using the iodide, triiodide redox couple are disclosed. The use of salts comprising the metal-based redox couple together with tetracyanoborate in devices containing solvents allows, surprisingly, to conveniently and efficiently use tetratcyanoborate not only in ionic liquids but also in solvent-based devices, where this compound had not yet been used so far.

According to an embodiment, the first electrode comprises at least one selected from the group of a photo electrode, any anode and a cathode (for example in certain photoelectrochromic devices). The second electrode is preferably a counter electrode. Between said first (photo, etc) electrode and said counter electrode there is preferably said intermediate and/or charge transport layer. Said intermediate/charge transport layer preferably comprises the complex of the present invention. Said first electrode, intermediate layer and second electrode are preferably connected in series.

According to an embodiment, said first electrode is a semiconductor electrode comprising a surface facing the charge transport layer of the device, wherein on said surface, there is adsorbed a dye so as to form a layer on said surface, wherein said dye is preferably selected from dyes carrying no charge or carrying a positive charge when being adsorbed on said surface. This is the case, for example, with dye-sensitized solar cells and electrochromic or photoelectrochromic devices, such as disclosed, for example, in U.S. Pat. Nos. 6,426,827 and 6,067,184.

The device of the invention may further comprise one or more substrate layers, for example supporting one of the electrodes, preferably the photo electrode. The substrate layer may be made from plastic or from glass. In flexible devices, the substrate is preferably made from plastic.

The electrochemical/optoelectronic device of the present invention generally has two conductive layers, wherein a first conductive layer is required for removing the electrons generated from the device, generally at the first electrode, and a second conductive layer for supplying new electrons, or, in other words, removing holes, generally at the second electrode. The second conductive layer is generally part of the counter electrode and may be already part of a substrate layer, as is the case, for example with ITO (indium tin oxide)-coated plastic or glass, where the transparent ITO is coated on the plastic or glass and makes the later electrically conductive.

The device of the present invention generally comprises a counter electrode (a second electrode), which faces the intermediate or electrolyte layer towards the inside of the device, and the substrate on the outside of the cell, if such substrate is present. The counter electrode generally comprises a catalytically active material, suitable to provide electrons and/or fill holes towards the inside of the device. The counter electrode may thus comprises materials selected from material selected from Pt, Au, Ni, Cu, Ag, In, Ru, Pd, Rh, Ir, Os, C, conductive polymer and a combination of two or more of the aforementioned, for example. Conductive polymers may be selected from polymers comprising polyaniline, polypyrrole, polythiophene, polybenzene and acetylene, for example.

In dye sensitized solar cells, at least part of the photo electrode contains a sensitizer layer towards the inside of the cell/device, thereby forming a light absorption layer, which thus comprises at least two separate layers, namely a porous semiconductor layer and, absorbed thereon, a layer of sensitising dyes. The porous semiconductor layer may be produced by processes described in the art (B. O'Reagan and M. Grätzel, Nature, 1991, 353, 373) from semiconductor nanoparticles, in particular nanocrystalline particles. Such particles generally have a mean diameter of about 0-50 nm, for example 5-50 nm. Such nanoparticles may be made from a material selected from the group of Si, $TiO_2$, $SnO_2$, ZnO, $WO_3$, $Nb_2O_5$ and $TiSrO_3$, for example.

The dye layer comprises, besides optional co-adsorbed compounds, such as those disclosed in WO2004/097871A1, for example, at least one dye or sensitizer, or a combination of two or more different sensitizers. For example, the dye may be an organo-metallic compound. Examples for organometallic compounds encompass ruthenium dyes, as they are currently used in such devices. Suitable ruthenium dyes are disclosed, for example, in WO2006/010290.

The dye layer may comprise organic sensitizers. For example, the device may be free of any sensitizer using ruthenium or another noble metal.

According to an embodiment, said dye, when adsorbed on said surface of a semiconductor electrode, lacks any negatively charged, free group. For example, the dye lacks any non-anchored, negatively charged anchoring group. Anchoring groups may be selected, for example, from —$COO^-$, —$PO_3H^-$, —$PO_4H^-$, —$SO_3H^-$, $SO_4H$—, —$CONHOH^-$, just to mention a few. Such negatively charged anchoring groups are generally provided on the dye so as to anchor the latter to the semiconductor electrode. Frequently, a dye comprises two or even more anchoring groups, thereby ensuring tight binding of the dye to the semiconductor electrode.

Without wishing to be bound by theory, the present inventors envisage that in many circumstances, there may be groups that are on the sensitizer which is anchored to the semiconductor electrode. The groups can thus provide a negative charge to the anchored dye. This in turn may cause attraction between positively charged redox active species and the dye groups. Without wishing to be bound by theory, the present inventors envisage that this is why the dye-sensitized solar cells disclosed in WO 03/038508 had a poor performance.

Therefore, according to an embodiment, the dye preferably comprises no negatively charged groups per dye molecule. According to an embodiment, this also applies to organometallic compounds, ruthenium dyes and the like, such as disclosed for example, in EP0613466, EP0758337, EP 0983282, EP 1622178, WO2006/038823. Therefore, the dye may be synthesized to have anchoring groups but without negative charge on the sensitizer as from the beginning. A further possibility is to ensure that all or an important majority anchoring groups are bound to the semiconductor surface in case the dye has two or more negatively charged anchoring groups. The term "negatively charged anchoring group" preferably but not necessarily also encompasses anchoring groups that may become negative due to deprotonation. The anchoring group is negatively charged in case it is not bound and, at the same time, present in deprotonated form.

The method of the present invention preferably comprises the step of adding to said charge transport layer a salt comprising tetracyanoborate ($[B(CN)_4]^-$) and a cationic metal complex of formula I. In particular, tetracyanoborate is advantageously added to electrochemical devices, conveniently as a salt with the complex functioning as a redox-couple. In this way, not only are (other) anions avoided, which have no function and/or which may even unfavorably affect performance or stability of the device, but, in contrast, addition of a compound is achieved in an economic, practical and efficient way, which compound improves stability of such devices, including devices, in which tetracyanoborate was not used and/or could not be added without a further step.

The intermediate and/or charge transport layer of the device of the present invention preferably has the general purpose of mediating the regeneration of electrons. For example in the dye of a DSSC, electrons were removed due to radiation and need to be regenerated. The electrons are generally provided by the counter electrode, and the intermediate layer thus mediates the transport of electrons from the counter electrode to the dye, or of holes from the dye to the counter electrode. The transport of electrons and/or holes may be mediated by electrically conductive materials as such and/or by diffusion of charged molecules having a suitable redox potential. Accordingly, the intermediate layer may be an electrolyte layer and/or an electrically conductive charge transport layer, for example.

According to a preferred embodiment of the invention, the intermediate and/or charge transport layer may contain a solvent or may be substantially free of a solvent. This also applies generally for the electrolyte of the invention. Generally, there is a solvent if the solvent provides 0.5% or more, 1% or more, preferably 5% or more, more preferably 10% or more and most preferably 20% or more of the weight of this layer.

Preferably, the intermediate layer or the electrolyte comprises the complex of the present invention. The complex may, for example, be added in the form of a salt, or, if the complex is neutral, in any isolated or purified form, for example.

According to an embodiment, the intermediate layer is an electrolyte comprising one or more ionic liquids.

Electrolytes comprising as a major component ionic liquids (ionic-liquid based electrolytes) are, disclosed, for example, in WO2007/093961. Solvent free electrolytes produced from eutectic melts, are disclosed in the international patent application WO 2009/083901, and are also encompassed by the present invention.

The intermediate layer or electrolyte may also be an electrically conductive charge transport layer, in which electrons and/or holes move by electronic motion, instead of diffusion of charged molecules. Such electrically conductive layers may, for example, be based on organic compounds, including polymers. Accordingly, this layer may be an electron and/or hole conducting material. U. Bach et al. "Solid-state dye-sensitized mesoporous $TiO_2$ solar cells with high photon-to-electron conversion efficiencies", Nature, Vol. 395, Oct. 8, 1998, 583-585, disclose the amorphous organic hole transport material 2,2',7,7'-tetrakis(N,N-di-p-methoxyphenyl-amine)9,9'-spirofluorene (OMeTAD) in dye-sensitised solar cells. In WO2007/107961, charge transporting materials, which are liquid at room temperature and their application in dye-sensitized solar cells are disclosed. These and other materials may be used, for example, for the purpose of the present invention.

Both, said electrolyte or charge transport layer may comprise additives for improving the performance of the device, such as dopants in the case of charge transporters, and the like.

According to an embodiment, the complex of the invention may be used as a dopant in a charge transporting material, preferably an organic, electronically conducting charge transporting material, in the electrochemical and/or optoelectronic device of the present invention.

According to another embodiment, the electrolyte and/or the intermediate layer is a solvent based electrolyte.

The solvent, if present, is preferably an organic solvent. Examples of the organic solvent include: alcohol solvents such as methanol, ethanol, t-butanol and benzylalcohol; nitrile solvents such as acetonitrile, propionitrile and 3-methoxypropionitrile; nitromethane; halogenated hydrocarbons such as dichloromethane, dichloroethane, chloroform and chlorobenzene; ether solvents such as diethylether and tetrahydrofuran; dimethylsulfoxide; amide solvents such as N,N-dimethylformamide, N-methylformamide, formamide, N-methylacetamide, N,N-dimethylacetamide, N-methylpropionamide, and the like. N-methylpyrrolidone, 1,3-dimethylimidazolidinone, 3-methyloxazolidinone, ester solvents such as ethyl acetate and butylacetate; carbonate solvents such as diethyl carbonate, ethylene carbonate and propylene carbonate; ketone solvents such as acetone, 2-butanone and cyclohexanone; hydrocarbon solvents such as hexane, petroleum ether, benzene and toluene; sulforane; N,N,N',N'-tetramethyl urea; etc. Among these solvents, nitrile solvents and amide solvents are preferred. C1-C5 alkyl or C1-C5 alkoxynitrile solvents are particularly preferred (see examples above). The solvents can be used alone or in combination.

The intermediate layer and/or the electrolyte preferably comprises additives designed to improve stability and/or the performance characteristics of the device, such as N-alkylbenzimidazole, wherein the alkyl is a C1-C10 alkyl, which may be halogenated, for example, Guanidinium thiocyanate, substituted pyridines and bases having pKa between 3 to 6.

The method of the present invention preferably comprises the step of adding to said charge transport layer a salt comprising tetracyanoborate ($[B(CN)_4]^-$) and a cationic metal complex of formula I. In particular, tetracyanoborate is advantageously added to electrochemical devices, conveniently as a salt with the complex functioning as a redox-couple. In this way, not only are (other) anions avoided, which have no function and/or which may even unfavorably affect performance or stability of the device, but, in contrast, addition of a compound is achieved in an economic, practical and efficient way, which compound improves stability of such devices, including devices, in which tetracyanoborate was not used and/or could not be added without a further step.

The present invention will now be illustrated by way of examples. These examples do not limit the scope of this invention, which is defined by the appended claims.

EXAMPLES

Example 1

Synthesis of Bipyridine-Pyrazole Ligand tBuOK (2 g) was added to a suspension of pyrazole (1 g) in dmso (80 mL) and stirred until a clear solution has formed. 6-chloro-2,2'-bipyridine (1 g, from HetCat) was added slowly by portion and the mixture heated at 140° C. for 14 hours. After cooling down to room temperature, water was added and the precipitate filtered and wash with water. The compound was further purified by silica gel chromatography column using Ethyl acetate/diethyl ether as eluent, leading to an off-white crystalline solid (450 mg, yield 39%). Spectroscopic analysis are as reported in the literature (*Inorg. Chem.* 1991, 30, 3733).

Example 2

Synthesis of CoII Complex $[Co(II)(bpy-pz)_2](PF6)_2$ 91 mg (0.382 mmol, excess) of $CoCl_2*6H_2O$ were dissolved in 25 mL of water while in another flask 93 mg (0.418 mmol) of the pyridine-pyridine-pyrazole ligand of Example 1 were dissolved in 25 mL of acetone. The solutions were combined and heated to 55° C. for 2 h. Then 400 mg of NH$_4$PF$_6$ dissolved in 100 mL of water were added to the mixture. The mixture was stored overnight at 3° C. for precipitation. Then the product was collected on a sintered glass frit and dried in vacuo. The pure product was obtained as orange solid and contained compound (70) shown below. Yield: 95 mg (0.12 mmol, 57%). $^1$H NMR (400 MHz, acetone-D6): δ 112.95 (s, 2H, ArH), 91.83 (s, 2H, ArH), 89.23 (s, 2H, ArH), 75.68 (s, 2H, ArH), 69.31 (s, 2H, ArH), 66.22 (s, 2H, ArH), 43.00 (s, 2H, ArH), 40.74 (s, 2H, ArH), 19.01 (s, 2H, ArH), 13.61 (s, 2H, ArH) ppm.

Example 3

Synthesis of CoIII Complex [Co(III)(bpy-pz)$_2$](PF6)$_3$ 91 mg (0.382 mmol, excess) of CoCl$_2$*6H$_2$O were dissolved in 25 mL of water while in another flask 93 mg (0.418 mmol) of the pyridine-pyridine-pyrazole ligand of Example 1 were dissolved in 25 mL of methanol. The solutions were combined and heated to 55° C. for 2 h. The mixture was allowed to cool to room temperature and then H$_2$O$_2$ (1 mL, 30%) and HCl (1 mL, 25%) were added to oxidize the cobalt. The mixture was stirred for 1 h and then 400 mg of NH$_4$ PF$_6$ dissolved in 100 mL of water were added to the mixture. The mixture was stored overnight at 3° C. for precipitation. Then the product was collected on a sintered glass frit and dried in vacuo. The product was obtained as orange solid and contained 65% of the desired Co(III) complex (compound (71)) and 35% of the corresponding Co(II) complex. Yield: 97 mg (0.10 mmol, 49%). $^1$H NMR (400 MHz, acetone-D6): δ 9.41-9.26 (m, 3H, ArH), 9.00 (t, $^3J_{HH}$=9.3 Hz, 2H, ArH), 8.47 (t, $^3J_{HH}$=7.6 Hz, 1H, ArH), 7.92 (d $^3J_{HH}$=5.8 Hz, 1H, ArH), 7.84 (s, 1H, ArH), 7.62 (t, $^3J_{HH}$=6.7 Hz, 1H, ArH), 6.86 (s, 1H, ArH) ppm.

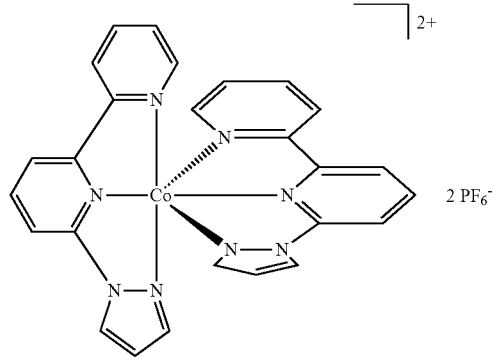

(70)

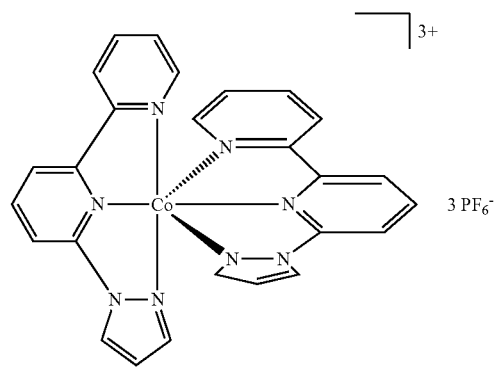

(71)

Example 4

Synthesis of CoII Complex with Bidentate Ligands [Co(II)(py-pz)$_3$](PF6$_2$)

Pyridine-pyrazole was obtained as disclosed in Chemishe Berichte, 1996, 129, 589.

225 mg (1.55 mmol, 3.1 eq) of pyridine-pyrazole ligand were dissolved in 20 mL of MeOH and then 119 mg (0.5 mmol, 1 eq) of CoCl$_2$*6H$_2$O were added as a solid. The mixture was heated to reflux for 2 h. After cooling to r. t. excess of KPF$_6$ dissolved in MeOH was added to the mixture. The mixture was stored at 3° C. for precipitation. After 3 h the product was collected on a sintered glass frit and dried in vacuo. The pure product was obtained as orange crystals, containing compound (72). Yield: 246 mg (0.33 mmol, 66%).

Example 5

Synthesis of CoIII Complex with Bidentate Ligands [Co(III)(py-pz)$_3$](PF6$_3$)

218 mg (1.5 mmol, 3.0 eq) of pyridine-pyrazole ligand were dissolved in 10 mL of water and heated to 75° C. until complete solution occurred. Then 119 mg (0.5 mmol, 1 eq) of CoCl$_2$*6H$_2$O were added to the colourless solution. To the pink solution H$_2$O$_2$ (1 mL, 30%) and HCl (1 mL, 25%) were added to oxidize the cobalt. After 10 min. 460 mg (2.5 mmol, 5 eq) of KPF$_6$ dissolved in 10 mL of hot water were added drop wise to the mixture. Precipitation occurred and the mixture was allowed to cool to room temperature. The product was collected on a sintered glass frit and dried in vacuo. The pure product was obtained as orange solid and contains compound (73). Yield: 259 mg (0.28 mmol, 56%). $^1$H NMR (400 MHz, acetone-D6): δ 9.56-9.53 (m, 3H, ArH), 8.73-8.64 (m, 6H, ArH), 8.01-7.81 (m, 9H, ArH), 7.27-7.23 (m, 3H, ArH) ppm.

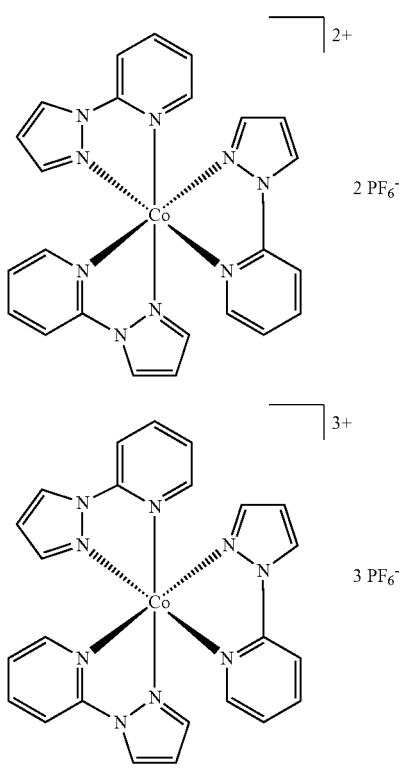

(72)

(73)

Example 6

Synthesis of an Organic Dye (Y123)

Figure 16:
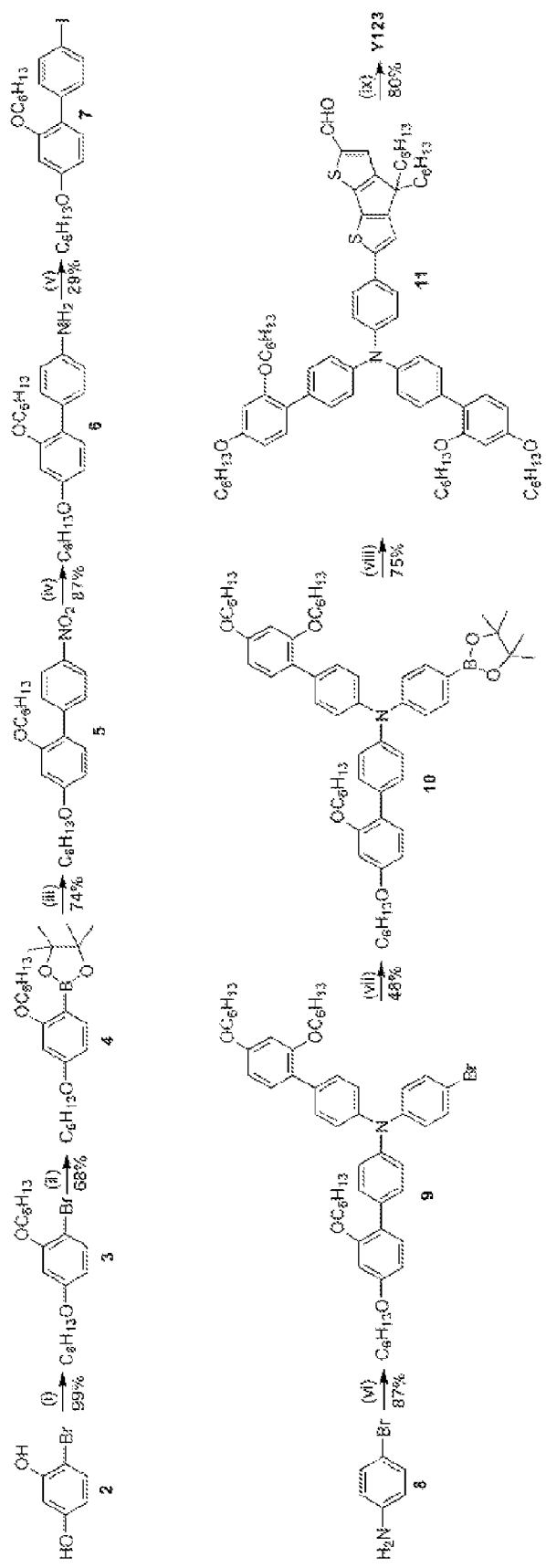
FIG. 16 schematically shows the synthesis of the dye 3-{6-{4-[bis(2',4'-dihexyloxybiphenyl-4-yl)amino-]phenyl}-4,4-dihexyl-cyclopenta-[2,1-b:3,4-b']dithiophene-2-yl}-2-cyanoacrylic acid. The reagents are: (i) 1-bromohexane, $K_2CO_3$, DMF; (ii) n-BuLi, THF, isopropyl pinacol borate; (iii) 4-bromo-nitrobenzene, $Pd(PPh_3)_2Cl_2$, $Cs_2CO_3$, DMF, $H_2O$; (iv) Zn, $NH_4Cl$, acetone, $H_2O$; (v) $H_2SO_4$, $NaNO_2$, $K_1$, $H_2O$; (vi) 6, CuI, 1,10-phenantroline, t-BuOK, toluene; (vii) n-BuLi, THF, isopropyl pinacol borate; (viii) 1, $Pd(PPh_3)_2Cl_2$, $Cs_2CO_3$, DMF, $H_2O$; (ix) cyanoacetic acid, piperidine, $CHCl_3$.

The organic dye (3-{6-{4-[bis(2',4'-dihexyloxybiphenyl-4-yl)amino-]phenyl}-4,4-dihexyl-cyclo-penta-[2,1-b:3,4-b']dithiophene-2-yl}-2-cyanoacrylic acid) is prepared in accordance with the scheme shown in FIG. 16.

Example 7

Preparation of a Dye Sensitized Solar Cell Using the Complex-Based Redox-Couple $TiO_2$ electrodes were prepared of 2.5-3 μm transparent layer (20 nm diameter anatase particles), in accordance with the literature (Yum, J. H.; Jang, S. R.; Humphry-Baker, R.; Grätzel, M.; Cid, J. J.; Tones, T.; Nazeeruddin, M. K. Langmuir 2008, 24, 5636). The $TiO_2$ electrodes were immersed into a 0.1 mM solution of the organic dye obtained in Example 6 (FIG. 16) in tert-butanol/acetonitrile mixture (1:1 v/v) and kept at room temperature for 15 hrs.

The applied electrolyte is consisted of 0.17-0.2 M [Co(II)(bpy-pz)$_2$](PF6)$_2$, 0.04-0.05 M [Co(III)(bpy-pz)$_2$](PF6)$_3$, 0.1M LiClO$_4$, and 0.25M tert-butylpyridine in acetonitrile.

The dye-adsorbed $TiO_2$ electrode and thermally platinized counter electrode were assembled into a sealed sandwich type cell with a gap of a hot-melt ionomer film, Surlyn (25 μm, Du-Pont). In order to reduce scattered light from the edge of the glass electrodes of the dyed $TiO_2$ layer, a light shading mask was used onto the DSCs, so the active area of DSCs was fixed to 0.2 cm². For photovoltaic measurements of the DSCs, the irradiation source was a 450 W xenon light source (Osram XBO 450, Germany) with a filter (Schott 113), whose power was regulated to the AM 1.5G solar standard by using a reference Si photodiode equipped with a colour matched filter (KG-3, Schott) in order to reduce the mismatch in the region of 350-750 nm between the simulated light and AM 1.5G to less than 4%. The measurement of incident photon-to-current conversion efficiency (IPCE) was plotted as a function of excitation wavelength by using the incident light from a 300 W xenon lamp (ILC Technology, USA), which was focused through a Gemini-180 double monochromator (Jobin Yvon Ltd.).

The results are summarized in Table 1 below.

TABLE 1

Current (I)-Voltage (V) characteristic of dye-sensitized solar cell composed of an organic dye as described with Cobalt based redox couples under various light intensities.

| Redox couple | $TiO_2$ (μm) | $I_0$ (% Sun) | $J_{SC}$ (mA/cm²) | $V_{OC}$ (mV) | Fill factor | PCE (%) |
|---|---|---|---|---|---|---|
| Examples 4 and 5 (bidentate) | 2.7 | 9.5 | 0.63 | 905 | 0.64 | 3.83 |
| | | 51 | 2.50 | 991 | 0.61 | 2.90 |
| | | 100 | 3.75 | 1020 | 0.59 | 2.26 |
| Examples 2 and 3 (tridentate) | 2.7[a] | 9.5 | 1.07 | 974 | 0.67 | 7.34 |
| | | 51 | 5.38 | 1040 | 0.66 | 7.21 |
| | | 100 | 9.37 | 1060 | 0.64 | 6.33 |
| | 2.7 | 9.5 | 1.05 | 943 | 0.81 | 8.39 |
| | | 51 | 5.49 | 999 | 0.76 | 8.12 |
| | | 100 | 10.4 | 1020 | 0.70 | 7.42 |
| | 5.5[b] + 4 | 9.5 | 1.32 | 935 | 0.75 | 9.77 |
| | | 51 | 7.07 | 995 | 0.75 | 10.3 |
| | | 100 | 13.5 | 1010 | 0.70 | 9.52 |

[a]The electrolyte consists of 80% concentration of $Co^{2+}/Co^{3+}$ tridentate redox system,
[b]The average 20 nm sized $TiO_2$ anatase with average 32 nm sized pore was used.

Figure 2:
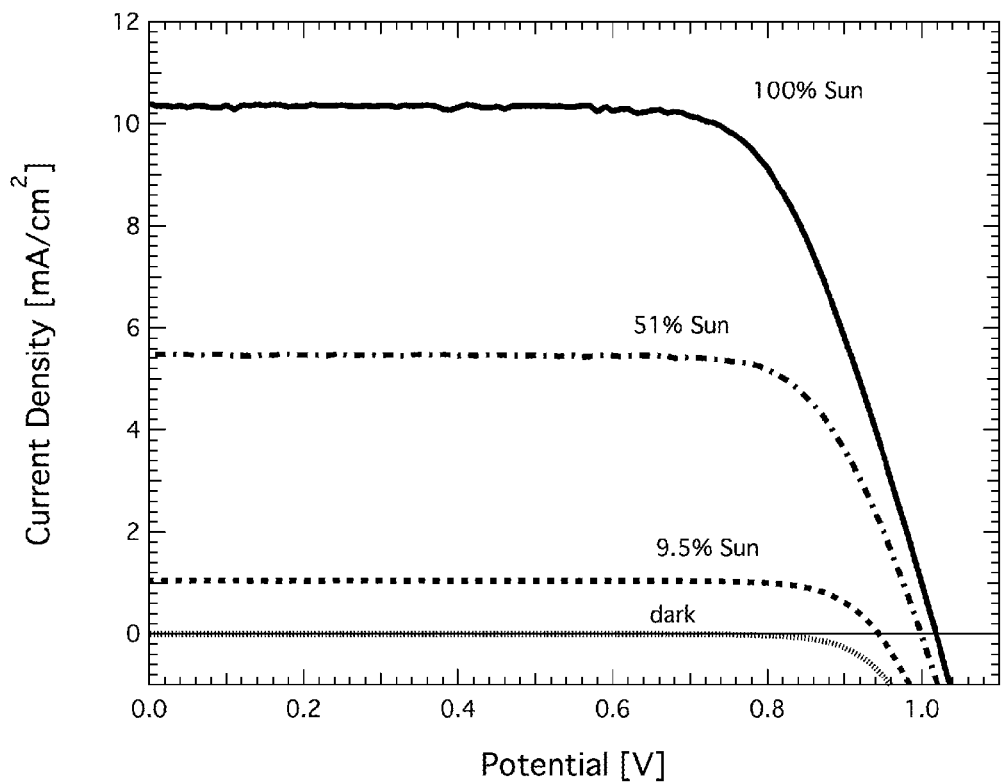
FIG. 2 shows Current (I)-Voltage (V) characteristic of a dye-sensitized solar cell containing an organic dye (FIG. 16) on 2.7 μm TiO$_2$ with cobalt redox couples according to another embodiment of the invention.

The results in Table 1 show that all the open circuit voltage ($V_{OC}$) of $Co^{2+}/Co^{3+}$ are over 900 mV under 10% light intensity and they augment over 1000 mV under full sun condition. In particular, $Co^{2+}/Co^{3+}$ tridentate system (FIG. 2) showed promising results in terms of the power conversion efficiency. The current-voltage results obtained with the bidentate system are shown in FIG. 1. Dye-sensitized solar cells supported by the 2.7 μm $TiO_2$ yielded 10.4 mA/cm² of the short circuit current ($J_{SC}$), 1020 mV of $V_{OC}$, 0.70 of the fill factor (ff) and the corresponding power conversion efficiency (PCE) of 7.42%. It should be here noted that 1060 mV of the $V_{OC}$ is feasible by tuning the redox concentration (see Table 1).

Figure 3:
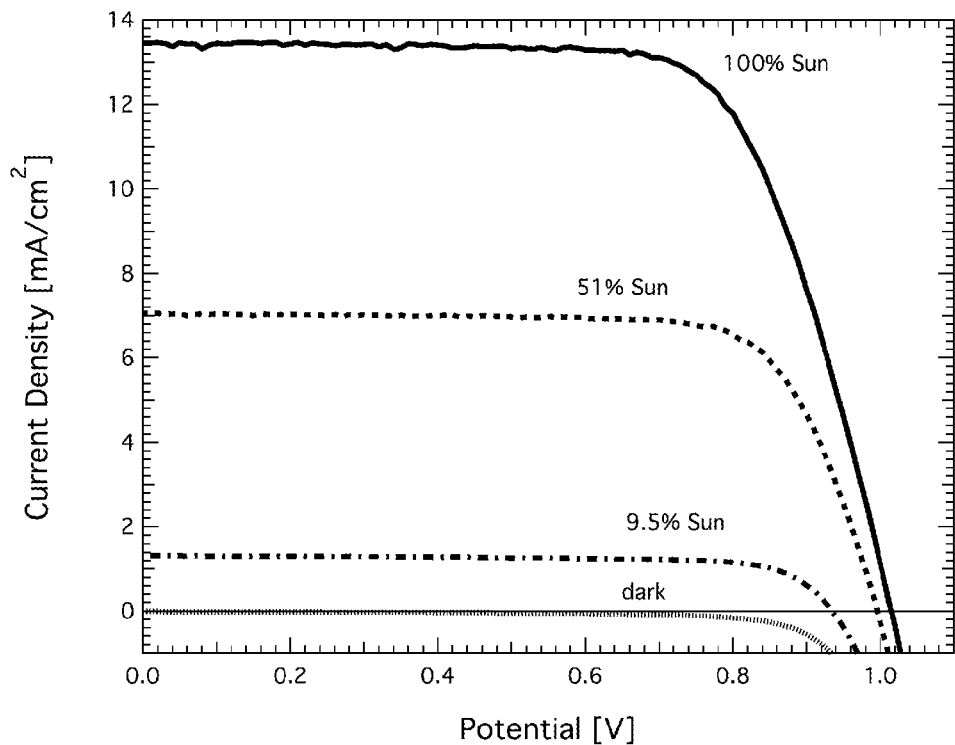
FIG. 3 shows Current (I)-Voltage (V) characteristic of dye-sensitized solar cell containing an organic dye (FIG. 16) on 5.5 μm transparent TiO$_2$ layer+4 μm scattering layer with cobalt tridentate redox couples according to an embodiment of the invention.
Figure 4:
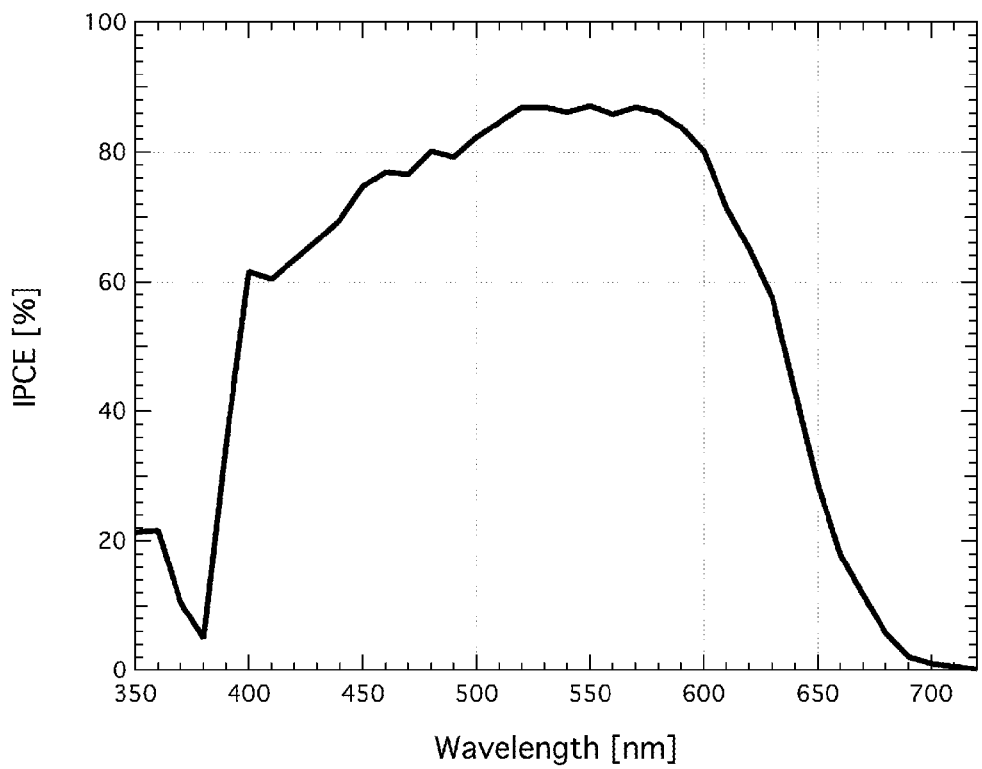
FIG. 4 shows the incident-photon to current conversion efficiency of dye-sensitized solar cell containing an organic dye (FIG. 16) on 5.5 μm transparent TiO$_2$ layer+4 μm scattering layer with cobalt tridentate redox couples according to the same embodiment of the invention as FIG. 3.

In another example, the $TiO_2$ double layer composed of 5.5 μm transparent nanocrystalline $TiO_2$ layer and 4 μm scattering layer (400 nm sized particles) was used for the photo-anode. The result in Table 1 (three bottom lines) and FIG. 3 showed an increase in $J_{SC}$ to 13.5 mA/cm² as retaining a high $V_{OC}$, 1010 mV. Overall, the PCE improved to 9.52% under full sun and over 10% under 51% sun. The integration of the incident-photon to current conversion efficiency (IPCE) (shown in FIG. 4) over the AM-1.5 solar emission gave $J_{SC}$ values of 13.4 mA/cm² in good agreement with the I-V measured values. The high IPCE reaching over 85% near the maximum around 550 nm was observed.

For comparison, the CoII Complex of tris bipyridine [Co(II)(bpy)$_3$](PF6)$_2$ (Feldt, S. et al., J. Am. Chem. Soc. 2010, 132, 16714-16724) gave 920 mV, which is 140 mV less than the new electrolyte.

These results show that the redox-couples according to the invention are suitable to adjust and in particular to increase the oxidation potential of the redox mediator, thereby increasing the open circuit voltage of the solar cells. This is an important advantage with respect to iodide/triiodide based redox couple, the oxidation potential of which cannot be substantially changed. Never were such high $V_{OC}$ obtained based on the $I^-/I_3^-$ redox couple. It is in particular surprising that impressive conversion efficiencies (PCE) of over 10% were obtained without any further optimization of the tested system.

Example 8

Synthesis of $Co(bpy)_3[B(CN)_4]_2$, $Co(bpy)_3[B(CN)_4]_3$ Cobalt Complexes $CoCl_2.6H_2O$ (0.25 g) was dissolved in 5 ml of water and to this added a methanolic solution of 2,2'-bipyridine (0.55 g) drop wise while stirring. After 5 minutes of stirring potassium tetracyanoborate (1.2 g) in water was added. The precipitated complex was filtered, washed with water and dried under vacuum to isolate $Co(bpy)_3[B(CN)_4]_2$. $CoCl_2.6H_2O$ (0.25 g) was dissolved in 5 ml of water and to this was added a methanolic solution of 2,2'-bipyridine (0.55 g) drop wise while stirring. After 5 minutes of stirring was added one molar equivalent of bromine solution in methanol while stirring. After 5 minutes more stirring the solution was filtered to remove any precipitate. Then the solvent was evaporated using a rotavapor under vacuum and re-dissolved in methanol solution (15 ml) and filtered. To the filtrate was added potassium tetracyanoborate (1.2 g) in water. The precipitated complex was filtered, washed with water and dried under vacuum to isolate $Co(bpy)_3[B(CN)_4]_3$.

Example 9

Preparation of Electrolytes and Absorption Spectra

The cobalt based electrolyte was prepared using 0.22 M of Co(II) and 0.05 M of Co(III) of Example 8 in a mixture of valeronitrile/acetonitrile (15:85 v/v). The additives are 0.1M LiClO4, and 0.2 M tert-butylpyridine.

Figure 5:
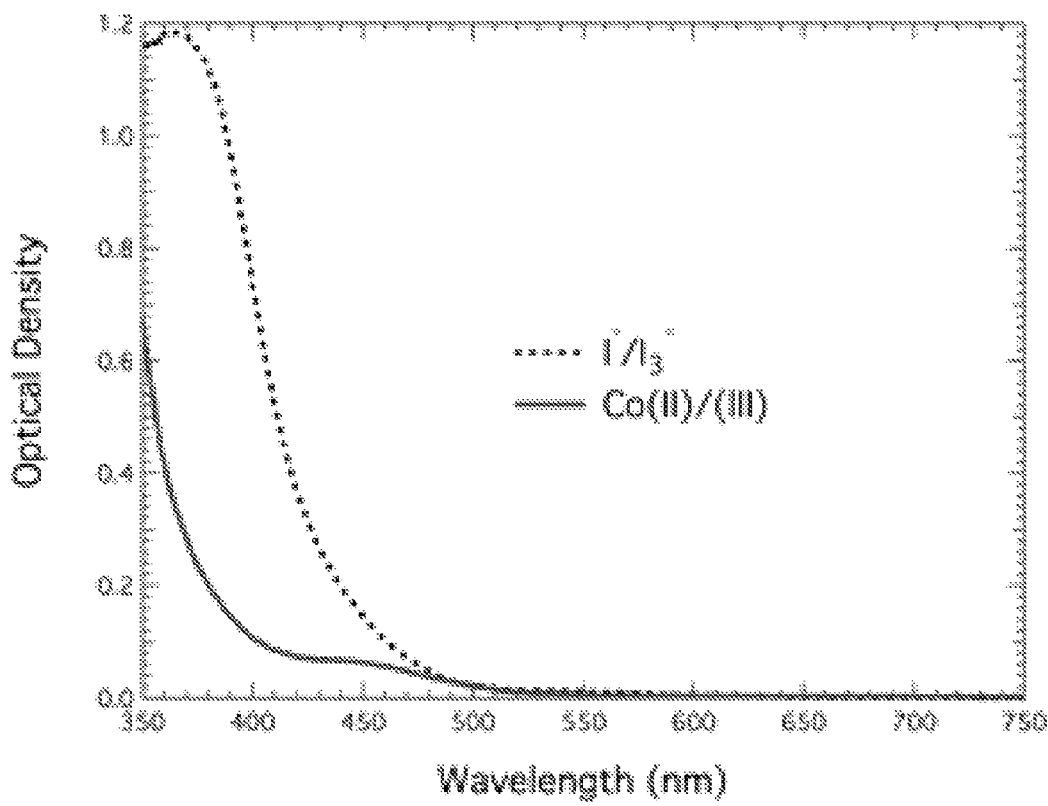
FIG. 5 compares absorption spectra of an electrolyte of a device according to an embodiment of the invention with the iodide-based electrolyte Z960, which is described in the examples (measurements were performed with the electrolytes diluted 200 times in acetonitrile).

For comparison, high performance iodide based electrolyte coded Z960 was prepared. This electrolyte contained 1.0 M 1,3-dimethylimidazolium iodide (DMII), 0.03M iodine, 0.1M guanidinium thiocyanate, 0.5M tert-butylpyridine and 0.05M LiI in a mixture of valeronitrile/acetonitrile (15:85 v/v). The N1 electrolyte was as Z960 but had the same concentrations of tert-butylpyridine and $Li^+$ as the $Co^{2+}/Co^{3+}$ containing formulation of the invention. FIG. 5 compares the absorption spectra of the complex-based electrolyte of the invention with the iodide based electrolyte using the organic dye as described in Example 6 (measurements were performed with the electrolytes diluted 200 times in acetonitrile), showing reduced absorption of the electrolyte of the invention over the range of wavelength of 350 to 480 nm.

Example 10

Preparation of Further Solar Cells

A photoanode consisted of 2 μm thin transparent nanoporous $TiO_2$ (anatase) film covered by a 5 μm thick light-scattering layer consisting of 400 nm sized $TiO_2$ (anatase) particles. Platinized FTO glass was used as the counter electrode, as disclosed in Yum, J. H.; Jang, S. R.; Humphry-Baker, R.; Grätzel, M.; Cid, J. J.; Torres, T.; Nazeeruddin, M. K. Langmuir 2008, 24, 5636).

The $TiO_2$ film was stained with an organic dye (Example 6) by immersing it for 7 h in a 0.1 mM dye solution in tert-butanol/acetonitrile mixture (1:1 v/v).

For photovoltaic measurements of the DSCs, the irradiation source was a 450 W xenon light source (Osram XBO 450, Germany) with a filter (Schott 113), whose power was regulated to the AM 1.5G solar standard by using a reference Si photodiode equipped with a colour matched filter (KG-3, Schott) in order to reduce the mismatch in the region of 350-750 nm between the simulated light and AM 1.5G to less than 4%. The measurement of incident photon-to-current conversion efficiency (IPCE) was plotted as a function of excitation wavelength by using the incident light from a 300 W xenon lamp (ILC Technology, USA), which was focused through a Gemini-180 double monochromator (Jobin Yvon Ltd.).

Figure 6:
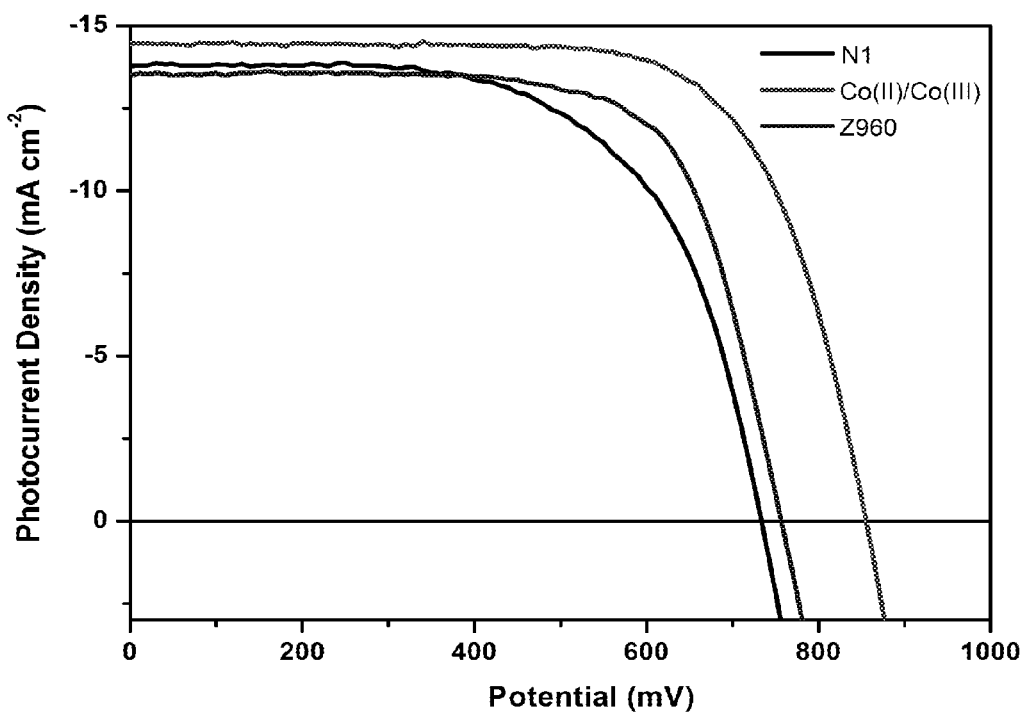
FIG. 6 shows photocurrent-voltage response at simulated full AM 1.5 sunlight of DSSCs employing the electrolyte according to an embodiment of the invention (Co(II)/Co(III)) in comparison with devices using the iodide/triiodide redox couple (N1, Z960). The superior performance of the device of the invention can be seen, which is due to higher short circuit current ($J_{SC}$), but more importantly due to the higher open current voltage ($V_{OC}$).

The results presented in Table 2 and FIG. 6 show that the performance of $Co^{2+}/Co^{3+}$ is superior to that of the $I^-/I_3^-$ based redox electrolyte, the $V_{OC}$ and $J_{SC}$ values being increased by 100 mV and 1 $mA/cm^2$ respectively, while the fill factor (ff) was hardly affected. The efficiency improved from 7.2% to 8.8% when changing from iodine to cobalt based redox system. Overall the efficiencies are remarkably high for DSSCs with such thin $TiO_2$ films used in this study. Our champion DSSC with cobalt based electrolyte reached even 9.6% efficiency under 1 sun light intensity, which shows that the device performance is better.

TABLE 2

Performances of DSSC employing $I^-/I_3^-$ and [Co(II)(bpy)$_3$][B(CN)$_4$]$_2$/[Co(III)(bpy)$_3$][B(CN)$_4$]$_3$ based electrolytes.

| Redox mediator | $V_{OC}$ (mV) | $J_{SC}$ (mA cm$^{-2}$) | FF | PCE (%) |
|---|---|---|---|---|
| (Z960) $I^-/I_3^-$ | 757 | 13.6 | 0.70 | 7.2 |
| (N1) $I^-/I_3^-$ | 733 | 13.8 | 0.62 | 6.3 |
| Invention | 855 | 14.6 | 0.70 | 8.8 |

Figure 7:
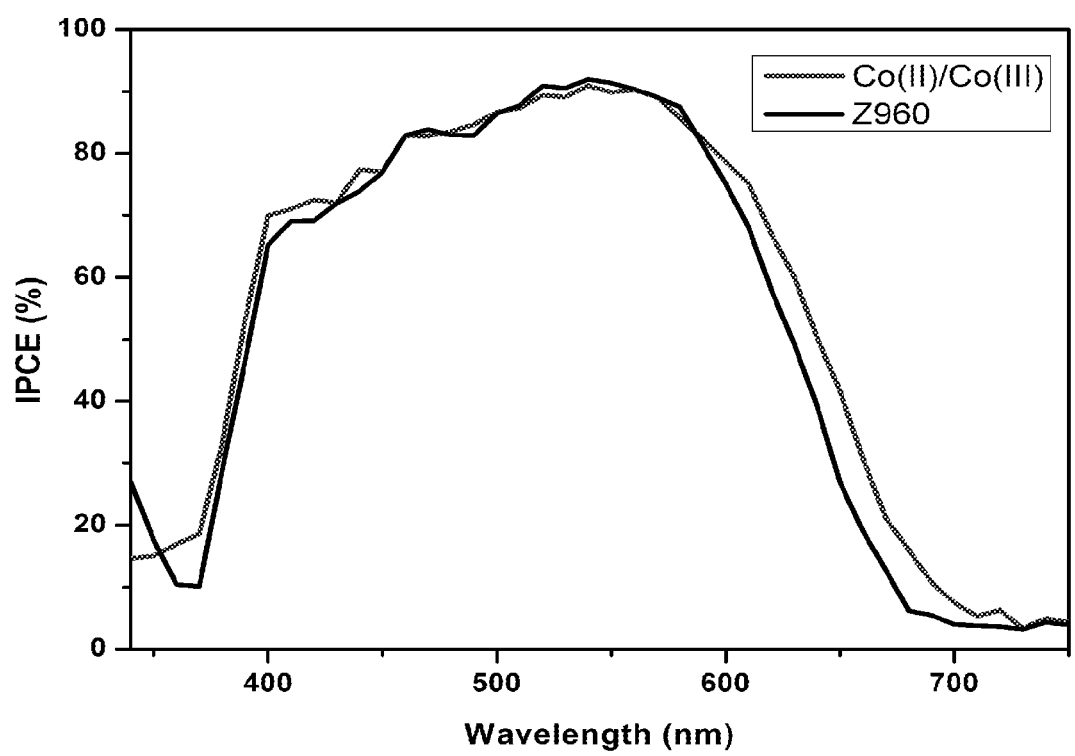
FIG. 7 shows the Incident-Photo-to-electron Conversion Efficiency (IPCE or quantum efficiency) of a device according to an embodiment of the invention (Co(II)/Co(III)), which is compared to a device using the same dye (see FIG. 4) but a prior art electrolyte. It can be seen that for the device of the embodiment, the IPCE spectrum is enhanced in the blue region (450-500 nm) and more clearly at wavelengths of 600 nm and larger.
Figures 1, 8:
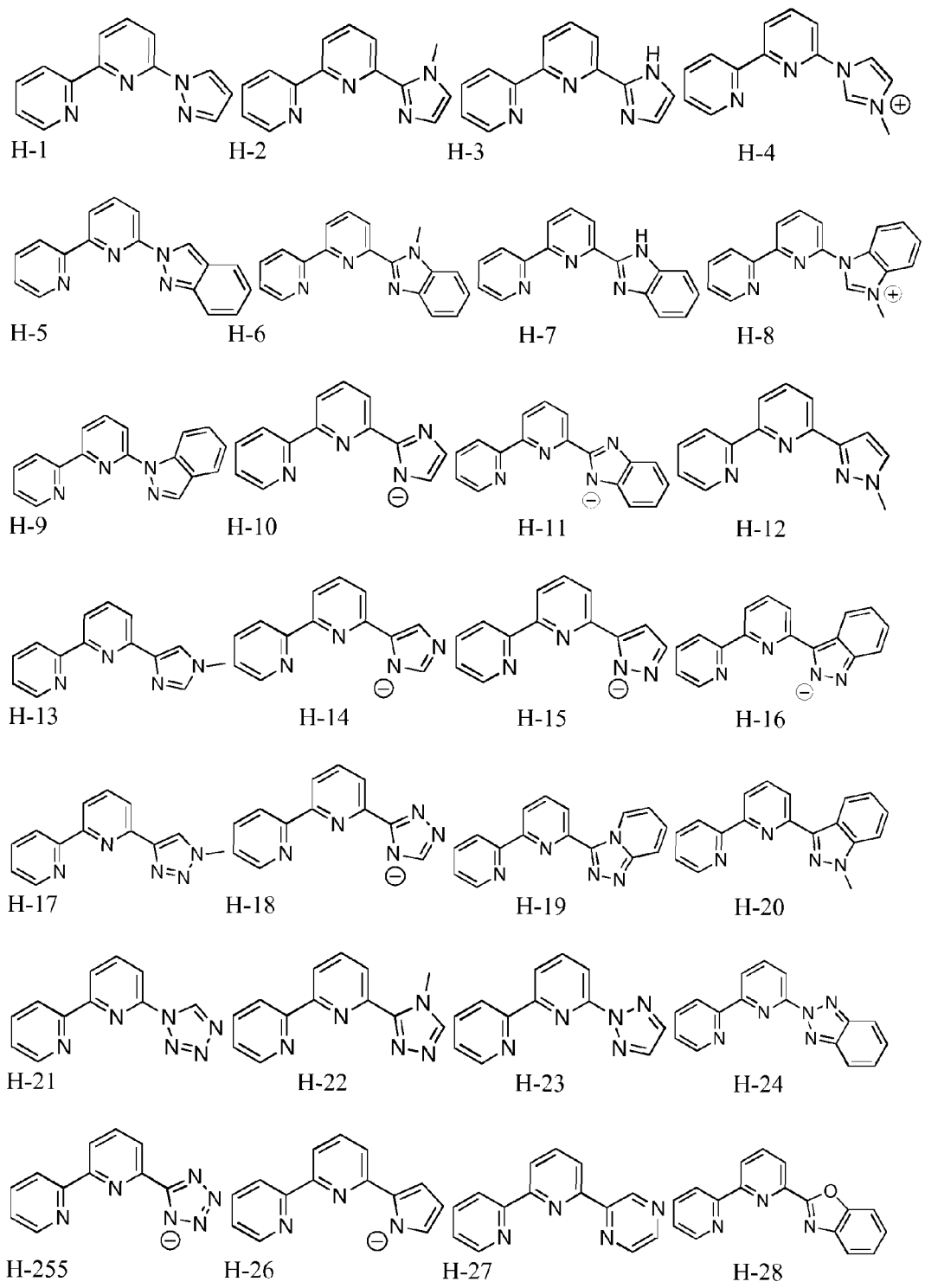
FIG. 8 (FIGS. 8-1 and 8-2) shows exemplary tridentate ligands La (H-1 to H-31) based on a substituted bipyridine, which ligands may be used in a complex in accordance with an embodiment of the invention.
Figures 2, 8:
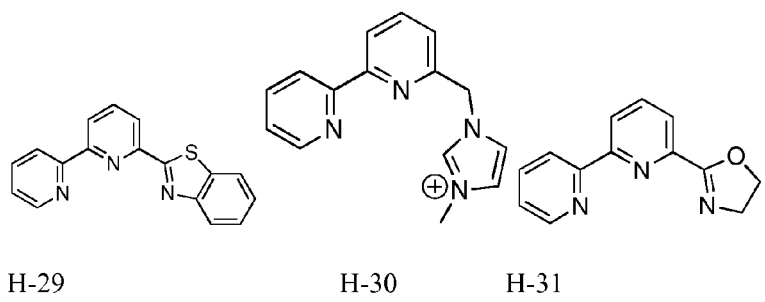
Figures 1, 9:
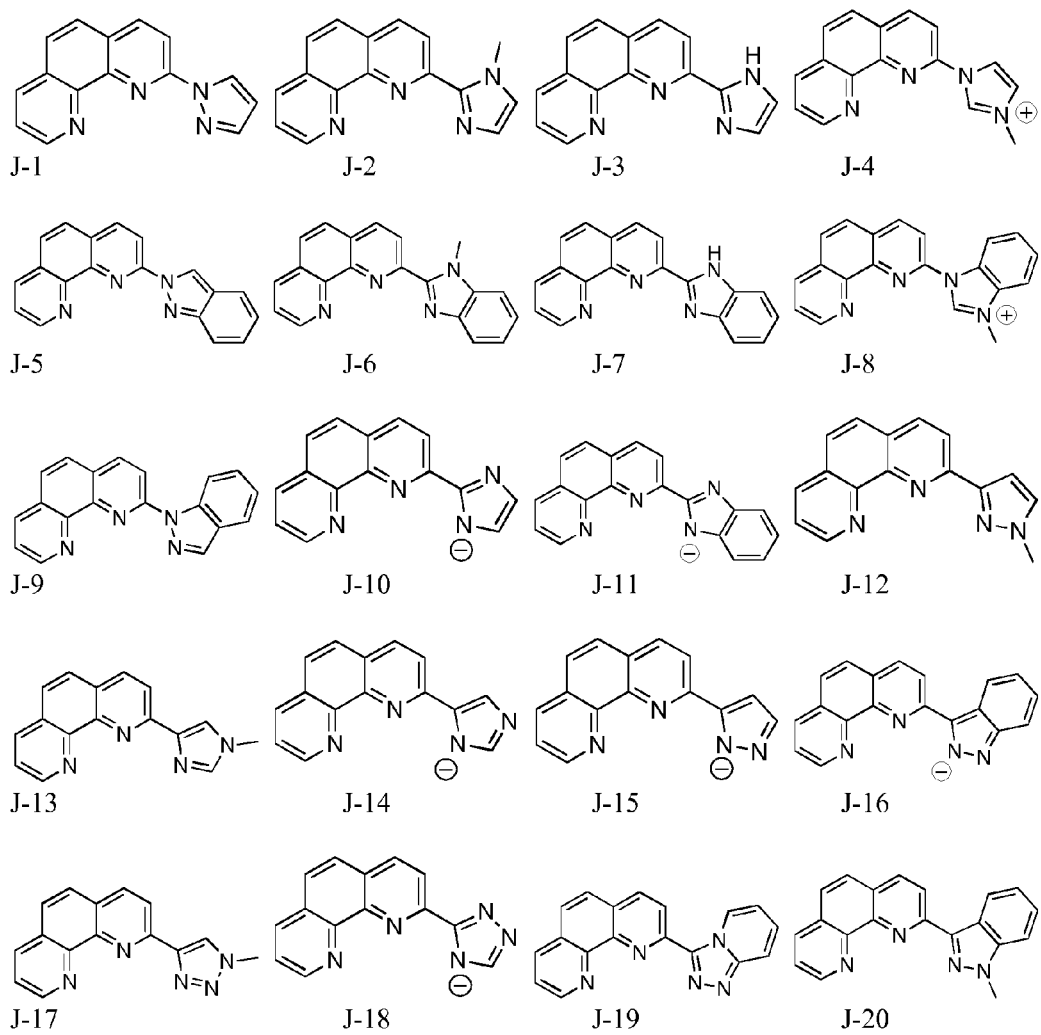
FIG. 9 (9-1 and 9-2) shows exemplary tridentate ligands La (J-1 to J-26) based on a substituted phenantroline, which ligands may be used in a complex in accordance with an embodiment of the invention.
Figures 2, 9:
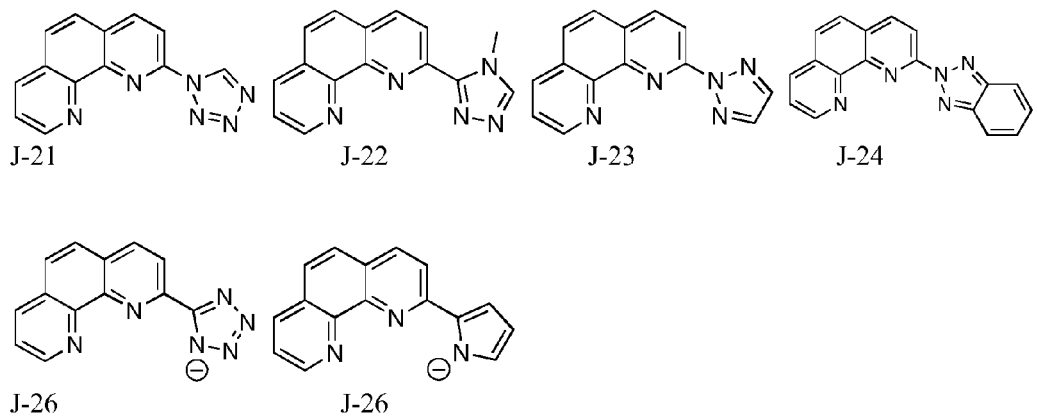
Figures 1, 10:
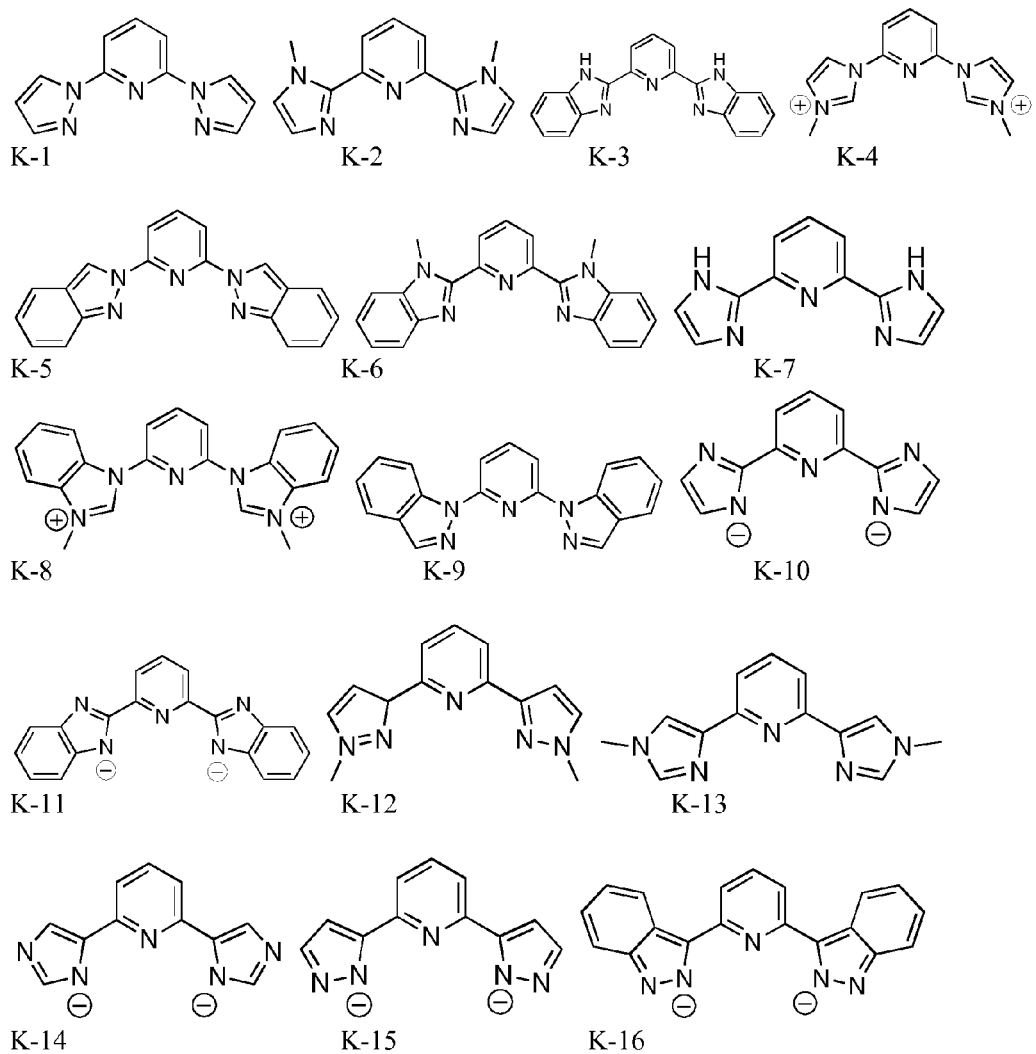
FIG. 10 (10-1 and 10-2) shows exemplary tridentate ligands La (K-1 to K-33) based on a di-substituted pyridine, which ligands may be used in a complex in accordance with an embodiment of the invention.
Figures 2, 10:
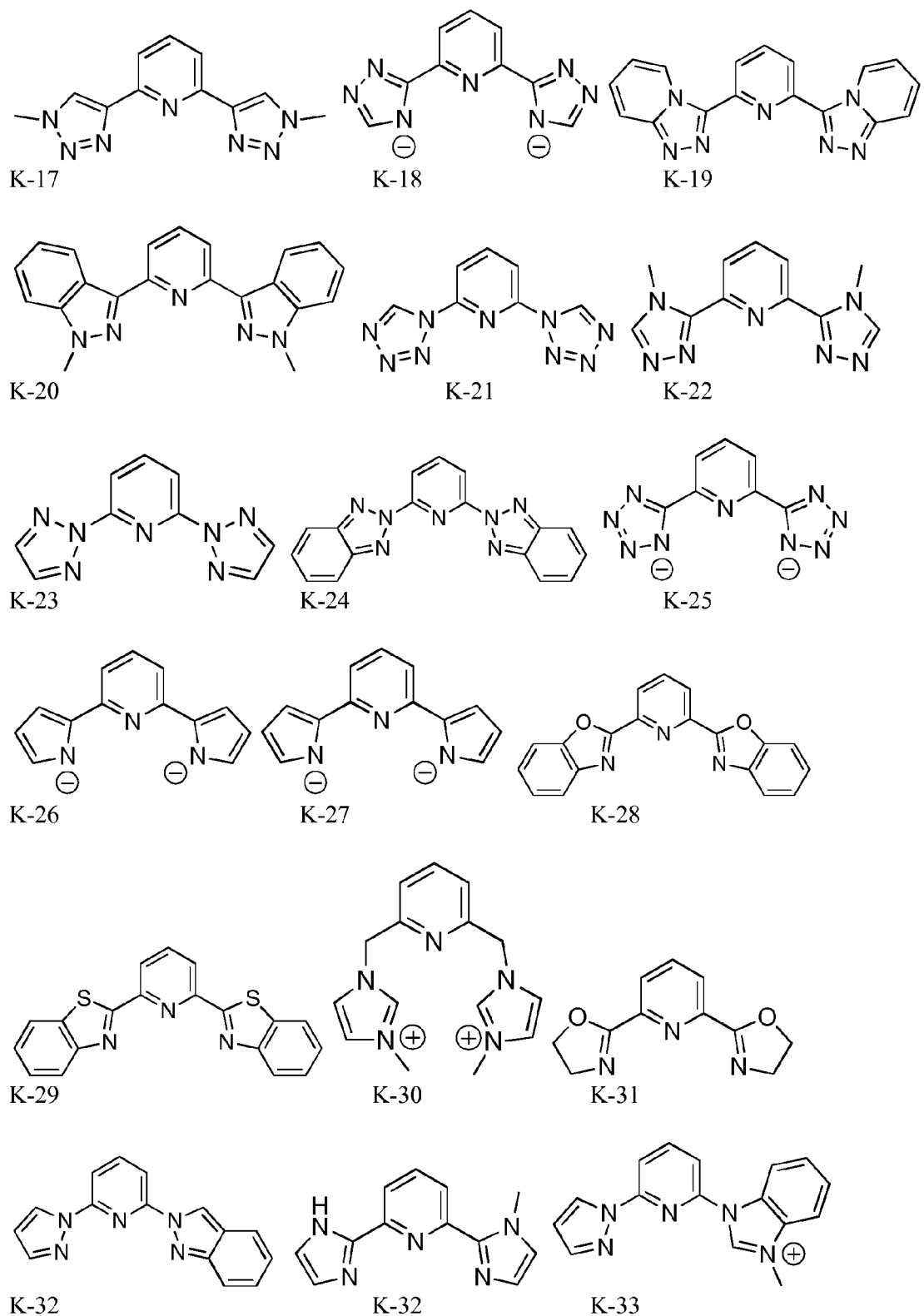
Figure 11:
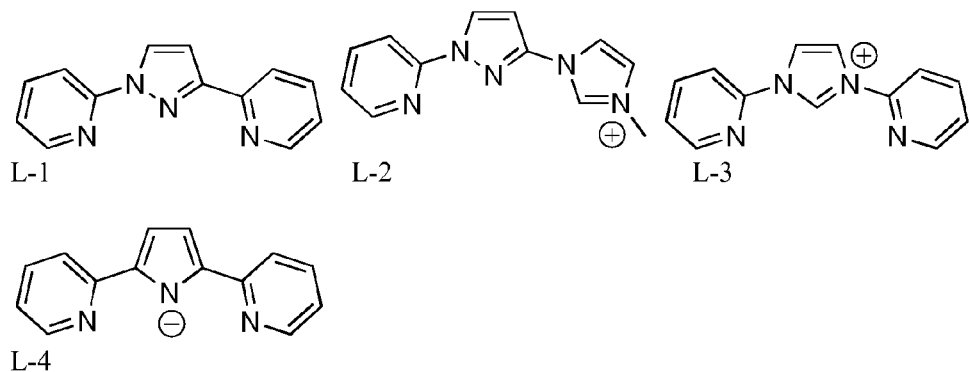
FIG. 11 shows exemplary tridentate ligands La (L-1 to L-4) based on a di-substituted pyrazole, imidazole or pyrrole, which ligands may be used in a complex in accordance with an embodiment of the invention.
Figures 1, 12:
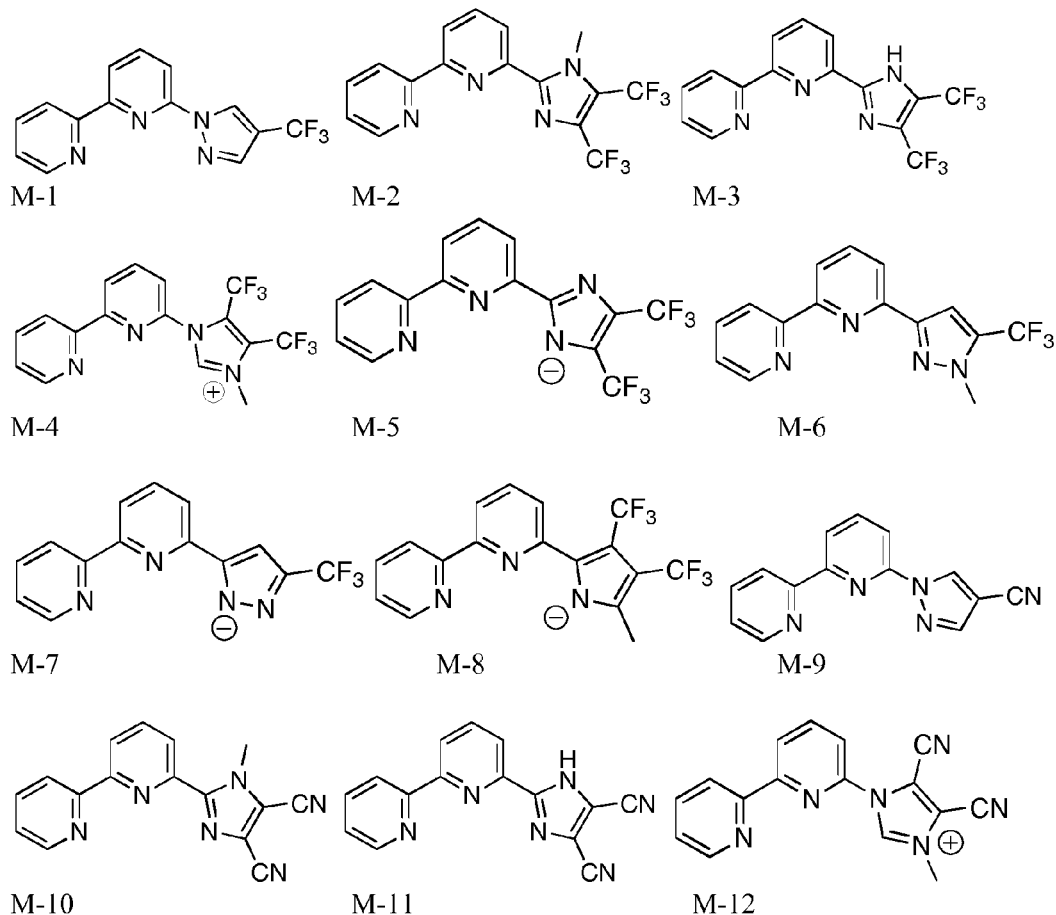
FIG. 12 (12-1 and 12-2) shows exemplary ligands (M-1 to M-15) of a similar type as those shown in FIG. 8, with additional substituents being present.
Figures 2, 12:
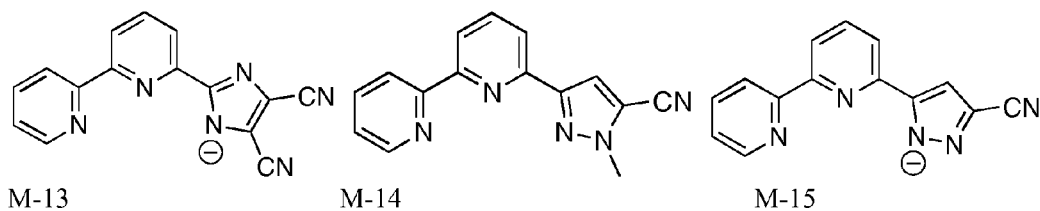
Figures 1, 13:
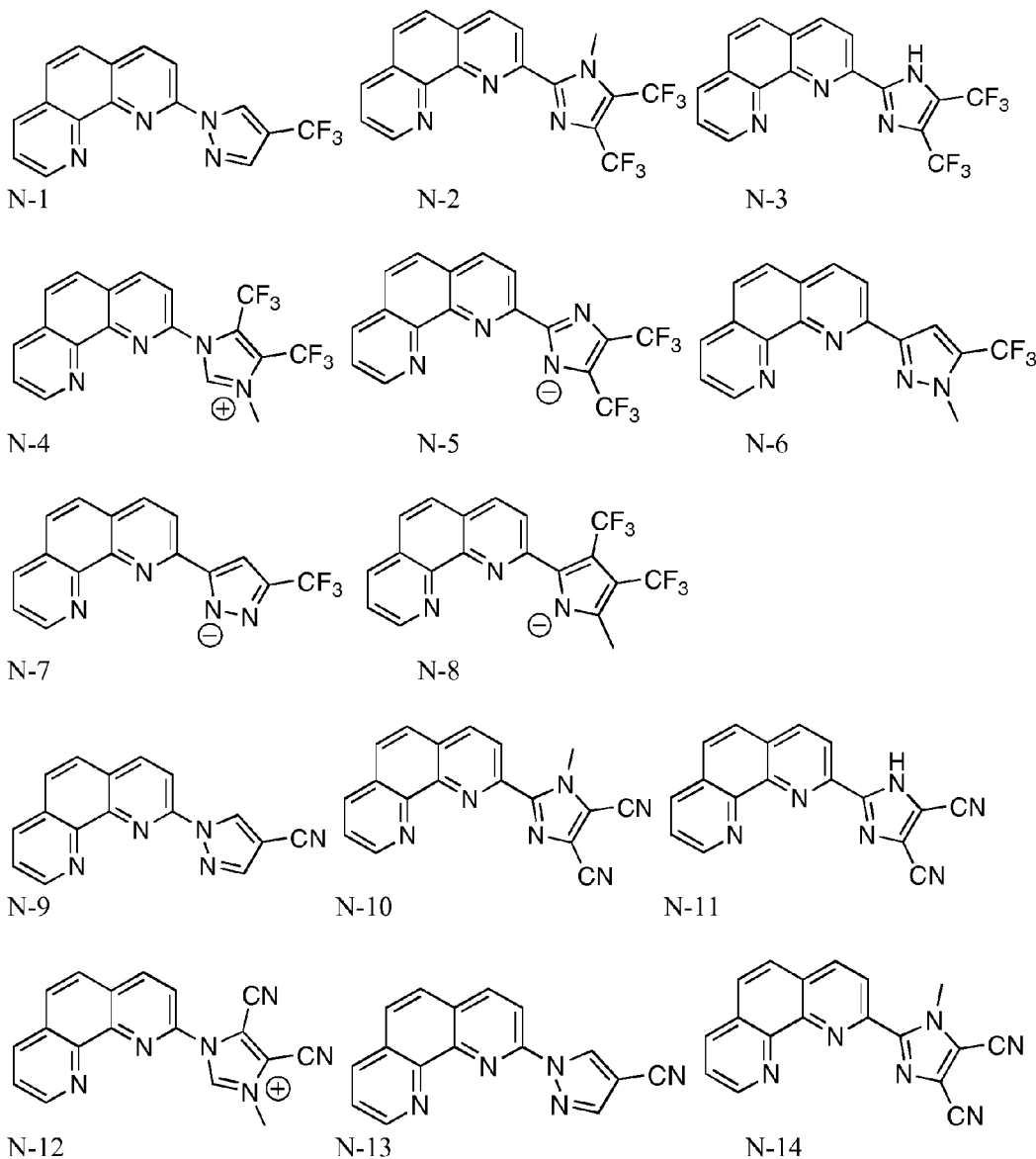
FIG. 13 (13-1 and 13-2) shows exemplary ligands (N-1 to N-20) of a similar type as those shown in FIG. 9, with additional substituents being present.
Figures 2, 13:
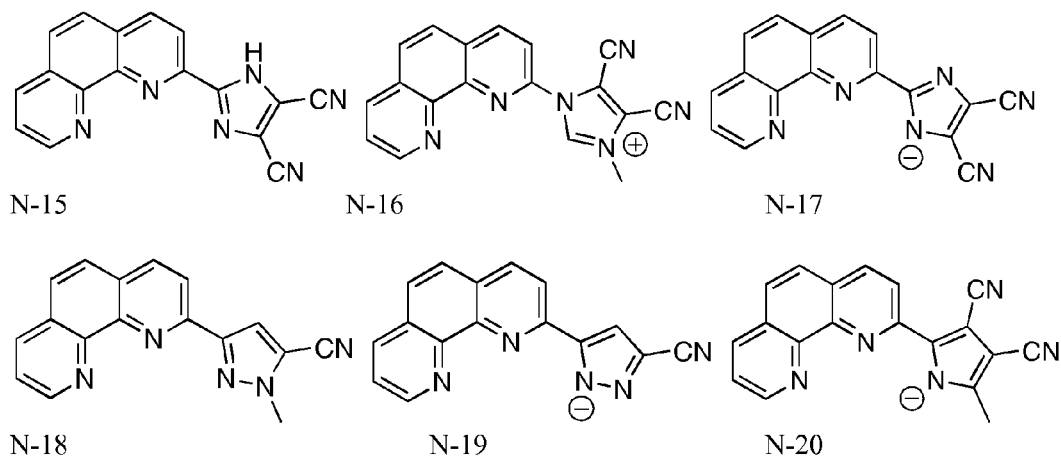
Figures 1, 14:
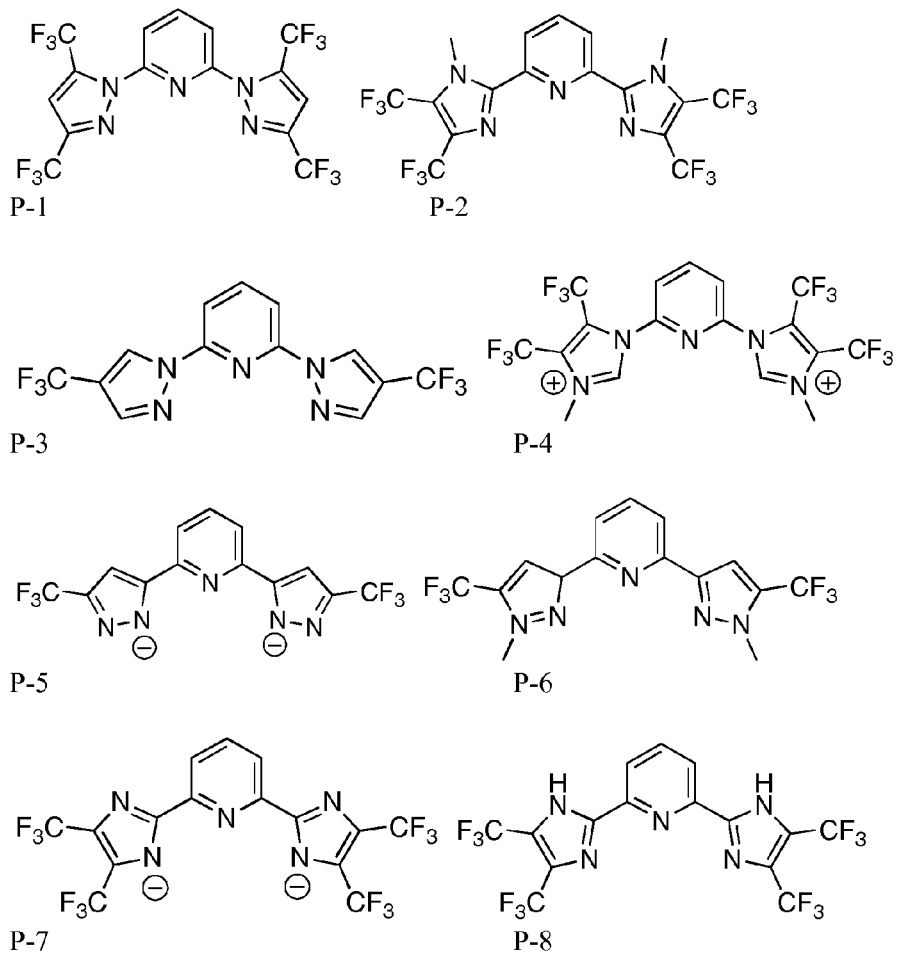
FIG. 14 (14-1 and 14-2) shows exemplary ligands (P-1 to P-16) of a similar type as those shown in FIG. 10, with additional substituents being present.
Figures 2, 14:
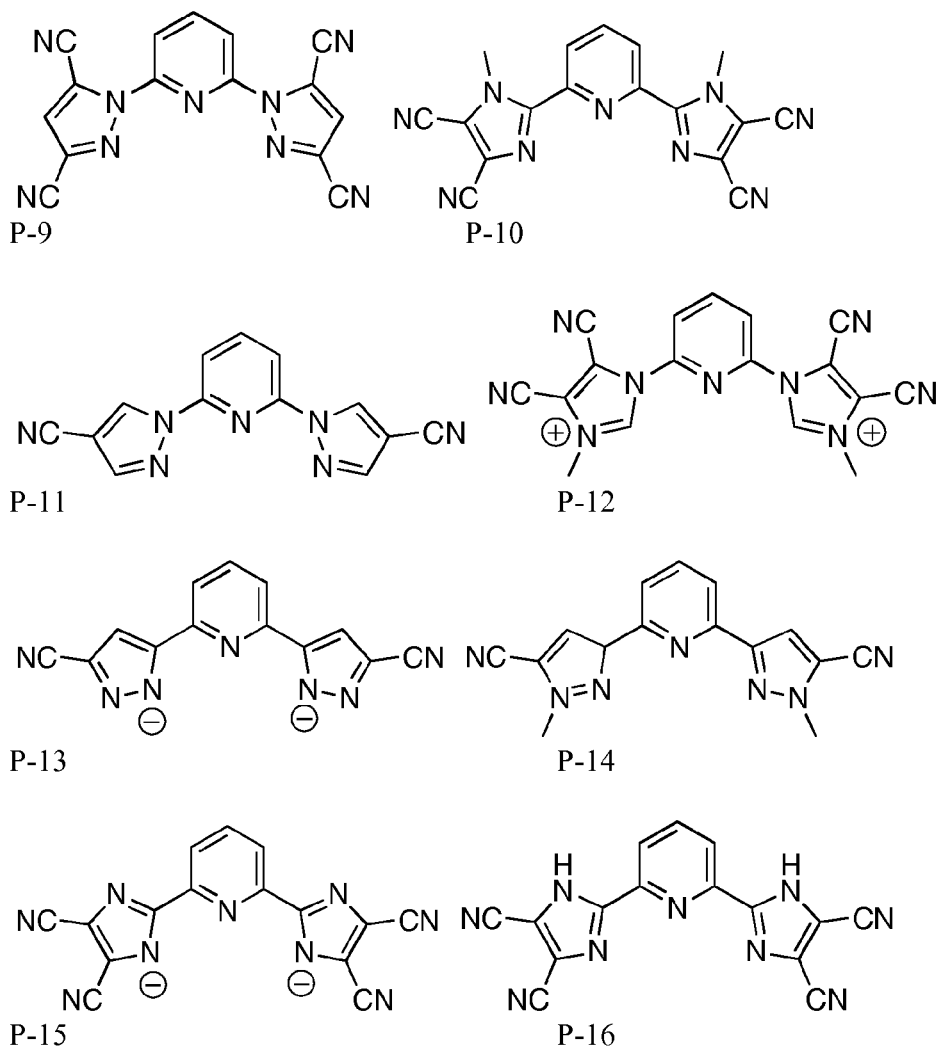
Figures 1, 15:
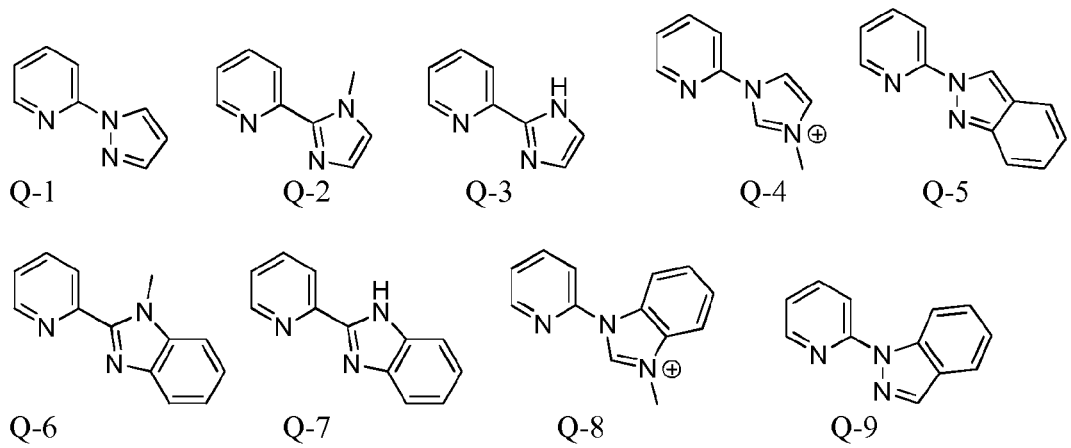
FIG. 15 (15-1, 15-2, 15-3, 15-4) shows exemplary bidentate ligands (Q-1 to Q-63) based on substituted pyridine, pyrazole, imidazole or pyrrole, which ligands may be used in a complex in accordance with an embodiment of the invention.
Figures 2, 15:
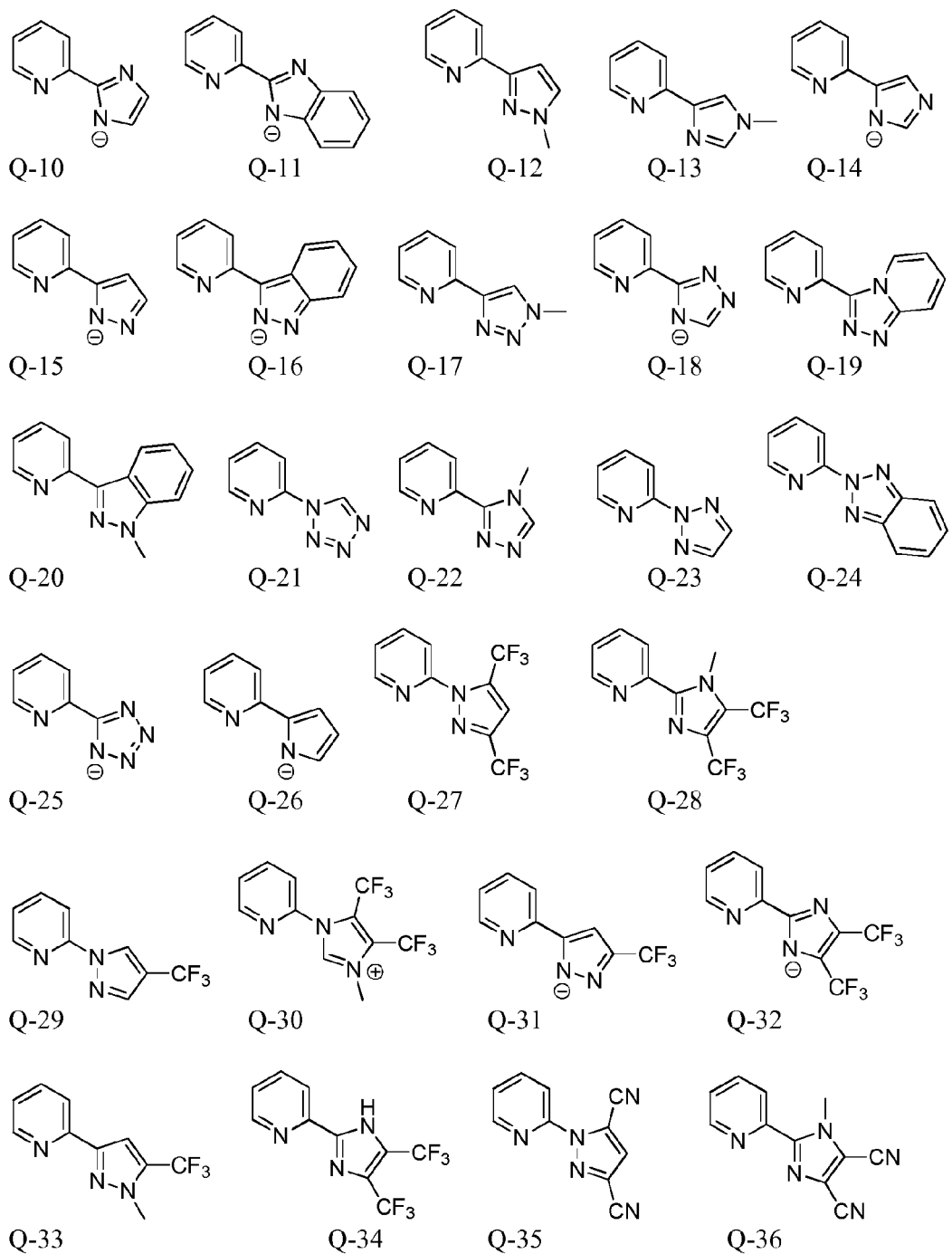
Figures 3, 15:
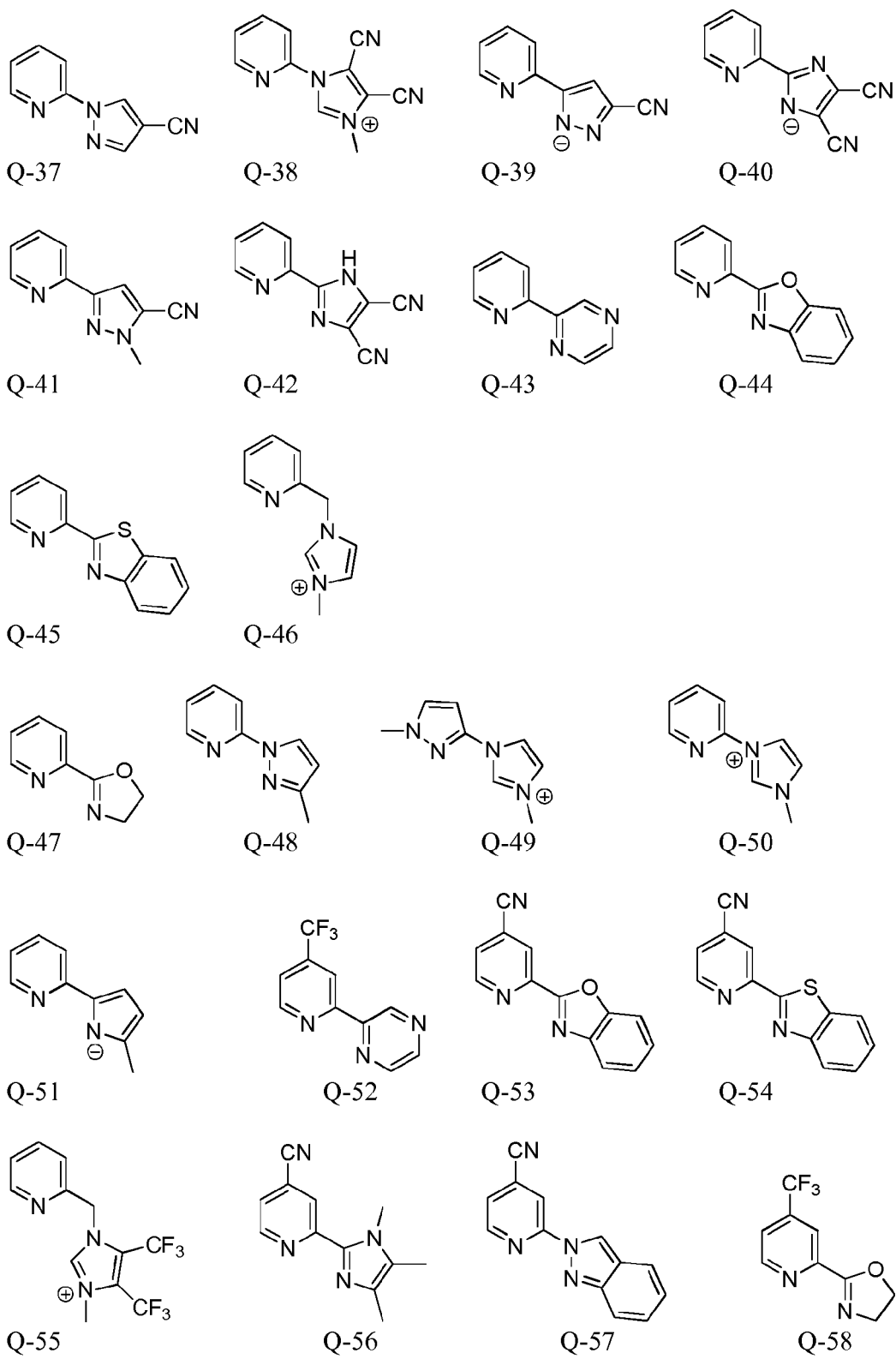
Figures 4, 15:
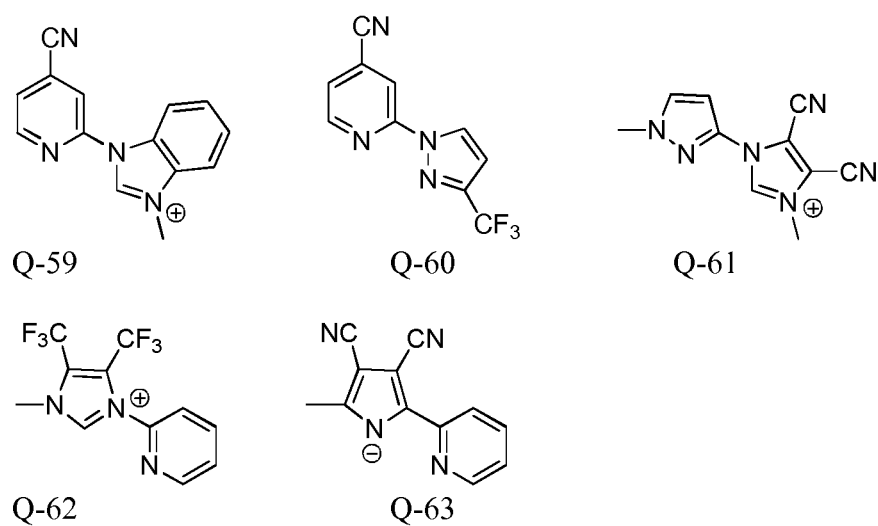

FIG. 7 compares IPCE spectra of the device in accordance with an embodiment of the invention with the device using the $I^-/I_3^-$-based electrolyte (Z960). It can be seen from FIG. 7 that for the $Co^{2+}/Co^{3+}$ redox mediator, the IPCE spectrum is significantly enhanced in the blue and red region with respect to that observed for the $I^-/I_3^-$ based electrolyte. The increased blue response of the photocurrent between 400 and 450 nm is attributed to lower light absorption of the $Co^{2+}/Co^{3+}$ redox mediator compared to the $I^-/I_3^-$-based electrolyte in this wavelength domain, as shown by the absorption spectra in FIG. 5. However, the main contribution to the increase of the Jsc (Table 2) arises from the red shift of the IPCE spectrum starting at around 600 nm. The origin of this interesting and beneficial effect is surprising and the inventors do not have a straightforward explanation for these results.

Example 11

Synthesis of CoII and CoIII Complexes $Co(bpy-pz)_2[B(CN)_4]_2$ and $Co(bpy-pz)_2[B(CN)_4]_3$ 91 mg (0.382 mmol, excess) of $CoCl_2*6H_2O$ were dissolved in 25 mL of water while in another flask 93 mg (0.418 mmol) of the pyridine-pyridine-pyrazole ligand of Example 1 were dissolved in 25 mL of acetone. The solutions were combined and heated to 55° C. for 2 h. After 5 minutes of stirring potassium tetracyanoborate (1.2 g) in water was added. The mixture was stored overnight at 3° C. for precipitation. The precipitated complex was filtered, washed with water and dried under vacuum to isolate $Co(bpy-pz)_2[B(CN)_4]_2$.

91 mg (0.382 mmol, excess) of $CoCl_2 \cdot 6H_2O$ were dissolved in 25 mL of water while in another flask 93 mg (0.418 mmol) of the pyridine-pyridine-pyrazole ligand of Example 1 were dissolved in 25 mL of acetone. The solutions were combined and heated to 55° C. for 2 h. After 5 minutes of stirring was added one molar equivalent of bromine solution in methanol while stirring. After 5 minutes more stirring the solution was filtered to remove any precipitate. Then the solvent was evaporated using a rotavapour under vacuum and dissolved in methanol solution (15 ml) and filtered. To the filtrate was added potassium tetracyanoborate (1.2 g) in water. The precipitated complex was filtered, washed with water and dried under vacuum to isolate $Co(bpy-pz)_2[B(CN)_4]_3$.

Example 12

Preparation of Dye Sensitized Solar Cell Using the Complex-Based Redox-Couple of Example 11

The solar cells are prepared as discussed in Example 10.

The invention claimed is:
1. An electrochemical or optoelectronic device comprising a first and a second electrode and, between said first and second electrode, a charge transport layer, said a charge transport layer comprising a complex-based redox couple being added in the form of a salt of tetracyanoborate $(B(CN)_4)$ having tetracyanoborate $([B(CN)_4]^-)$ as anion and a cationic metal complex of formula I:

$$M(La)_n(Xb)_m \qquad (I)$$

wherein:
M is a 1$^{st}$ row transition metal selected from the metals Sc, Ti, V, Cr, Mn, Fe, Co, Ni, Cu, and Zn;
n is an integer from 1 to 3 and a is a consecutive number of a first set consisting of the integers of 1 to n (1, . . . , n), so that there are n ligands L1, . . . , Ln;
m is 0 or an integer from 1 to 5 and b is a consecutive number of a second set consisting of 0 and integers of 1 to m (0, . . . , m), so that if m>0 there are m ligands X1, . . . , Xm;
provided the sum of n and m equal the appropriate total number of ligands present on metal M;
each ligand La is independently selected from mono-, bi-, and tridentate ligands, comprising a substituted or unsubstituted ring or ring system, said ring or ring system comprising at least one nitrogen atom;
each co-ligand Xb is independently selected from $H_2O$, $Cl^-$, $Br^-$, $I^-$, $CN^-$, $NCO^-$, $NCS^-$, $NCSe^-$, $NH_3$, $NR_{10}R_{11}R_{12}$, $PR_{10}R_{11}R_{12}$, $R_{10}$, wherein $R_{10}$, $R_{11}$, and $R_{12}$ may be selected independently from substituted or unsubsituted alkyl, alkenyl, alkynyl and phenyl,
wherein each said La is independently selected from any one of compounds of formulae (2), (3), (64), (66) and (68) as shown below:

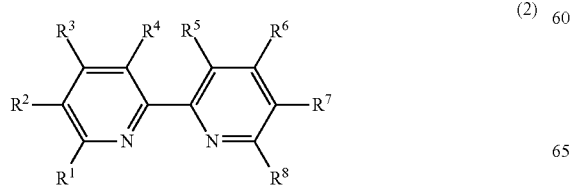

-continued

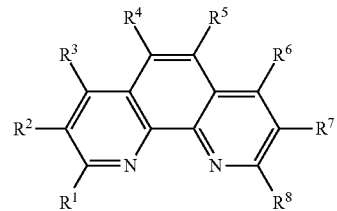

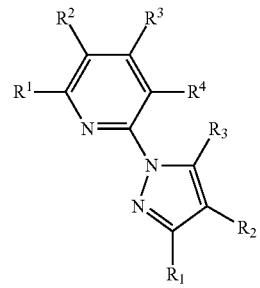

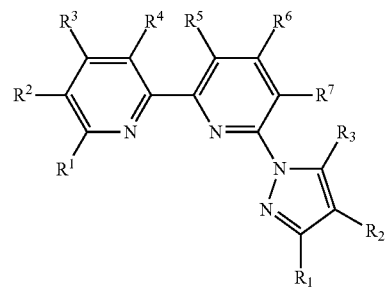

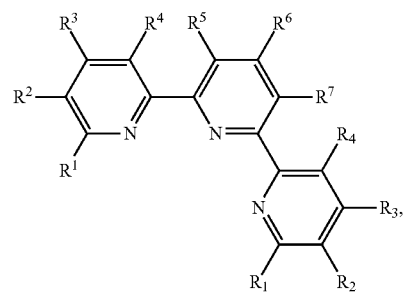

wherein $R^1$, $R^2$, $R^3$, $R^4$, $R^5$, $R^6$, $R^7$, and $R^8$ of formulae (2), (3), in as far as present, are selected independently from H, halogen (—F, —Cl, —Br, —I), —CN, and from C1-C6 alkyl and alkenyl, wherein any available hydrogen of said alkyl and alkenyl may or may not be replaced by halogen and/or —CN and from the substituents of formula (A-3), (A-5), (A-6), (B-5), (B-6), (B-8), (B-9), (B-10), (B-11), (B-12), (B-13), (B-14), (B-15), (B-17), (B-21), (B-22), (B-24), (B-25), (B-26), (B-27), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-24), (C-25), (C-26), (C-27), (D-1), (D-2), (D-3), (E-1), (E-2), (E-3), (F-1), (F-2), (F-3), (F-4), (F-5), (F-6), (F-7), (F-9), (F-10), (G-1), (G-2) below:

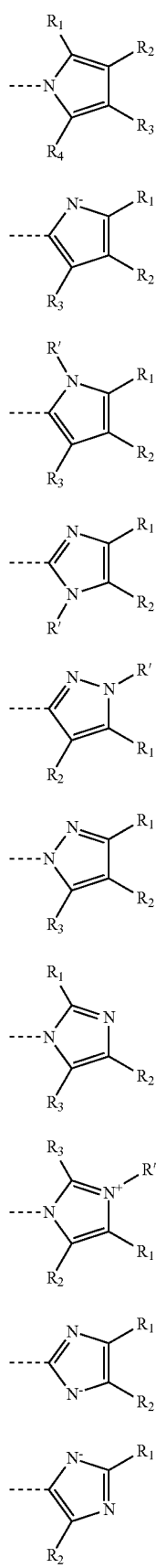

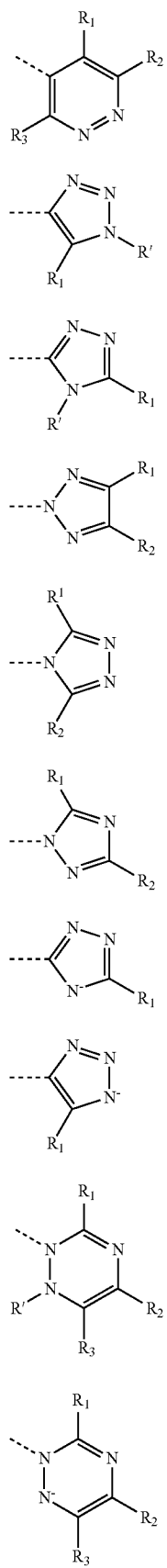
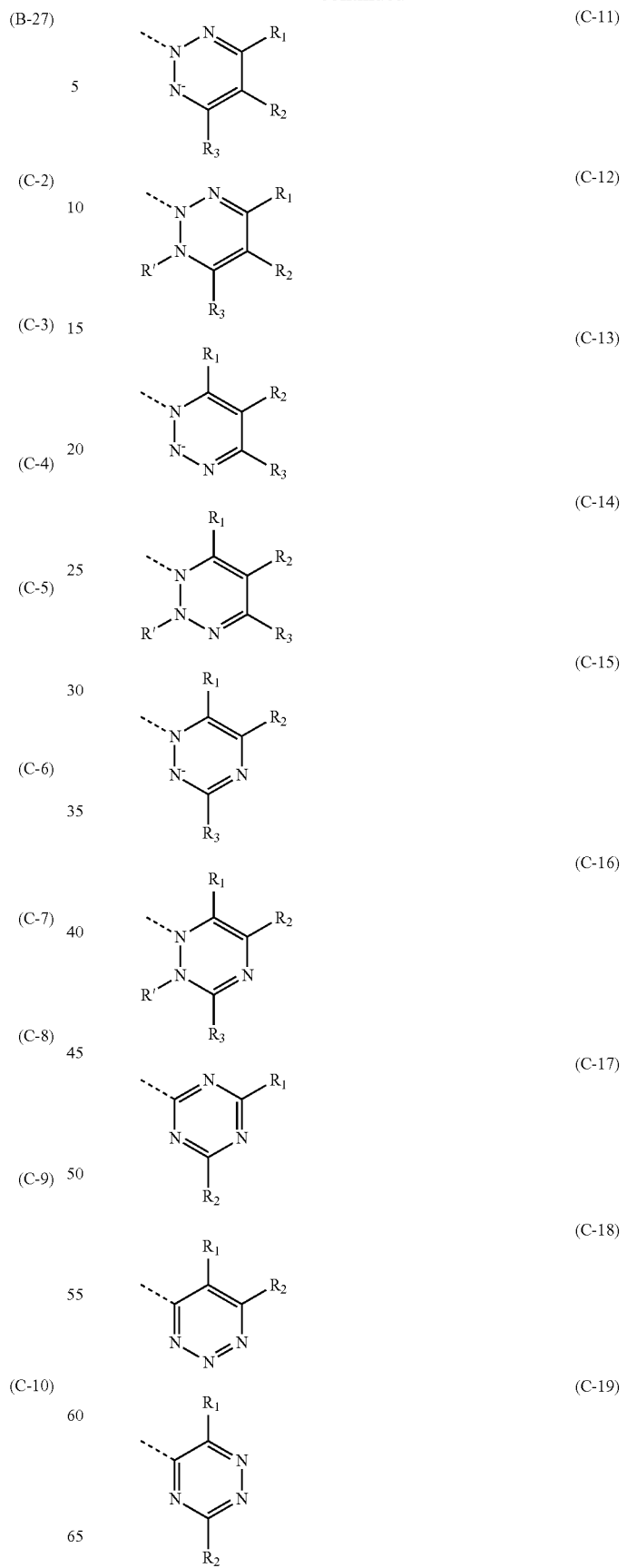

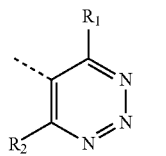 (C-20)
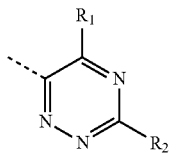 (C-21)
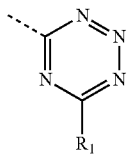 (C-24)
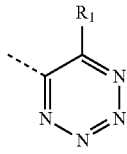 (C-25)
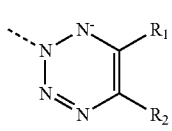 (C-26)
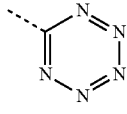 (C-27)
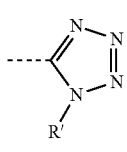 (D-1)
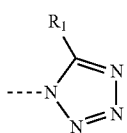 (D-2)
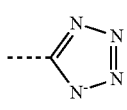 (D-3)
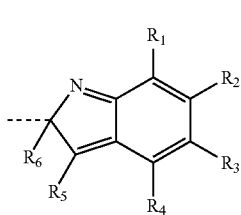 (E-1)
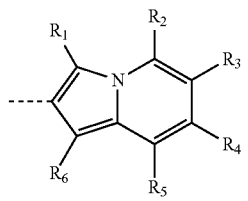 (E-2)
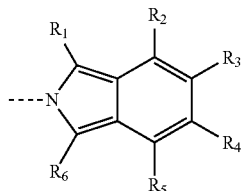 (E-3)
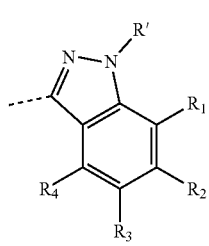 (F-1)
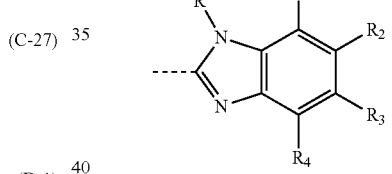 (F-2)
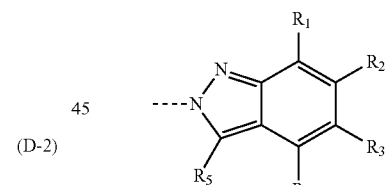 (F-3)
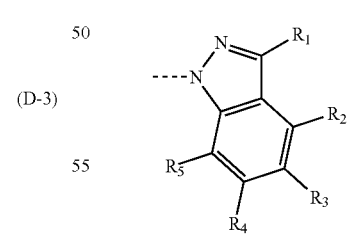 (F-4)
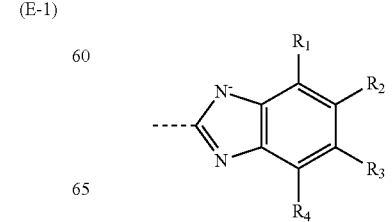 (F-5)

-continued

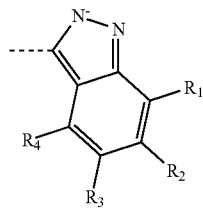 (F-6)

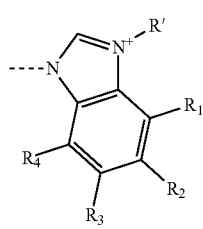 (F-7)

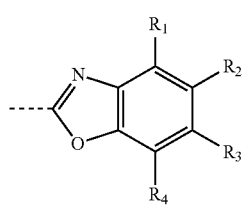 (F-9)

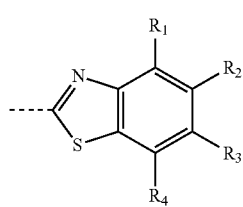 (F-10)

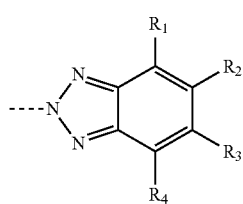 (G-1)

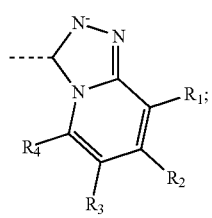 (G-2)

wherein the dotted line represents the bond connecting the substituent of (A-1) to (G-2) on the respective compound of formula (2), (3), (64), (66) and (68); and, $R_1$, $R_2$, $R_3$, $R_4$, $R_5$, and $R_6$ from formulae (A-3) to (G-2), in as far as present, are independently selected from H, hydrocarbons comprising 1 to 20 carbons and 0 to 20 heteroatoms, halogen, (—F, —Cl, —Br, —I), and —NO$_2$; and R' of substituents (B-10), (C-9), (C-12), (C-14), and (C-16) is selected from H and from C1-C6 linear branched or cyclo alkyl, said alkyl being possibly and optionally substituted by halogen; and wherein $R^1$, $R^2$, $R^3$, $R^4$, $R^5$, $R^6$, $R^7$ of formulae (64), (66) and (68), in as far as applicable, are H, and $R_1$, $R_2$, $R_3$, $R_4$, $R_5$, $R_6$ of formulae (64), (66) and (68), in as far as applicable, are selected from H, —CN, and —CF$_3$.

2. The device according to claim 1, wherein said charge transport layer comprises an organic solvent and/or comprises one or more ionic liquids.

3. The device according to claim 1, wherein said first electrode is a semiconductor electrode comprising a surface facing the charge transport layer of the device, wherein a dye is adsorbed on said surface so as to form a layer on said surface, wherein said dye is selected from dyes carrying no charge or carrying a positive charge or carrying a negative charge when being adsorbed on said surface.

4. The device according to claim 3, wherein said dye adsorbed on said surface lacks any negatively charged, free (non-anchored) anchoring group.

5. The device according to claim 3, wherein said dye comprises a single anchoring group, by way of which said dye is attached to said surface.

6. The device according to claim 1, which is selected from a photo-electrochemical device, an optoelectronic device, an electrochemical battery, (for example a lithium ion battery), a double layer capacitor, a light emitting device, an electrochromic or photo-electrochromic device, an electrochemical sensor, a biosensor, an electrochemical display and an electrochemical capacitor.

7. The device according to claim 1, which is a photoelectric conversion device, preferably a dye-sensitized solar cell or photovoltaic cell.

8. The device according to claim 1, wherein n is 3, m is 0 and/or wherein the ligands L1, L2, L3 are independently selected from compounds of formulae (2), (3) and (64).

9. The device according to claim 1, wherein n is 2, m is 0 or 1, and/or wherein L1 and L2 are selected independently from the compounds of formulae (66) and (68).

10. A method of preparing a electrochemical device, the method comprising the steps of:
providing a first and a second electrode;
providing a charge transport layer;
adding to said charge transport layer a salt comprising tetracyanoborate ([B(CN)$_4$]$^-$) and a cationic metal complex of formula I:

$$M(La)_n(Xb)_m \qquad (I)$$

wherein:
M, n, m, La and Xb are as defined in claim 1.

11. The device according to claim 1, wherein n is 2 and L1 and L2 is identical or wherein n is 3 and L1, L2 and L3 are identical.

* * * * *

UNITED STATES PATENT AND TRADEMARK OFFICE
CERTIFICATE OF CORRECTION

PATENT NO. : 9,779,879 B2
APPLICATION NO. : 14/001062
DATED : October 3, 2017
INVENTOR(S) : Mohammed Khaja Nazeeruddin et al.

It is certified that error appears in the above-identified patent and that said Letters Patent is hereby corrected as shown below:

In the Specification

<u>Column 33</u>
- Line 67: "...intersection n). ..." to be replaced with "...intersection ∩). ..."

<u>Column 34</u>
- Line 19: "...A,BandC;..." to be replaced with "...A, B and C;..."
- Line 44: "...A,B,CandG;..." to be replaced with "...A, B, C and G;..."

Signed and Sealed this
Twenty-eighth Day of November, 2017

Joseph Matal
*Performing the Functions and Duties of the
Under Secretary of Commerce for Intellectual Property and
Director of the United States Patent and Trademark Office*